US010077457B2

(12) United States Patent
Bathe et al.

(10) Patent No.: US 10,077,457 B2
(45) Date of Patent: Sep. 18, 2018

(54) METHOD FOR THE FERMENTATIVE PRODUCTION OF L-AMINO ACIDS USING IMPROVED STRAINS OF THE *ENTEROBACTERIACEAE* FAMILY

(71) Applicant: Evonik Degussa GmbH, Essen (DE)

(72) Inventors: Brigitte Bathe, Salzkotten (DE); Stella Molck, Bielefeld (DE); Horst Priefert, Ostbevern (DE)

(73) Assignee: EVONIK DEGUSSA GMBH, Essen (DE)

( * ) Notice: Subject to any disclaimer, the term of this patent is extended or adjusted under 35 U.S.C. 154(b) by 447 days.

(21) Appl. No.: 14/422,751

(22) PCT Filed: Jul. 31, 2013

(86) PCT No.: PCT/EP2013/066066
§ 371 (c)(1),
(2) Date: Feb. 20, 2015

(87) PCT Pub. No.: WO2014/029592
PCT Pub. Date: Feb. 27, 2014

(65) Prior Publication Data
US 2015/0353973 A1 Dec. 10, 2015

(30) Foreign Application Priority Data

Aug. 20, 2012 (EP) .................... 12181028

(51) Int. Cl.
 C07K 14/245 (2006.01)
 C12N 15/70 (2006.01)
 C12N 1/20 (2006.01)
 C12P 13/12 (2006.01)
(52) U.S. Cl.
 CPC ............ *C12P 13/12* (2013.01); *C07K 14/245* (2013.01); *C12N 1/20* (2013.01); *C12N 15/70* (2013.01)

(58) Field of Classification Search
CPC combination set(s) only.
See application file for complete search history.

(56) References Cited

U.S. PATENT DOCUMENTS

2012/0190084 A1    7/2012  Schneider et al.

FOREIGN PATENT DOCUMENTS

| EP | 2479279 A1 | 7/2012 |
| KR | 2005/0079338 A | 8/2005 |
| RU | 2312894 C1 | 12/2007 |
| WO | WO-2005/085463 A1 | 9/2005 |
| WO | WO-2008/127240 A1 | 10/2008 |
| WO | 2010020671 A1 | 2/2010 |

OTHER PUBLICATIONS

Mellies et al., "Two Different *Escherichia coli* Prop Promoters Response to Osmotic and Growth Phase Signals", Journal of Bacteriology, Jan. 1995, p. 144-151.
Hondorp et al., "Oxidative Stress Inactivates Cobalamin-Independent Methionine Synthase (MetE) in *Escherichia coli*", Protein Engineering for Therapeutics, Part B, Nov. 2004, vol. 2, Issue 11, pp. 1738-1747.
Old et al., "Regulation of Methionine Biosynthesis in the Enterobacteriaceae§", Prog. Biophys, Molec. Biol. vol. 56, pp. 145-185, 1991.
English Abstract for KR 2005 0079338.
International Preliminary Report on Patentability dated Mar. 5, 2015 in PCT/EP2013/066066.

*Primary Examiner* — Kagnew H Gebreyesus
(74) *Attorney, Agent, or Firm* — Reed Smith LLP; Ryan P. Cox

(57) ABSTRACT

The present invention relates to a process for the fermentative production of L-amino acids using microorganisms of the Enterobacteriaceae family, which harbor an attenuated proP gene, to the microorganisms suitable for said production and to polynucleotides coding for variants of the ProP transporter.

13 Claims, 3 Drawing Sheets
Specification includes a Sequence Listing.

Figure 1: Map of plasmid pCC3
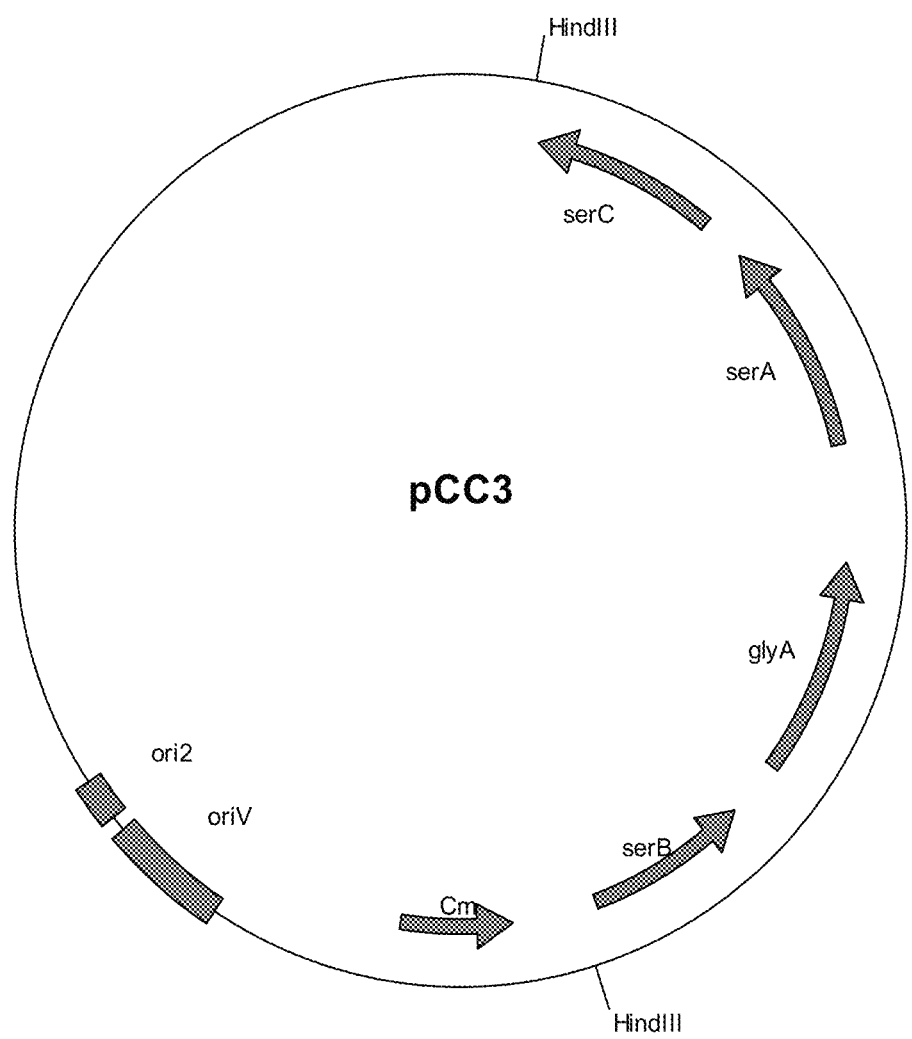

Figure 2: Map of plasmid pME-RDL2a
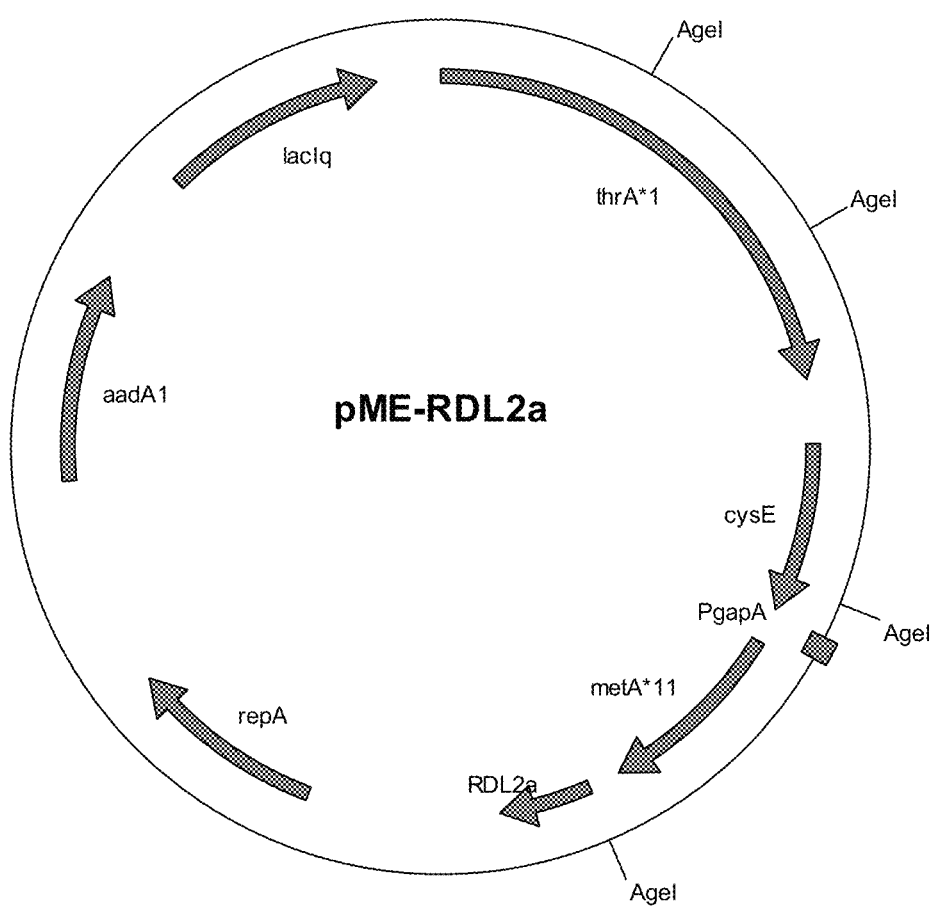

Figure 3: Map of plasmid pMAK_proP-M8
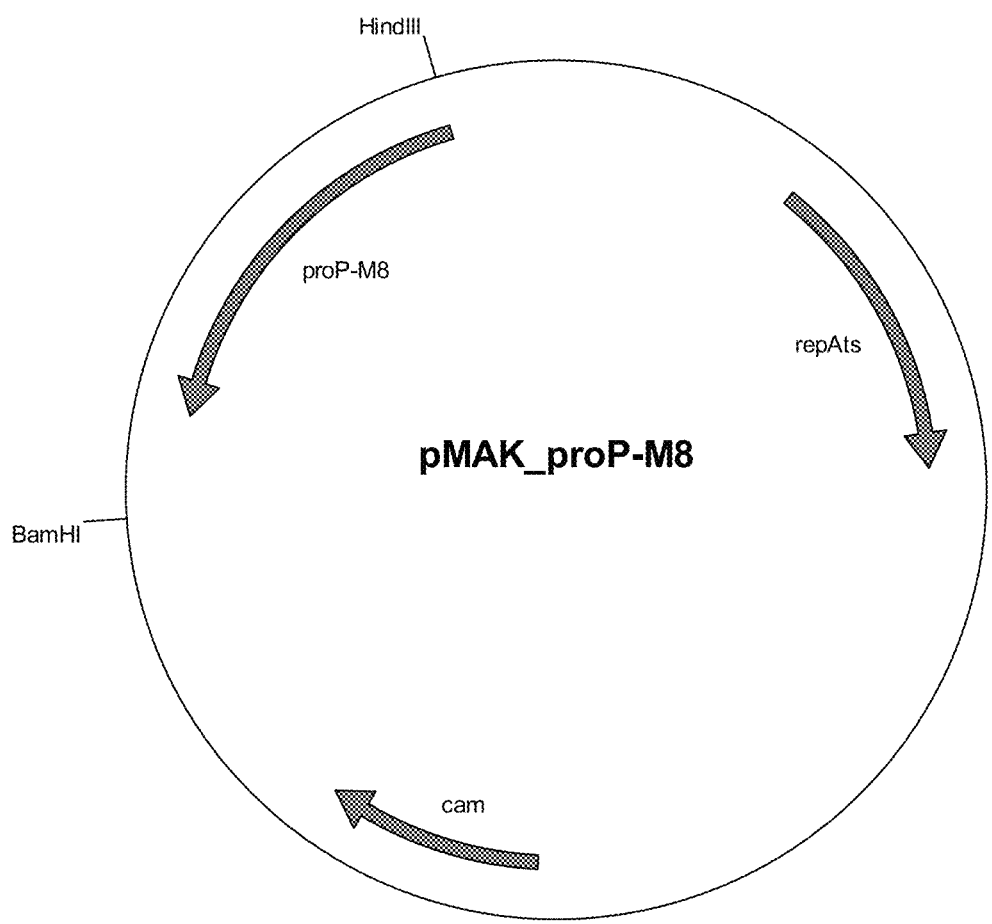

METHOD FOR THE FERMENTATIVE PRODUCTION OF L-AMINO ACIDS USING IMPROVED STRAINS OF THE ENTEROBACTERIACEAE FAMILY

CROSS REFERENCE TO RELATED APPLICATIONS

This application is a National Phase filing under 35 U.S.C. § 371 of PCT/EP2013/066066 filed on Jul. 31, 2013; and this application claims priority to Application No. 12181028.7 filed in Europe on Aug. 20, 2012 under 35 U.S.C. § 119. The entire contents of each application are hereby incorporated by reference.

The present invention relates to a process for the fermentative production of L-amino acids using microorganisms of the Enterobacteriaceae family, which harbour an attenuated proP gene, to the microorganisms suitable for said production and to polynucleotides coding for variants of the ProP transporter.

Organic chemical compounds, more specifically sulphur-containing L-amino acids, are of great economic importance. L-Cysteine is used as food supplement, as starting material for pharmacological active compounds (for example N-acetylcysteine) and for cosmetics. The amino acid L-methionine plays a prominent role in animal nutrition and is one of the essential amino acids which cannot be produced biosynthetically in the metabolism of vertebrates. In animal breeding it must consequently be ensured that sufficient quantities of the particular amino acid are taken in with the feed. However, since L-methionine, for example, is often present in conventional feedstuff plants (such as soya or cereals) in amounts which are too low to ensure optimum animal nutrition, especially for pigs and poultry, it is advantageous to admix methionine as an additive to the animal feed. Vertebrates can convert D-methionine into biologically active L-methionine. A racemate of D- and L-methionine is therefore usually added to the animal feed. Animals can convert L-homocysteine into L-methionine by transmethylation, and the former can therefore replace the latter.

Organic chemical compounds as mentioned hereinbelow mean one or more compounds selected from the group of L-amino acids, preferably sulphur-containing L-amino acids, in particular L-methionine, L-cysteine, L-cystine, L-homocysteine and L-homocystine. Preference is given to L-methionine.

In the prior art, amino acids such as methionine are prepared by chemical synthesis. This involves firstly reacting acrolein and methyl mercaptan to give 3-(methylthio) propionaldehyde which in turn with cyanide, ammonia and carbon monoxide produces hydantoin. Finally, the latter may be hydrolysed to the racemate, an equimolar mixture of the two stereoisomers, D- and L-methionine. Since the biologically active form of the molecule is represented only by the L form, the D form present in the feed must first metabolically be converted by de- and transamination into the active L form.

In contrast to methionine, most other natural, proteinogenic amino acids such as L-threonine, for example, are chiefly prepared by fermentation of microorganisms. This takes advantage of the fact that microorganisms have appropriate biosynthetic pathways for synthesis of the natural amino acids. Moreover, many fermentation processes achieve very favourable production costs by using inexpensive reactants such as glucose and mineral salts, and also deliver the biologically active L form of the particular amino acid.

It is known that organic chemical compounds can be produced by fermentation of strains of Enterobacteriaceae, in particular *Escherichia coli* (*E. coli*) and *Serratia marcescens*. Due to their great significance, efforts are constantly being made to improve the preparation procesess. Improvements to the process may relate to measures concerning fermentation technology, for example stirring and oxygen supply, or to the composition of the nutrient media, such as, for example, selection of the sugar used or sugar concentration during fermentation, or to work up to the product form by, for example, ion exchange chromatography, or to the intrinsic performance characteristics of the microorganism itself.

Biosynthetic pathways of amino acids in wild-type strains are subject to strict metabolic control which ensures that the amino acids are produced only for the cell's intrinsic needs. An important prerequisite for efficient production processes is therefore the availability of suitable microorganisms which, in contrast to wild-type organisms, have a drastically increased production output, in excess of the intrinsic needs (overproduction), for the preparation of the desired amino acid.

Such amino acid-overproducing microorganisms may be generated by classic mutation/selection processes and/or by modern, specific, recombinant techniques ("metabolic engineering"). The latter involves firstly identifying genes or alleles which effect amino acid overproduction due to their modification, activation or inactivation. These genes/alleles are then introduced into a strain of a microorganism or inactivated using molecular biology techniques so as to achieve optimum overproduction. However, often only combining a plurality of different measures leads to a truly efficient production.

L-Methionine, along with lysine and threonine, is derived from aspartate. Sulphur is introduced in the form of L-cysteine (via cystathionine as intermediate) into L-methionine by transsulphuration. The $CH_3$ group of L-methionine originates from C1 metabolism and is transferred to L-homocysteine by the MetE or MetH methionine synthases (review: Greene R C (1996) in Neidhardt F C et al. (eds.) "*Escherichia coli* and *Salmonella*", $2^{nd}$ edition, pp. 542-560). Strains and processes for fermentative production of L-methionine have been described for *E. coli* in WO2006/001616 or WO2009/043803, for example.

ProP is the *E. coli* proton/compatible solute symporter, and thus one of the transporters in *E. coli* that are active under hyperosmotic conditions (Grothe et al., Journal of Bacteriology 166, 253-259 (1986); Racher et al., Biochemistry 38, 1676-1684 (1999); Wood, Methods in Enzymology 428, 77-107 (2007)). Upon an increase in osmolality of the medium surrounding the cell, the medium's water potential decreases and water molecules diffuse along the osmotic gradient out of the cell. The cell's turgor pressure decreases, and following that, the cytoplasmic proteins are deprived of their functionally relevant hydration shell. As a result of this dehydration, cell metabolism and cell division come to a standstill. To prevent this, microorganisms have developed different strategies in the course of evolution, for example through synthesis and/or absorption of what are known as compatible solutes. If these naturally occurring protectants, for example proline or glycine betaine, are available externally, absorption thereof, which is quicker and also energetically more favourable, is preferred over the microorganisms' own synthesis (Wood, Microbiology and Molecular Biology Reviews 63, 230-262 (1999)). The ProP symporter belongs to the MFS family (major facilitator superfamily) and catalyses the absorption of proline, glycine betaine, proline betaine, ectoine and other, structurally similar substrates in symport with protons into the cell under hyperosmotic conditions. ProP was the first transporter for which osmosensing and osmoregulatory properties were detected in the reconstituted system. The C-terminal domain is capable of forming a coiled coil motif. Formation of this domain is important for osmoregulation and possibly for sensing osmotic stimuli (Culham et al., Journal of Molecular Recognition 13, 309-322 (2000)). ProP is activated by internal increases in the concentration of potassium ions and by macromolecular crowding which was imitated in proteoliposomes by using polyethylene glycol (PEG) of different chain lengths (Racher et al., Biochemistry 40, 7324-7333 (2001); Culham et al., Biochemistry 42, 410-420 (2003)). Although ProP is capable of sensing osmotic stress situations without additional factors, full activity of the carrier in vivo requires the presence of the cytoplasmic ProQ protein, however (Kunte et al., Journal of Bacteriology 181, 1537-43 (1999)).

Thus, the E. coli ProP transporter has been known for quite some time for its function in osmoregulation.

Suprisingly, we have now found according to the invention that production of L-amino acids by microorganisms of the Enterobacteriaceae family can be increased by attenuating the proP gene.

It was an object of the present invention to provide a process and microorganisms, which enable overproduction of sulphur-containing amino acids, more specifically L-methionine, to be increased.

BRIEF DESCRIPTION OF THE DRAWINGS

FIG. 1 shows the map of the plasmid pCC3 which was obtained by cloning the genes serB-glyA-serAC from pUC18-serB-glyA-serAC to pCC1-BAC (Example 1).

FIG. 2 shows the map of the production plasmid pME-RDL2a, which includes the E. coli cysE gene, feedback-resistant alleles of the E. coli thrA and metA genes and the RDL2a gene coding for the S. cerevisiae RDL2p thiosulphate sulphurtransferase and in addition a streptomycin-resistance gene.

FIG. 3 shows the map of the plasmid pMAK_roP-M8 which was obtained by cloning the proP allele M8 from DM2321 into the pMAK705 plasmid.

DESCRIPTION OF THE INVENTION

A first subject matter of the present invention is a process for the production of L-amino acids or feed additives containing L-amino acid by fermentation of a microorganism of the Enterobacteriaceae family, characterized in that a microorganism in which the proP gene has been attenuated is employed.

Said microorganism produces the L-amino acid and secretes it preferably into the surrounding medium.

The microorganism furthermore causes the L-amino acid to accumulate preferably in the medium and/or inside the cell (accumulation), with particular preference being given to accumulation in the medium.

Another subject matter of the present invention is therefore also a microorganism of the Enterobacteriaceae family, which harbours an attenuated proP gene, characterized in that it produces L-amino acids and preferably secretes them into the medium, preferably causing the L-amino acids to accumulate in the medium and/or inside the cell, preferably in the medium.

The microorganism here preferably shows increased production and preferably excretion of the desired L-amino acid in a fermentation process, compared to the starting strain or parent strain employed without attenuated proP gene.

"Attenuated" means according to the invention that the proP gene either is expressed at a low level or has been eliminated completely.

In this context, the term "attenuation" describes according to the invention reducing or eliminating the intracellular activity or concentration of one or more enzymes or proteins, more specifically herein the ProP transporter, in a microorganism, which are encoded by the corresponding DNA, more specifically herein by the proP gene, by using for example a weaker promoter than in the microorganism or parent strain that is not recombinant for the respective enzyme or protein, or using a gene or allele coding for a respective low-activity enzyme or protein, or inactivating the respective enzyme or protein or the open reading frame or the gene, and, where appropriate, combining these measures.

The measures of attenuation usually lower the activity or concentration of the respective protein to from 0 to 75%, 0 to 50%, 0 to 25%, 0 to 10%, or 0 to 5%, of the activity or concentration of the wild-type protein, or of the activity or concentration of the protein in the microorganism or parent strain that is not recombinant for the respective enzyme or protein. A non-recombinant microorganism or parent strain is understood as meaning the microorganism which is subjected to the attenuation or elimination according to the invention.

Attenuation may be achieved, for example, by reducing or eliminating either expression of the genes or open reading frames or the catalytic properties of the enzyme proteins. Both measures may be combined, where appropriate.

Gene expression may be reduced by a suitable culturing procedure, by genetic modification (mutation) of the signal structures of gene expression, or else by antisense-RNA technology. Examples of signal structures of gene expression are repressor genes, activator genes, operators, promoters, attenuators, ribosome-binding sites, the start codon and terminators. Information on this can be found by a person skilled in the art inter alia, for example, in Jensen and Hammer (Biotechnology and Bioengineering 58: 191-195 (1998)), in Carrier and Keasling (Biotechnology Progress 15: 58-64 (1999)), Franch and Gerdes (Current Opinion in Microbiology 3: 159-164 (2000)), Kawano et al. (Nucleic Acids Research 33(19), 6268-6276 (2005)) and in known textbooks of genetics and molecular biology, for example the textbook by Knippers ("Molekulare Genetik", 6th edition, Georg Thieme Verlag, Stuttgart, Germany, 1995) or that by Winnacker ("Gene and Klone", VCH Verlagsgesellschaft, Weinheim, Germany, 1990).

Mutations which result in a change or reduction in the catalytic properties of enzyme proteins have been disclosed in the prior art; examples which may be mentioned are the studies by Qiu and Goodman (Journal of Biological Chemistry 272: 8611-8617 (1997)), Yano et al. (Proceedings of the National Academy of Sciences of the United States of America 95: 5511-5515 (1998)), Wente and Schachmann (Journal of Biological Chemistry 266: 20833-20839 (1991)). Overviews may be found in known textbooks of genetics and molecular biology, for example that by Hagemann ("Allgemeine Genetik", Gustav Fischer Verlag, Stuttgart, 1986).

Mutations which may be considered are transitions, transversions, insertions and deletions of at least one (1) base pair or nucleotide. Depending on the effect of the amino acid substitution caused by the mutation on the enzyme activity, reference is made to missense mutations or nonsense mutations. The missense mutation leads to a substitution of a given amino acid in a protein by a different one, more specifically a non-conservative amino acid substitution. This impairs the functionality or activity of said protein, which is reduced to from 0 to 75%, 0 to 50%, 0 to 25%, 0 to 10%, or 0 to 5%. The nonsense mutation results in a stop codon within the coding region of the gene and consequently to translation being terminated prematurely. Insertions or deletions of at least one base pair in a gene lead to frame shift mutations as a result of which incorrect amino acids are incorporated or translation is terminated prematurely. If a stop codon is generated within the coding region as a result of the mutation, then this likewise causes translation to be terminated prematurely. Likewise, deletions of at least one (1) or more codons typically result in a total loss of enzyme activity. WO 03/074719 describes reduction of gene expression by suppressing a stop-codon mutation in the coding region by means of suitable t-RNA suppressors.

Instructions for generating such mutations belong to the prior art and can be found in known textbooks of genetics and molecular biology, for example the textbook by Knippers ("Molekulare Genetik", 6th edition, Georg Thieme Verlag, Stuttgart, Germany, 1995), that by Winnacker ("Gene and Klone", VCH Verlagsgesellschaft, Weinheim, Germany, 1990) or that by Hagemann ("Allgemeine Genetik", Gustav Fischer Verlag, Stuttgart, 1986).

"Attenuation" and "expression at a low level" mean more particularly with regard to the proP gene that the activity and/or concentration of the ProP transporter is lowered by the measures illustrated hereinabove to from 0 to 75%, 0 to 50%, 0 to 25%, 0 to 10%, or 0 to 5%, of the activity and/or concentration of the wild-type protein, or of the activity and/or concentration of the protein in the microorganism or parent strain that is non-recombinant for the ProP transporter.

According to the invention, the L-amino acid is preferably overproduced by the microorganism. "Overproduction" means according to the invention that production performance regarding the L-amino acid is drastically increased in excess of the microorganism's intrinsic needs.

The L-amino acid according to the invention is preferably a sulphur-containing amino acid, in particular L-methionine, L-cysteine, L-cystine, L-homocysteine or L-homocystine, particularly preferably L-methionine.

The microorganisms according to the invention and employed in processes according to the invention are preferably distinguished by having increased methionine tolerance compared to the microorganisms without attenuated proP gene. Preferably, they are capable here of growing even at an L-methionine concentration of 50 or 60 grams per liter, particularly preferably even at an L-methionine concentration of 70, 75, 80, 90, or 100 grams per liter, since they are resistant to those methionine concentrations. The tolerance data regarding L-methionine here are preferably based on a minimal agar having corresponding L-methionine concentrations.

Such methionine-resistant strains may be isolated by selection on methionine-containing minimal agar, starting from an *E. coli* strain already producing L-methionine.

The methionine-resistant bacteria according to the invention are generated using preferably selection methods described in the prior art, which methods may be looked up inter alia in Miller (A Short Course in Bacterial Genetics, A Laboratory Manual and Handbook for *Escherichia coli* and Related Bacteria (Cold Spring Harbor Laboratory Press, 1992)) or in the "Manual of Methods for General Bacteriology" of the American Society for Bacteriology (Washington D.C., USA).

Another subject matter of the present invention is therefore a process for identifying microorganisms of the Enterobacteriaceae family, which enable sulphur-containing L-amino acids, preferably L-methionine, to be produced in an improved manner and which harbour an attenuated proP gene, said process comprising the steps of a) screening microorganisms of the Enterobacteriaceae family, which are capable of producing sulphur-containing L-amino acids, preferably L-methionine, for increased methionine tolerance;

b) isolating and propagating the mutants generated in a);

c) optionally providing nucleic acids from the mutants obtained in b);

d) optionally preparing a nucleic acid molecule by using the polymerase chain reaction, starting from nucleic acid from c) and a primer pair consisting of a first primer comprising at least 15 contiguous nucleotides from position 1 to position 1000 of the nucleotide sequence of SEQ ID NO:38 and a second primer comprising at least 15 contiguous nucleotides from position 2504 to position 3503 of the complementary nucleotide sequence of SEQ ID NO:38;

e) optionally determining the nucleotide sequence of the nucleic acid molecule obtained in d), and determining the encoded amino acid sequence;

f) optionally comparing the amino acid sequence determined in e) with SEQ ID NO:2; and g) optionally identifying the proP mutant obtained.

To specifically carry out mutations in the proP gene, site-directed mutagenesis procedures using mutagenic oligonucleotides (T. A. Brown: Gentechnologie für Einsteiger [orig. title: Gene Cloning and DNA Analysis—An Introduction], Spektrum Akademischer Verlag, Heidelberg, Germany, 1993) or polymerase chain reaction (PCR), as described in the manual by Gait: Oligonucleotide synthesis: A Practical Approach (IRL Press, Oxford, UK, 1984) or by Newton and Graham (PCR, Spektrum Akademischer Verlag, Heidelberg, 1994), may be used. To engineer mutations, the Quick Change Site-Directed Mutagenesis kit from Stratagene (Amsterdam, Netherlands) may be used, for example. Using these methods involves amplifying the proP gene described in the prior art with the aid of the polymerase chain reaction (PCR) starting from isolated total DNA of a wild-type strain, cloning said gene into suitable plasmid vectors, and then subjecting the DNA to the mutagenesis process. By means of "GeneSOEing" (Gene Splicing by Overlap Extension, Horton, Molecular Biotechnology 3: 93-98 (1995)), the point mutations may even be obtained by PCR. A de novo gene synthesis (for example by GENEART A G, Regensburg, Germany) of the nucleotide sequences may also be used for producing mutations in the proP gene. The mutations generated can be determined and checked by DNA sequencing, for example by the method of Sanger et al. (Proceedings of the National Academy of Science USA 74 (12): 5463-5467, 1977).

The alleles generated may be incorporated into the chromosome of appropriate strains, for example by transformation and the method of gene or allele substitution.

A customary method, described by Hamilton et al. (Journal of Bacteriology 171, 4617-4622 (1989)), is the method of gene substitution with the aid of a conditionally replicating pSC101 derivative pMAK705 or with pKO3 (Link et al., Journal of Bacteriology 179: 6228-6237). Other methods described in the prior art, for example that of Martinez-Morales et al. (Journal of Bacteriology 1999, 7143-7148

(1999)) or that of Boyd et al. (Journal of Bacteriology 182, 842-847 (2000)), may likewise be utilized.

Another customary method consists of incorporating via short, homologous flanking sequences a DNA fragment generated by PCR or gene synthesis directly into the chromosome with the aid of Lambda Red recombinase, or carrying out a substitution (Proc. Natl. Acad. Sci. USA 97(12), 6640-6645 (2000); Nature Genetics 20, 123-128, 1998).

It is likewise possible to transfer, by conjugation or transduction, the alleles generated into various strains.

The proP nucleic acid sequences may be found in the databases of the National Center for Biotechnology Information (NCBI), the National Library of Medicine (Bethesda, Md., USA), the nucleotide sequence database of the European Molecular Biologies Laboratories (EMBL, Heidelberg, Germany and Cambridge, UK) or the DNA database of Japan (DDBJ, Mishima, Japan).

For illustration purposes, the known sequence of the *Escherichia coli*_proP gene is listed under SEQ ID NO: 1, and the known sequences of the proP genes of *Salmonella enterica* and *Shigella sonnei* which likewise belong to the Enterobacteriaceae family, are listed under SEQ ID NO: 3 and SEQ ID NO: 5. The proteins encoded by these reading frames are listed by way of SEQ ID NO: 2, SEQ ID NO: 4 and SEQ ID NO: 6. Further nucleotide sequences for the proP gene are found, for example, in the following Enterobacteriaceae: *Shigella boydii* (Accession NO: NC_007613); *Shigella flexneri* (Accession NO: NC_004741); *Shigella dysenteriae* (Accession NO: NC_007606); *Citrobacter rodentium* (Accession NO: NC_013716); *Erwinia pyrifoliae* (Accession NO: NC_012214); *Klebsiella pneumoniae* (Accession NO: NC_011283).

The protein encoded by the *Escherichia coli* K12_proP gene is also referred to as osmosensoric MFS transporter ProP or as proton/compatible solute symporter (Accession NO: 11612 (Region: 4328525-4330027); alternative gene names: b4111, ECK4104); Grothe et al., Journal of Bacteriology 166, 253-259 (1986); Racher et al., Biochemistry 38, 1676-1684 (1999); Wood, Methods in Enzymology 428, 77-107 (2007)).

In a preferred embodiment according to the invention, the proP gene to be attenuated is a gene having a sequence identity of at least 80%, preferably of at least 90%, in particular of at least 95%, especially of at least 98, 99 or 100%, based on preferably the complete polynucleotide sequences of SEQ ID NO: 1, 3, 5 or 7, particularly preferably based on the complete polynucleotide sequence of SEQ ID NO: 1.

References in the literature regarding the proP genes and open reading frames of said proP genes have been indicated above. These may be used according to the invention in an appropriate manner in order to attenuate the proP gene. Furthermore, alleles of the genes or open reading frames that result from the degeneracy of the genetic code or on account of functionally neutral sense mutations may also be used for preparing an attenuated proP gene. The use of endogenous genes or endogenous open reading frames is preferred.

Alleles of the proP gene that contain functionally neutral sense mutations include amongst others those which result in no more than 40 or no more than 30 or no more than 20, preferably no more than 10 or no more than 5, very particularly preferably no more than 3 or no more than 2, or in exactly one conservative amino acid substitution in the protein encoded by them.

In the case of aromatic amino acids, conservative substitutions are those in which phenylalanine, tryptophan and tyrosine are substituted for each other. In the case of hydrophobic amino acids, conservative substitutions are those in which leucine, isoleucine and valine are substituted for each other. In the case of polar amino acids, conservative substitutions are those in which glutamine and asparagine are substituted for one another. In the case of basic amino acids, conservative substitutions are those in which arginine, lysine and histidine are substituted for each other. In the case of acidic amino acids, conservative substitutions are those in which aspartic acid and glutamic acid are substituted for one another. In the case of amino acids containing hydroxyl groups, conservative substitutions are those in which serine and threonine are substituted for one another.

Similarly, those nucleotide sequences that code for variants of the proteins mentioned, which additionally contain an extension or truncation by at least one (1) amino acid at the N or C terminus, may also be used. Said extension or truncation constitutes no more than 10, 5, 3 or 2 amino acids or amino acid residues.

Suitable variants also include those coding for proteins in which at least one (1) amino acid has been inserted (insertion) or removed (deletion). The maximum number of such modifications referred to as indels may affect 2, 3, 5, but in no case more than 10 amino acids.

Suitable variants also include those obtainable by hybridization, in particular under stringent conditions, using SEQ ID NO: 1, SEQ ID NO: 3 or SEQ ID NO: 5 or parts thereof, in particular the coding regions and/or the sequences complementary thereto.

Instructions regarding the identification of DNA sequences by means of hybridization can be found by a person skilled in the art inter alia in the manual "The DIG System User's Guide for Filter Hybridization" from Boehringer Mannheim GmbH (Mannheim, Germany, 1993) and in Liebl et al. (International Journal of Systematic Bacteriology 41: 255-260 (1991)). Hybridization takes place under stringent conditions, that is to say only hybrids in which the probe and the target sequence, i.e. the polynucleotides treated with said probe, are at least 70% identical are formed. The stringency of the hybridization, including the washing steps, is known to be influenced or determined by varying the buffer composition, temperature and salt concentration. The hybridization reaction is generally carried out with relatively low stringency compared with the washing steps (Hybaid Hybridisation Guide, Hybaid Limited, Teddington, UK, 1996).

For example, a 5×SSC buffer at a temperature of approx. 50° C.-68° C. may be employed for the hybridization reaction. Here, probes may also hybridize with polynucleotides which are less than 70% identical to the sequence of the probe. Such hybrids are less stable and are removed by washing under stringent conditions. This may be achieved, for example, by lowering the salt concentration to 2×SSC and, where appropriate, subsequently 0.5×SSC (The DIG System User's Guide for Filter Hybridisation, Boehringer Mannheim, Mannheim, Germany, 1995), with a temperature of approx. 50° C.-68° C., approx. 52° C.-68° C., approx. 54° C.-68° C., approx. 56° C.-68° C., approx. 58° C.-68° C., approx. 60° C.-68° C., approx. 62° C.-68° C., approx. 64° C.-68° C., approx. 66° C.-68° C. being set. Preference is given to temperature ranges of approx. 64° C.-68° C. or approx. 66° C.-68° C. It is optionally possible to lower the salt concentration to a concentration corresponding to 0.2× SSC or 0.1×SSC. By gradually increasing the hybridization temperature in steps of approx. 1-2° C. from 50° C. to 68° C., it is possible to isolate polynucleotide fragments which are, for example, at least 70% or at least 80% or at least 90%, at least 91%, at least 92%, at least 93%, at least 94%, at least 95%, at least 96%, at least 97%, at least 98%, or at least 99%, identical to the sequence of the probe employed or the nucleotide sequences depicted in SEQ ID NO: 1, SEQ ID NO: 3 or SEQ ID NO: 5. Further instructions regarding hybridization are obtainable on the market in the form of "kits" (e.g. DIG Easy Hyb from Roche Diagnostics GmbH, Mannheim, Germany, Catalogue No. 1603558).

The proP gene to be attenuated codes for the ProP transporter protein which preferably has an amino acid sequence that is at least 85%, in particular at least 90%, preferably at least 95%, particularly preferably at least 98%, at least 99%, or 100%, identical to the amino acid sequence of SEQ ID NO:2, SEQ ID NO: 4, SEQ ID NO: 6 or SEQ ID NO: 8, preferably to the amino acid sequence of SEQ ID NO: 2, said identity preferably being over the entire length of the sequence(s) indicated. The ProP transporter protein preferably comprises or has essentially a length of 500 amino acids, a length of 500 amino acids being preferred. The ProP protein very particularly preferably comprises or has the amino acid sequence of SEQ ID NO: 2, which sequence may optionally include no more than 40, no more than 30, preferably no more than 20, no more than 10, no more than 5, no more than 3, no more than 2, particularly preferably no more than one, conservative amino acid substitution(s). The conservative amino acid substitutions essentially do not alter the activity of the ProP transporter, that is to say according to the invention preferably that said activity is altered by said conservative amino acid substitutions by no more than 10%, based on the starting sequence.

In this connection, the term "essentially a length of 500 amino acids" takes into account the fact that insertion or deletion of one (1) or more, no more than 10, 9, 8, 7, 6, 5, 4, 3 or 2, amino acids within the polypeptide or at the N- or C-terminal end of said polypeptide results in a slight variation of the length of the encoded polypeptide in different species or strains of the Enterobacteriaceae family. One example of this is the *Erwinia pyrifoliae* ProP protein. In this case, the length of the polypeptide (see SEQ ID No:8) is 501 amino acids.

In embodiments preferred according to the invention, attenuation of the proP gene of SEQ ID NO: 1 is achieved by the gene having any of the following mutations:
a) substitution of the nucleobase guanine in position 971 or a comparable position of the polynucleotide sequence of SEQ ID NO:1 by the nucleobase thymine;
b) substitution of the nucleobase thymine in position 1399 or a comparable position of the polynucleotide sequence of SEQ ID NO:1 by the nucleobase cytosine;
c) substitution of the nucleobase guanine in position 1234 or a comparable position of the polynucleotide sequence of SEQ ID NO:1 by the nucleobase thymine;
d) deletion of the nucleobase adenine in position 854 of the polynucleotide sequence of SEQ ID NO: 1;
e) deletion of one or more of the nucleobases from position 1173 to position 1223, preferably deletion of all nucleobases from position 1173 to position 1223, of the polynucleotide sequence of SEQ ID NO:1;
f) insertion of the nucleobase cytosine in position 842 of the polynucleotide sequence of SEQ ID NO:1;
g) insertion of one or more nucleobase(s) in position 973, preferably insertion of 19 nucleobases in position 973, of the polynucleotide sequence of SEQ ID NO:1;
h) insertion of one or more nucleobase(s) in position 183, preferably insertion of 1359 nucleobases in position 183, of the polynucleotide sequence of SEQ ID NO:1.

In embodiments preferred according to the invention, the attenuated proP gene is therefore a polynucleotide which has a sequence identity of at least 80%, preferably of at least 90%, in particular of at least 95%, particularly preferably of at least 98, 99 or 100%, based on the polynucleotide of SEQ ID NO: 1, preferably based on the complete sequence of the polynucleotide of SEQ ID NO: 1, and which furthermore mandatorily has one or more, preferably exactly one, of the following mutations over the polynucleotide of SEQ ID NO: 1:

a) substitution of the triplet coding for L-arginine in position 324 of SEQ ID NO: 2 or a comparable position of the amino acid sequence by a triplet coding for an amino acid selected from the group consisting of L-leucine, L-isoleucine and L-valine, preferably L-leucine;
b) substitution of the triplet coding for L-tyrosine in position 467 of SEQ ID NO: 2 or a comparable position of the amino acid sequence by a triplet coding for an amino acid selected from the group consisting of L-lysine, L-arginine and L-histidine, preferably L-histidine;
c) substitution of the triplet coding for L-glutamic acid in position 412 of SEQ ID NO: 2 or a comparable position of the amino acid sequence by a triplet coding for a stop codon;
d) deletion of the nucleobase adenine in position 854 of the proP gene of SEQ ID NO:1;
e) deletion of one or more of the nucleobases from position 1173 to position 1223, preferably deletion of all nucleobases from position 1173 to position 1223, of the proP gene of SEQ ID NO:1;
f) insertion of the nucleobase cytosine in position 842 of the proP gene of SEQ ID NO:1;
g) insertion of one or more nucleobase(s) in position 973, preferably insertion of 19 nucleobases in position 973, of the proP gene of SEQ ID NO:1;
h) insertion of one or more nucleobase(s) in position 183, preferably insertion of 1359 nucleobases in position 183, of the proP gene of SEQ ID NO:1.

The identities indicated based on the polynucleotide of SEQ ID NO: 1 here in each case relate to the polynucleotide sequence without the one or more mandatory mutations mentioned above.

"Comparable positions" can readily be identified by comparing the amino acid sequences by way of an alignment, for example with the aid of the Clustal W program (Thompson et al., Nucleic Acids Research 22, 4637-4680 (1994)) or with the aid of the MAFFT program (Katoh et al., Genome Information 2005; 16(1), 22-33).

The microorganism according to the invention and to be employed in processes according to the invention of the Enterobacteriaceae family is preferably a bacterium of the genera *Escherichia, Erwinia, Providencia* or *Serratia*, in particular of the genus *Escherichia*. It is particularly preferably *Escherichia coli.*

In processes according to the invention for producing the L-amino acid, in particular the sulphur-containing L-amino acid, fermentation is preferably carried out in a medium containing an inorganic sulphur source. A sulphur source which may be used is a salt of dithiosulphuric acid (thiosulphate), where appropriate together with other sulphur sources such as sulphate, sulphite or dithionite, for example (see also EP application 11151526.8).

The L-amino acid is preferably caused to accumulate in the fermentation broth obtained and is then, where appropriate, isolated, collected and/or purified.

The L-amino acid may also be isolated or collected together with components from the fermentation broth and/or biomass.

The output of the isolated bacteria or of the fermentation process using the same with regard to one or more of the parameters selected from the group of product concentration (product per volume), product yield (product formed per carbon source consumed) and product formation (product formed per volume and time), or else other process parameters and combinations thereof, is preferably improved by at least 0.5%, at least 1%, at least 1.5% or at least 2%, based on the starting strain or parent strain or the fermentation process using the same.

In the process according to the invention, the bacteria may be cultured continuously—as described, for example, in PCT/EP2004/008882- or discontinuously in a batch process (batch cultivation) or in a fed batch or repeated fed batch process for the purpose of producing L-amino acids. A summary of a general nature about known cultivation methods is available in the textbook by Chmiel (Bioprozesstechnik 1. Einführung in die Bioverfahrenstechnik (Gustav Fischer Verlag, Stuttgart, 1991)) or in the textbook by Storhas (Bioreaktoren and periphere Einrichtungen (Vieweg Verlag, Brunswick/Wiesbaden, 1994)).

The culture medium or fermentation medium to be used must in a suitable manner satisfy the demands of the particular strains. Descriptions of culture media for various microorganisms are included in the Manual of Methods for General Bacteriology of the American Society for Bacteriology (Washington D.C., USA, 1981). The terms culture medium and fermentation medium or medium are interchangeable.

Carbon sources that may be used are sugars and carbohydrates such as, for example, glucose, sucrose, lactose, fructose, maltose, molasses, sucrose-containing solutions from sugar beet or sugar cane processing, starch, starch hydrolysate and cellulose, oils and fats such as, for example, soybean oil, sunflower oil, groundnut oil and coconut oil, fatty acids such as, for example, palmitic acid, stearic acid and linoleic acid, alcohols such as, for example, glycerol, methanol and ethanol, and organic acids such as, for example, acetic acid. These substances may be used individually or as mixture.

Nitrogen sources that may be used are organic nitrogen-containing compounds such as peptones, yeast extract, meat extract, malt extract, corn steep liquor, soybean flour and urea, or inorganic compounds such as ammonium sulphate, ammonium chloride, ammonium phosphate, ammonium carbonate and ammonium nitrate. The nitrogen sources may be used individually or as mixture.

Phosphorus sources that may be used are phosphoric acid, potassium dihydrogen phosphate or dipotassium hydrogen phosphate or the corresponding sodium-containing salts.

The culture medium furthermore preferably comprises salts, for example in the form of chlorides, of metals such as, for example, sodium, potassium, magnesium, calcium and iron, such as, for example, magnesium sulphate or iron sulphate, which are necessary for growth. Finally, essential growth factors such as amino acids, for example homoserine, and vitamins, for example cobalamin, thiamine, biotin or pantothenic acid, may be employed in addition to the above-mentioned substances.

Moreover, suitable precursors of the particular amino acid may be added to the culture medium.

Said starting materials may be added in the form of a single batch to the culture or be fed in in a suitable manner during cultivation.

The pH of the culture is controlled by employing in a suitable manner basic compounds such as sodium hydroxide, potassium hydroxide, ammonia or aqueous ammonia, or acidic compounds such as phosphoric acid or sulphuric acid. The pH is generally adjusted to a value of from 6.0 to 9.0, preferably 6.5 to 8. To control foaming, it is possible to employ antifoams such as, for example, fatty acid polyglycol esters. To maintain the stability of plasmids, it is possible to add to the medium suitable substances with selective action such as, for example, antibiotics. To maintain aerobic conditions, oxygen or oxygen-containing gas mixtures such as, for example, air are introduced into the culture. It is likewise possible to use liquids enriched with hydrogen peroxide. Fermentation is performed, where appropriate, at elevated pressure, for example at a pressure of from 0.03 to 0.2 MPa. The temperature of the culture is normally from 20° C. to 45° C. and preferably from 25° C. to 40° C. In batch processes, culturing is continued until a maximum amount of the desired amino acid has formed. This target is normally reached within 10 hours to 160 hours. In continuous processes, longer culturing times are possible.

Suitable fermentation media are described, inter alia, in U.S. Pat. No. 6,221,636, in U.S. Pat. No. 5,840,551, in U.S. Pat. No. 5,770,409, in U.S. Pat. No. 5,605,818, in U.S. Pat. No. 5,275,940 and in U.S. Pat. No. 4,224,409.

Methods of determining L-amino acids have been disclosed in the prior art. For example, the analysis may be performed, as described in Spackman et al. (Analytical Chemistry, 30, (1958), 1190), by means of ion exchange chromatography with subsequent ninhydrin derivatization, or it may be performed by means of reversed-phase HPLC, as described in Lindroth et al. (Analytical Chemistry (1979) 51: 1167-1174).

The fermentation broth produced in this way is then preferably processed to a solid or liquid product.

A fermentation broth means a fermentation medium in which a microorganism has been cultured for a certain time and at a certain temperature. The fermentation medium or the medium employed during fermentation preferably includes any substance or component that ensures propagation of said microorganism and formation of the desired amino acid.

Upon completion of the fermentation, the resulting fermentation broth accordingly comprises a) the biomass of the microorganism, formed as a result of propagation of the cells of said microorganism, b) the desired amino acid formed during fermentation, c) the organic byproducts formed during fermentation, and d) the constituents of the fermentation medium/fermentation media employed or of the starting materials such as, for example, vitamins such as biotin, amino acids such as homoserine or salts such as magnesium sulphate, which have not been consumed in said fermentation.

The organic byproducts include substances which are generated by the microorganisms employed in the fermentation optionally in addition to the particular desired L-amino acid and which may be excreted. They include L-amino acids which make up less than 30%, 20% or 10%, compared to the desired amino acid. They furthermore include organic acids carrying from one to three carboxyl groups, such as acetic acid, lactic acid, citric acid, malic acid or fumaric acid, for example. Finally, they also include sugars such as trehalose, for example.

Typical fermentation broths that are suitable for industrial purposes and preferred according to the invention have an amino acid content of from 40 g/kg to 180 g/kg or 50 g/kg to 150 g/kg. The biomass content (as dried biomass) is usually from 20 to 50 g/kg.

Accordingly, the present invention also relates to polynucleotides having an identity of at least 80%, preferably at least 90%, in particular at least 95%, especially at least 98, 99 or 100%, based on the sequence of SEQ ID NO: 1, the identity indicated preferably relating to the total sequence of SEQ ID NO: 1, characterized in that the polynucleotide mandatorily has one or more mutations over the polynucleotide of SEQ ID NO: 1, selected from:

a) substitution of the triplet coding for L-arginine in position 324 of SEQ ID NO: 2 or a comparable position of the amino acid sequence by a triplet coding for an amino acid selected from the group consisting of L-leucine, L-isoleucine and L-valine, preferably L-leucine;
b) substitution of the triplet coding for L-tyrosine in position 467 of SEQ ID NO: 2 or a comparable position of the amino acid sequence by a triplet coding for an amino acid selected from the group consisting of L-lysine, L-arginine and L-histidine, preferably L-histidine;
c) substitution of the triplet coding for L-glutamic acid in position 412 of SEQ ID NO: 2 or a comparable position of the amino acid sequence by a triplet coding for a stop codon;
d) deletion of the nucleobase adenine in position 854 of the proP gene of SEQ ID NO:1;
e) deletion of one or more of the nucleobases from position 1173 to position 1223, preferably deletion of all nucleobases from position 1173 to position 1223, of the proP gene of SEQ ID NO:1;
f) insertion of the nucleobase cytosine in position 842 of the proP gene of SEQ ID NO:1;
g) insertion of one or more nucleobase(s) in position 973, preferably insertion of 19 nucleobases in position 973, of the proP gene of SEQ ID NO:1;
h) insertion of one or more nucleobase(s) in position 183, preferably insertion of 1359 nucleobases in position 183, of the proP gene of SEQ ID NO:1.

The identities indicated based on the polynucleotide of SEQ ID NO: 1 here in each case relate to the polynucleotide sequence without the one or more mandatory mutations mentioned above.

Particular preference is given here to the one or more mandatory mutation(s) selected from:

a) substitution of the nucleobase guanine in position 971 or a comparable position of the polynucleotide sequence of SEQ ID NO:1 by the nucleobase thymine;
b) substitution of the nucleobase thymine in position 1399 or a comparable position of the polynucleotide sequence of SEQ ID NO:1 by the nucleobase cytosine;
c) substitution of the nucleobase guanine in position 1234 or a comparable position of the polynucleotide sequence of SEQ ID NO:1 by the nucleobase thymine;
d) deletion of the nucleobase adenine in position 854 of the polynucleotide sequence of SEQ ID NO: 1;
e) deletion of one or more of the nucleobases from position 1173 to position 1223, preferably deletion of all nucleobases from position 1173 to position 1223, of the polynucleotide sequence of SEQ ID NO:1;
f) insertion of the nucleobase cytosine in position 842 of the polynucleotide sequence of SEQ ID NO:1;
g) insertion of one or more nucleobase(s) in position 973, preferably insertion of 19 nucleobases in position 973, of the polynucleotide sequence of SEQ ID NO:1;
h) insertion of one or more nucleobase(s) in position 183, preferably insertion of 1359 nucleobases in position 183, of the polynucleotide sequence of SEQ ID NO:1.

According to the invention, the above-mentioned polynucleotides according to the invention are preferably distinguished by hybridizing with one or more of the polynucleotides complementary to SEQ ID NO: 1, 3 or 5, preferably complementary to SEQ ID NO: 1, preferably under stringent hybridization conditions, said stringent conditions preferably being attained by a washing step in which the temperature ranges from 64° C. to 68° C. and the salt concentration of the buffer ranges from 2×SSC to 0.1×SSC.

Particularly preferred polynucleotides according to the invention have a sequence identity of at least 90%, preferably at least 95%, in particular at least 98, 99 or 100%, to the polynucleotides of SEQ ID NO: 9, SEQ ID NO: 11, SEQ ID NO: 13, SEQ ID NO: 15, SEQ ID NO: 17, SEQ ID NO: 19, SEQ ID NO: 21 or SEQ ID NO: 23.

Very particularly preferred polynucleotides according to the invention are and/or comprise the polynucleotides of SEQ ID NO: 9, SEQ ID NO: 11, SEQ ID NO: 13, SEQ ID NO: 15, SEQ ID NO: 17, SEQ ID NO: 19, SEQ ID NO: 21 and SEQ ID NO: 23.

The present invention also relates to vectors comprising polynucleotides according to the invention.

Accordingly, the present invention also relates to polypeptides having an identity of at least 80%, preferably at least 90%, in particular at least 95%, especially at least 98, 99 or 100%, based on the sequence of SEQ ID NO: 2, characterized in that the polypeptide mandatorily has one or more mutations over the polypeptide of SEQ ID NO: 2, selected from:

a. substitution of L-arginine in position 324 of SEQ ID NO: 2 or a comparable position of the amino acid sequence by an amino acid selected from the group consisting of L-leucine, L-isoleucine and L-valine, preferably L-leucine;
b. substitution of L-tyrosine in position 467 of SEQ ID NO: 2 or a comparable position of the amino acid sequence by an amino acid selected from the group consisting of L-lysine, L-arginine and L-histidine, preferably L-histidine;
c. deletion of the 17 amino acids from position 392 to position 408 of SEQ ID NO: 2 or a comparable position of the amino acid sequence;
d. deletion of up to 420 amino acids of the C terminus, based on the sequence of SEQ ID NO: 2, preferably deletion of 88, 163, 202, 212 or 420 amino acids of the C terminus of the amino acid sequence of SEQ ID NO: 2.

The identities indicated here relate for the mutants of a and b to the total sequence of SEQ ID NO: 2, for the mutants of c and d in each case to the subregions of the sequence of SEQ ID NO: 2 without the deleted regions indicated.

Preferred polypeptides according to the invention are polypeptides having a sequence identity of at least 90%, preferably at least 95%, in particular at least 98, 99 or 100%, to the polypeptides of SEQ ID NO: 10, 12, 14, 16, 18, 20, 22 or 24.

Particularly preferred polypeptides according to the invention are and/or comprise polypeptides of SEQ ID NO: 10, 12, 14, 16, 18, 20, 22 or 24.

The present invention also relates to recombinant microorganisms harbouring polynucleotides and/or vectors and/or polypeptides according to the invention.

Microorganisms according to the invention and microorganisms employed in processes according to the invention preferably have an enhanced aspartate kinase (EC 2.7.2.4) enzyme activity, with preference being given to feedback-resistant alleles. *E. coli* possesses three different aspartate kinases encoded by the thrA, metL or lysC genes. Particular preference is given, according to the invention, to an enhanced activity of the ThrA aspartate kinase being present.

Microorganisms according to the invention and microorganisms employed in processes according to the invention are furthermore preferably distinguished by having increased activity of the MetA homoserine O-succinyltransferase (EC 2.3.1.46) and/or the CysE serine acetyltransferase (EC 2.3.1.30).

It is furthermore possible to increase L-methionine biosynthesis by attenuating or deleting the MetJ regulatory protein encoded by the metJ gene. MetJ is the major repressor of L-methionine biosynthesis in *E. coli*. Accordingly, preference is furthermore given according to the invention to the metJ gene being attenuated.

Microorganisms according to the invention and microorganisms employed in processes according to the invention are furthermore preferably distinguished by having reduced activity of the MetK S-adenosylmethionine synthase (EC 2.5.1.6).

It may furthermore be advantageous for the production of sulphur-containing amino acids using bacteria of the Enterobacteriaceae family to additionally enhance one or more enzyme(s) of the known amino acid biosynthetic pathways or enzyme(s) of the anaplerotic metabolism or enzymes for producing reduced nicotinamide adenine dinucleotide phosphate or enzymes of glycolysis or PTS enzymes or enzymes of sulphur metabolism or to increase their activity.

In further, preferred embodiments, the L-methionine-producing bacteria possess one or more of the features selected from the group consisting of:
a) overexpressed polynucleotide coding for one or more components of the CysPUWA thiosulphate/sulphate transport system (EC 3.6.3.25),
b) overexpressed polynucleotide coding for a CysH 3'-phosphoadenosine 5'-phosphosulphate reductase (EC 1.8.4.8),
c) overexpressed polynucleotide coding for one or more components of the CysJI sulphite reductase (EC 1.8.1.2),
d) overexpressed polynucleotide coding for a CysK cysteine synthase A (EC 2.5.1.47),
e) overexpressed polynucleotide coding for a CysM cysteine synthase B (EC 2.5.1.47),
f) overexpressed polynucleotide coding for a CysE serine acetyltransferase (EC 2.3.1.30),
g) overexpressed polynucleotide coding for one or more components of the GcvTHP-Lpd glycine cleavage system (EC 2.1.2.10, EC 1.4.4.2, EC 1.8.1.4),
h) overexpressed polynucleotide coding for a LipA lipoyl synthase (EC 2.8.1.8),
i) overexpressed polynucleotide coding for a LipB lipoyl-protein ligase (EC 2.3.1.181),
j) overexpressed polynucleotide coding for a SerA phosphoglycerate dehydrogenase (EC 1.1.1.95),
k) overexpressed polynucleotide coding for a SerB 3-phosphoserine phosphatase (EC 3.1.3.3),
l) overexpressed polynucleotide coding for a SerC 3-phosphoserine/phosphohydroxythreonine aminotransferase (EC 2.6.1.52),
m) overexpressed polynucleotide coding for a GlyA serine hydroxymethyltransferase (EC 2.1.2.1),
n) overexpressed polynucleotide coding for a ThrA aspartokinase I and homoserine dehydrogenase I (EC 2.7.2.4, EC 1.1.1.3),
o) overexpressed polynucleotide coding for a LysC aspartate kinase (EC 2.7.2.4),
p) overexpressed polynucleotide coding for a Hom homoserine dehydrogenase (EC 1.1.1.3),
q) overexpressed polynucleotide coding for a MetX homoserine O-acetyltransferase (EC 2.3.1.31),
r) overexpressed polynucleotide coding for a MetA homoserine O-succinyltransferase (EC 2.3.1.46),
s) overexpressed polynucleotide coding for a MetB cystathionine gamma synthase (EC 2.5.1.48),
t) overexpressed polynucleotide coding for an AecD β-C—S-lyase (EC 4.4.1.8, also referred to as beta-lyase),
u) overexpressed polynucleotide coding for a MetC cystathionine beta-lyase (EC 4.4.1.8),
v) overexpressed polynucleotide coding for a MetE B12-independent homocysteine S-methyltransferase (EC 2.1.1.14),
w) overexpressed polynucleotide coding for a MetH B12-dependent homocysteine S-methyltransferase (EC 2.1.1.13),
x) overexpressed polynucleotide coding for a MetF methylene tetrahydrofolate reductase (EC 1.5.1.20),
y) overexpressed polynucleotide coding for one or more components of the *Corynebacterium glutamicum* BrnFE L-methionine exporter,
z) overexpressed polynucleotide coding for one or more components of the *Escherichia coli* YgaZH valine exporter (b2682, b2683),
aa) overexpressed polynucleotide coding for the putative *Escherichia coli* YjeH transporter (b4141),
bb) overexpressed polynucleotide coding for one or more components of the PntAB pyridine nucleotide transhydrogenase (EC 1.6.1.2),
cc) overexpressed polynucleotide coding for a MetZ O-succinylhomoserine sulphhydrylase (EC 2.5.1.48),
dd) overexpressed polynucleotide coding for a Pyc phosphoenolpyruvate carboxylase (EC 4.1.1.31),
ee) overexpressed polynucleotide coding for an RDL2 thiosulphate sulphurtransferase (EC 2.8.1.1),
ff) overexpressed polynucleotide coding for a thiosulphate-thiol sulphurtransferase (EC 2.8.1.3),
gg) overexpressed polynucleotide coding for a thiosulphate-dithiol sulphurtransferase (EC 2.8.1.5).

Preferred features here are one or more selected from the group consisting of:
a) overexpressed polynucleotide coding for one or more components of the CysPUWA thiosulphate/sulphate transport system (EC 3.6.3.25),
b) overexpressed polynucleotide coding for a CysH 3'-phosphoadenosine 5'-phosphosulphate reductase (EC 1.8.4.8),
c) overexpressed polynucleotide coding for one or more components of the CysJI sulphite reductase (EC 1.8.1.2),
d) overexpressed polynucleotide coding for a CysK cysteine synthase A (EC 2.5.1.47),
e) overexpressed polynucleotide coding for a CysM cysteine synthase B (EC 2.5.1.47),
f) overexpressed polynucleotide coding for a CysE serine acetyltransferase (EC 2.3.1.30),
g) overexpressed polynucleotide coding for one or more components of the GcvTHP-Lpd glycine cleavage system (EC 2.1.2.10, EC 1.4.4.2, EC 1.8.1.4),
h) overexpressed polynucleotide coding for a LipA lipoyl synthase (EC 2.8.1.8),
i) overexpressed polynucleotide coding for a LipB lipoyl-protein ligase (EC 2.3.1.181),
j) overexpressed polynucleotide coding for a SerA phosphoglycerate dehydrogenase (EC 1.1.1.95), k) overexpressed polynucleotide coding for a SerB 3-phosphoserine phosphatase (EC 3.1.3.3),
l) overexpressed polynucleotide coding for a SerC 3-phosphoserine/phosphohydroxythreonine aminotransferase (EC 2.6.1.52),
m) overexpressed polynucleotide coding for a GlyA serine hydroxymethyltransferase (EC 2.1.2.1),
n) overexpressed polynucleotide coding for a ThrA aspartokinase I and homoserine dehydrogenase I (EC 2.7.2.4, EC 1.1.1.3),
o) overexpressed polynucleotide coding for a LysC aspartate kinase (EC 2.7.2.4),
p) overexpressed polynucleotide coding for a Hom homoserine dehydrogenase (EC 1.1.1.3),
q) overexpressed polynucleotide coding for a MetX homoserine acetyltransferase (EC 2.3.1.31),
r) overexpressed polynucleotide coding for a MetA homoserine O-transsuccinylase (EC 2.3.1.46),
s) overexpressed polynucleotide coding for a MetB cystathionine gamma synthase (EC 2.5.1.48),
t) overexpressed polynucleotide coding for an AecD β-C—S-lyase (EC 4.4.1.8, also referred to as beta-lyase),
u) overexpressed polynucleotide coding for a MetC cystathionine beta-lyase (EC 4.4.1.8),
v) overexpressed polynucleotide coding for a MetE B12-independent homocysteine S-methyltransferase (EC 2.1.1.14),
w) overexpressed polynucleotide coding for a MetH B12-dependent homocysteine S-methyltransferase (EC 2.1.1.13),
x) overexpressed polynucleotide coding for a MetF methylene tetrahydrofolate reductase (EC 1.5.1.20),
y) overexpressed polynucleotide coding for an RDL2 thiosulphate sulphurtransferase (EC 2.8.1.1).

Very particularly preferred features are selected here from the group consisting of:
a) overexpressed polynucleotide coding for a ThrA aspartokinase I and homoserine dehydrogenase I (EC 2.7.2.4, EC 1.1.1.3),
b) overexpressed polynucleotide coding for a CysE serine acetyltransferase (EC 2.3.1.30),
c) overexpressed polynucleotide coding for a LysC aspartate kinase (EC 2.7.2.4),
d) overexpressed polynucleotide coding for a Hom homoserine dehydrogenase (EC 1.1.1.3),
e) overexpressed polynucleotide coding for a MetX homoserine acetyltransferase (EC 2.3.1.31),
f) overexpressed polynucleotide coding for a MetA homoserine O-transsccucinylase (EC 2.3.1.46),
g) overexpressed polynucleotide coding for a MetB cystathionine gamma synthase (EC 2.5.1.48),
h) overexpressed polynucleotide coding for an AecD β-C—S-lyase (EC 4.4.1.8, also referred to as beta-lyase),
i) overexpressed polynucleotide coding for a MetC cystathionine beta-lyase (EC 4.4.1.8),
j) overexpressed polynucleotide coding for a MetE B12-independent homocysteine S-methyltransferase (EC 2.1.1.14),
k) overexpressed polynucleotide coding for a MetH B12-dependent homocysteine S-methyltransferase (EC 2.1.1.13),
l) overexpressed polynucleotide coding for a MetF methylene tetrahydrofolate reductase (EC 1.5.1.20),
m) overexpressed polynucleotide coding for an RDL2 thiosulphate sulphurtransferase (EC 2.8.1.1).

According to the invention, the term "overexpression", "enhancement" or "increased activity" describes the increase in intracellular enzymatic activity of one or more enzymes in a microorganism, which are encoded by the corresponding DNA.

The enzymatic activity can be increased in principle, for example, by increasing the copy number of the gene sequence or gene sequences coding for the enzyme, by using a strong promoter or by utilizing a gene or allele coding for a corresponding enzyme having increased activity, and by combining these measures, where appropriate. For example, cells that are genetically modified according to the invention are generated by transformation, transduction, conjugation, or a combination of these methods, with a vector comprising the desired gene, an allele of said gene or parts thereof, and a vector enabling said gene to be expressed. Heterologous expression is achieved in particular by integrating the gene or the alleles into the chromosome of the cell or a vector replicating extrachromosomally.

An overview of the possibilities of increasing the enzymatic activity in cells by the example of pyruvate carboxylase is given in DE-A-100 31 999 which is incorporated herewith by reference and the disclosure content of which with respect to the possibilities of increasing the enzymatic activity in cells forms a part of the disclosure of the present invention.

The increase in enzymatic activity can be achieved, for example, by increasing the copy number of the corresponding polynucleotides chromosomally or extrachromosomally by at least one copy.

A widely used method for increasing the copy number comprises incorporating the corresponding polynucleotide into a vector, preferably a plasmid, which is replicated by a bacterium.

Examples of suitable plasmid vectors for Enterobacteriaceae are cloning vectors derived from pACYC184 (Bartolomé et al.; Gene 102: 75-78 (1991)), pTrc99A (Amann et al.; Gene 69: 301-315 (1988)) or pSC101 derivatives (Vocke and Bastia; Proceedings of the National Academy of Sciences USA 80(21): 6557-6561 (1983)) may be used. Plasmids derived from pCL1920 (Lerner, C. G. and Inouye, M., Nucl. Acids Res. (1990) 18:4631 [PMID: 2201955]) are also particularly suitable. Plasmid vectors derived from bacterial artificial chromosomes (BACs), such as for example pCC1BAC (EPICENTRE Biotechnologies, Madison, USA), are likewise suitable for increasing the copy number of the corresponding polynucleotides in *E. coli*.

Furthermore, transposons, insertion elements (IS elements) or phages may be employed as vectors. Such genetic systems are described, for example, in the patent specifications U.S. Pat. No. 4,822,738, U.S. Pat. No. 5,804,414 and U.S. Pat. No. 5,804,414. The IS element ISaB1 described in WO 92/02627 or the Tn 45 transposon of plasmid pXZ10142 (referred to in the "Handbook of *Corynebacterium glutamicum*" (editors: L. Eggeling and M. Bott)) may be used in the same manner.

Another widespread method for achieving overexpression is the process of chromosomal gene amplification. In this method, at least one additional copy of the polynucleotide of interest is inserted into the chromosome of a bacterium. Such amplification methods are described, for example, in WO 03/014330 or WO 03/040373.

A further method for achieving overexpression comprises linking the respective gene or allele in a functional manner (operably linked) to a promoter or an expression cassette. Known examples of suitable promoters for *E. coli* are the promoters T3, T7, SP6, M13, lac, tac and trc described by Amann et al. (Gene 69(2), 301-315 (1988)) and Amann and Brosius (Gene 40(2-3), 183-190 (1985)). Such a promoter can be inserted, for example, upstream of the gene in question, typically at a distance of approximately 1-500 nucleobases from the start codon. U.S. Pat. No. 5,939,307 reports that incorporation of expression cassettes or promoters such as, for example, tac promoter, trp promoter, lpp promoter or phage λ PL and PR promoters, for example upstream of the chromosomal threonine operon, was able to achieve an increase in expression. The promoters of phage T7, the gear-box promoters, the nar promoter or the promoters of the genes rrsG, rnpB, csrA, csrB, ompA, fusA, pepQ, rplX or rpsG may be used in the same manner. Such expression cassettes or promoters may also be used for overexpressing plasmid-bound genes, as described in EP 0 593 792. By using the lacIQ altele it is in turn possible to control expression of plasmid-bound genes (Glascock and Weickert, Gene 223, 221-231 (1998)). It is furthermore possible for the activity of the promoters to be increased due to modification of their sequence by means of one or more nucleotide substitutions, by insertion(s) and/or deletion(s).

If the increase in enzyme activity is effected by mutation of the endogenous gene, such mutations may be generated either by conventional methods in a non-targeted manner, for example by UV irradiation or by mutation-inducing chemicals, or in a targeted manner by means of genetic engineering methods such as deletion(s), insertion(s) and/or nucleotide substitution(s). Said mutations produce genetically modified cells. Particularly preferred mutant enzymes are in particular also those enzymes which can no longer be feedback-inhibited, or at least have reduced feedback inhibition compared to the wild-type enzyme.

If the increase in enzyme activity is effected by increasing expression of an enzyme, the copy number of the corresponding genes is increased, for example, or the promoter and regulatory regions or the ribosome binding site upstream of the structural gene are mutated. Expression cassettes incorporated upstream of the structural gene act in the same manner. Inducible promoters additionally enable expression to be increased at any time. Furthermore, however, so-called "enhancers" may also be assigned to the gene as regulatory sequences which likewise cause increased gene expression by an improved interaction between RNA polymerase and DNA. Measures of extending the mRNA life likewise improve expression. Furthermore, the enzyme activity is likewise enhanced by preventing degradation of the enzyme protein. In this context, the genes or gene constructs are either present in plasmids having different copy numbers or are integrated in the chromosome and amplified. Alternatively, overexpression of the genes in question can furthermore be achieved by modifying the media composition and culturing procedure. Instructions on this can be found by a person skilled in the art inter alia in Martin et al. (Bio/Technology 5, 137-146 (1987)), in Guerrero et al. (Gene 138, 35-41 (1994)), Tsuchiya and Morinaga (Bio/Technology 6, 428-430 (1988)), in Eikmanns et al. (Gene 102, 93-98 (1991)), in EP-A-0 472 869, in U.S. Pat. No. 4,601,893, in Schwarzer and Pühler (Bio/Technology 9, 84-87 (1991)), in Reinscheid et al. (Applied and Environmental Microbiology 60, 126-132 (1994)), in LaBarre et al. (Journal of Bacteriology 175, 1001-1007 (1993)), in WO-A-96/15246, in Malumbres et al. (Gene 134, 15-24 (1993)), in JP-A-10-229891, in Jensen and Hammer (Biotechnology and Bioengineering 58, 191-195 (1998)) and in known textbooks of genetics and molecular biology. The measures described above, like the mutations, result in genetically modified cells.

Also suitable are furthermore those plasmid vectors with the aid of which the process of gene amplification by integration into the chromosome can be applied. After homologous recombination by means of a cross-over event, the resulting strain contains at least two copies of the gene in question. A process for $E.$ $coli$ is described, for example, in Link, A. J., Phillips, D. and Church, G. M. (1997), J. Bacteriology 179: 6228-6237.

Recombinase-mediated processes, for example as described by Datsenko K A, Wanner B L., 2000, Proc Natl Acad Sci USA., 97(12):6640-5, may also be used for inserting or deleting DNA in the chromosome.

The wording "increased activity of an enzyme over its wild-type strain or starting strain" used above and in the following explanation means preferably always activity of the particular enzyme which has been increased by a factor of at least 2, particularly preferably of at least 10, additionally preferably of at least 100, additionally still more preferably of at least 1,000 and most preferably of at least 10,000. The cell according to the invention which has "increased activity of an enzyme over its wild-type strain or starting strain" furthermore also includes in particular a cell whose wild-type or starting strain has no or at least no detectable activity of said enzyme and which shows detectable activity of this enzyme only after increasing the enzyme activity, for example by overexpression. In this connection, the term "overexpression" or the wording "increase in expression" used in the following explanation also includes the case in which a starting cell, for example a wild-type cell, has no or at least no detectable expression and detectable expression of the enzyme is induced only by recombinant processes.

Methods of determining the enzymatic activity of various enzymes can be found in the literature.

Expression of the above-mentioned enzymes or genes can be detected with the aid of 1- and 2-dimensional protein gel fractionation and subsequent optical identification of the protein concentration in the gel, using appropriate evaluation software. If the increase in enzyme activity is based exclusively on an increase in expression of the corresponding gene, the increase in enzyme activity can be quantified in a simple manner by comparing the 1- or 2-dimensional protein fractionations between wild type and genetically modified cell. A customary method of preparing the protein gels in the case of bacteria and of identifying the proteins is the procedure described by Hermann et al. (Electrophoresis, 22: 1712.23 (2001)). The protein concentration can likewise be analysed by Western blot hybridization with an antibody specific for the protein to be detected (Sambrook et al., Molecular Cloning: a laboratory manual, 2nd ed. Cold Spring Harbor Laboratory Press, Cold Spring Harbor, N.Y. USA, 1989) and subsequent optical evaluation using appropriate software for concentration measurement (Lohaus and Meyer (1989) Biospektrum, 5: 32-39; Lottspeich (1999), Angewandte Chemie 111: 2630-2647). The activity of DNA-binding proteins can be measured by means of DNA band shift assays (also referred to as gel retardation) (Wilson et al. (2001) Journal of Bacteriology, 183: 2151-2155). The action of DNA-binding proteins on expression of other genes can be detected by various well-described reporter gene assay methods (Sambrook et al., Molecular Cloning: a laboratory manual, 2nd ed. Cold Spring Harbor Laboratory Press, Cold Spring Harbor, N.Y. USA, 1989). The intracellular enzymatic activities can be determined by various methods which have been described (Donahue et al. (2000) Journal of Bacteriology 182 (19): 5624-5627; Ray et al. (2000) Journal of Bacteriology 182 (8): 2277-2284; Freedberg et al. (1973) Journal of Bacteriology 115 (3): 816-823). If in the following explanation no specific methods for determining the activity of a particular enzyme are indicated, the increase in enzyme activity and also the reduction in enzyme activity are preferably determined by means of the methods described in Hermann et al., Electophoresis, 22: 1712-23 (2001), Lohaus et al., Biospektrum 5 32-39 (1998), Lottspeich, Angewandte Chemie 111: 2630-2647 (1999) and Wilson et al., Journal of Bacteriology 183: 2151-2155 (2001).

It may furthermore be advantageous for the production of L-amino acids, in particular L-methionine, to eliminate undesired secondary reactions (Nakayama: "Breeding of Amino Acid Producing Microorganisms", in: Overproduction of Microbial Products, Krumphanzl, Sikyta, Vanek (eds.), Academic Press, London, UK, 1982).

Thus, for improving the production of L-methionine in *E. coli*, it may be expedient to attenuate, optionally eliminate, one or more of the genes, or to reduce expression, selected from the group consisting of:

a) a metJ gene coding for the transcriptional regulator of L-methionine biosynthesis (MetJ) (b3938, ECK3930),
b) a pgi gene coding for glucose-6-phosphate isomerase (Pgi, EC No. 5.3.1.9) (b4025, ECK4017),
c) a thrB gene coding for homoserine kinase (ThrB, EC 2.7.1.39) (b0003, ECK0003),
d) a metK gene coding for S-adenosylmethionine synthase (MetK, EC No. 2.5.1.6) (b2942, ECK2937),
e) a dapA gene coding for dihydrodipicolinate synthase (DapA, EC No. 4.2.1.52) (b2478, ECK2474),
f) a pck gene coding for phosphoenolpyruvate carboxykinase (Pck, EC No. 4.1.1.49) (b3403, ECK3390),
g) a purU gene coding for formyltetrahydrofolate hydrolase (PurU, EC No. 3.5.1.10) (b1232, ECK1227),
h) a pykA gene coding for pyruvate kinase II (PykA, EC No. 2.7.1.40) (b1854, ECK1855)
i) a pykF gene coding for pyruvate kinase I (PykF, EC 2.7.1.40) (b1676, ECK1672),
j) a metQ gene coding for a subunit of the L-methionine transporter (MetQNI) (b0197, ECK0197),
k) a metI gene coding for a subunit of the L-methionine transporter (MetQNI) (b0198, ECK0198),
l) a metN gene coding for a subunit of the L-methionine transporter (MetQNI) (b0199, ECK0199),
m) a dcd gene coding for deoxycytidine-5'-triphosphate deaminase (Dcd, EC No. 3.5.4.13) (b2065, ECK2059),
n) a yncA gene coding for the putative N-acyltransferase (YncA, Metabolic Explorer WO2010/020681) (b1448, ECK1442),
o) an fnrS gene coding for the FnrS regulatory sRNA (b4699, ECK4511),
p) an rpoS gene coding for the RpoS sigma factor (b2741, ECK2736).

Particularly preferred features are selected here from the group consisting of:

a) a metJ gene coding for the transcriptional regulator of L-methionine biosynthesis (MetJ) (b3938, ECK3930),
b) a metK gene coding for S-adenosylmethionine synthase (MetK, EC No. 2.5.1.6) (b2942, ECK2937),
c) a pck gene coding for phosphoenolpyruvate carboxykinase (Pck, EC No. 4.1.1.49) (b3403, ECK3390),
d) a purU gene coding for formyltetrahydrofolate hydrolase (PurU, EC No. 3.5.1.10) (b1232, ECK1227),
e) a pykA gene coding for pyruvate kinase II (PykA, EC No. 2.7.1.40) (b1854, ECK1855)
f) a pykF gene coding for pyruvate kinase I (PykF, EC 2.7.1.40) (b1676, ECK1672),
g) a metQ gene coding for a subunit of the L-methionine transporter (MetQNI) (b0197, ECK0197),
h) a metI gene coding for a subunit of the L-methionine transporter (MetQNI) (b0198, ECK0198),
i) a metN gene coding for a subunit of the L-methionine transporter (MetQNI) (b0199, ECK0199),
j) a yncA gene coding for the putative N-acyltransferase (YncA, Metabolic Explorer WO2010/020681) (b1448, ECK1442),
k) an rpoS gene coding for the RpoS sigma factor (b2741, ECK2736).

Very particularly preferred features are selected here from the group consisting of:

a) a metJ gene coding for the transcriptional regulator of L-methionine biosynthesis (MetJ) (b3938, ECK3930),
b) a metK gene coding for S-adenosylmethionine synthase (MetK, EC No. 2.5.1.6) (b2942, ECK2937),
c) a metQ gene coding for a subunit of the L-methionine transporter (MetQNI) (b0197, ECK0197),
d) a metI gene coding for a subunit of the L-methionine transporter (MetQNI) (b0198, ECK0198),
e) a metN gene coding for a subunit of the L-methionine transporter (MetQNI) (b0199, ECK0199),
f) a yncA gene coding for the putative N-acyltransferase (YncA, Metabolic Explorer WO2010/020681) (b1448, ECK1442),
g) an rpoS gene coding for the RpoS sigma factor (b2741, ECK2736).

Where appropriate, the measures of attenuation are carried out in addition to or suitably combined with the measures indicated of enhancing genes for increasing methionine production.

According to the invention, microorganisms producing L-amino acid prior to the measure according to the invention do not include the wild-type strains and frequently used laboratory strains such as, inter alia, DH5α, DH5αmcr, W3110, MG1655, MC4100, Y1089, H560, BL21 and MM152.

However, the L-amino acid producing microorganisms may have been derived from said wild-type strains and frequently used laboratory strains.

Thus, the starting strain of the microorganism is preferably derived from the group consisting of *Escherichia coli* MG1655, *Escherichia coli* W3110, *Escherichia coli* DH5α, *Escherichia coli* DH10B, *Escherichia coli* BW2952, *Escherichia coli* REL606.

An example of an L-methionine-excreting or -producing strain which is preferred according to the invention is the *E. coli* producer strain MG1655 ΔmetJ metA*11 Ptrc-metH Ptrc-metF PtrcF-cysPUWAM PtrcF-cysJIH ΔpykF ΔpykA Ptrc09-gcvTHP ΔpurU Ptrc36-ARNmst17-metF, harbouring the production plasmids pME101-thrA*1-cysE-Pgap-metA*11 and pCC1BAC-serB-glyA-serA-serC (WO2009/043803).

Another example of an L-methionine-excreting or -producing strain which is preferred according to the invention is the *E. coli* producer strain MG1655 ΔmetJ Ptrc-metH Ptrc-metF PtrcF-cysPUWAM PtrcF-cysJIH Ptrc09-gcvTHP, harbouring the production plasmid pME101-thrA*1-cysE-Pgap-metA*11.

The *E. coli* producer strain MG1655ΔmetJ Ptrc-metH Ptrc-metF PtrcF-cysPUWAM PtrcF-cysJIH Ptrc09-gcvTHP may be cloned by a series of P1 transductions and curings, as described in the patent application WO2009/043803. The strain is based on the *E. coli* K12 MG1655 wild-type strain. The following modifications were introduced into the genome of this strain:

The metJ gene for the repressor of L-methionine biosynthesis was deleted.

The strong trc promoter was inserted upstream of the metH gene (codes for the cobalamin-dependent methionine synthase).

The strong trc promoter was inserted upstream of the metF gene (codes for 5,10-methylenetetrahydrofolate reductase).

The strong trcF promoter was inserted upstream of the cysPUWAM operon. cysPUWA codes for a sulphate/thiosulphate uptake transporter. cysM codes for cysteine synthase B.

The strong trcF promoter was inserted upstream of the cysJIH operon. cysJI codes for sulphite reductase and cysH codes for 3'-phosphoadenylyl-sulphate reductase.

The strong trc09 promoter was inserted upstream of the gcvTHP operon. gcvT, gcvH and gcvP code for three components of the glycine cleavage system.

Cloning of the *E. coli* production plasmid pME101-thrA*1-cysE-Pgap-metA*11 is described in the patent applications WO2007/077041 and WO2009/043803. The plasmid is one with a low copy number (low copy plasmid) based on the pCL1920 vector (Lerner, C. G. and Inouye, M., Nucl. Acids Res. (1990) 18:4631 [PMID: 2201955]). The empty plasmid, pME101, possesses the lacI$^q$ gene which codes for a strongly expressed allele of the lac repressor. The thrA*1 gene was cloned downstream of a strong trc promoter which can be repressed by the Lac repressor. It codes for a feedback-resistant variant of the *E. coli* ThrA aspartate kinase/homoserine dehydrogenase. Downstream, in the same orientation, is the cysE gene together with its natural promoter. It codes for the *E. coli* serine acetyltransferase. cysE is followed downstream by the strong *E. coli* gapA promoter which controls expression of the metA*11 gene. metA*11 codes for a feedback-resistant variant of the *E. coli* homoserine O-succinyltransferase.

Examples of other L-methionine-excreting or -producing microorganisms which are preferred according to the invention which may be mentioned are the following strains:

*E. coli* TF4076BJF metA#10+metYX(Lm) (WO2008/127240; page 46);

*E. coli* W3110ΔJ/pKP451 (EP 1 445 310 B1, page 7, example 4);

*E. coli* WΔthrBCΔmetJmetK32 pMWPthrmetA4Δ5Δ9 (Yoshihiro Usuda and Osamu Kurahashi, 2005, Applied and Environmental Microbiology, Vol. 71, NO: 6, pp. 3228-3234);

W3110/pHC34 (WO01/27307 page 13, example 3);

*E. coli* ECM2 (EP2205754A2, EP2326724A1 and EP12156052.8).

Further examples of various suitable microorganisms are described in Gomes et al. (Enzyme and Microbial Technology 37 (2005), 3-18).

The nucleotide sequences of the genes or open reading frames (ORFs) of *Escherichia coli* belong to the prior art and can be found in the *Escherichia coli* genomic sequence published by Blattner et al. (Science 277: 1453-1462 (1997)). Enzymes endogenous to the host (methionine aminopeptidase) are known to be able to remove the N-terminal amino acid methionine.

More detailed explanations for the terms of genetics and molecular biology are found in known textbooks of genetics and molecular biology such as, for example, the textbook of Birge (Bacterial and Bacteriophage Genetics, 4$^{th}$ ed., Springer Verlag, New York (USA), 2000) or the textbook of Berg, Tymoczko and Stryer (Biochemistry, 5$^{th}$ ed., Freeman and Company, New York (USA), 2002) or the handbook of Sambrook et al. (Molecular Cloning, A Laboratory Manual, (3-volume set), Cold Spring Harbor Laboratory Press, Cold Spring Harbor (USA), 2001).

The term "gene" here means a section on the deoxyribonucleic acid (DNA), which includes the information for producing (transcription) first a ribonucleic acid (RNA) which includes the information for producing (translation) a protein (polypeptide), in this case a polypeptide having the activity of a (p)ppGpp synthetase II. The fact that a gene or a polynucleotide includes the information for producing a protein is also referred to as encoding of a protein or polypeptide by the gene or by the RNA. Endogenous genes and polynucleotides mean the open reading frames (ORFs), genes or alleles and their polynucleotides, respectively, present in the population of a species. The terms "gene" and "ORF" (open reading frame) are used synonymously in the present invention.

The term "polynucleotide" refers generally to polyribonucleotides and polydeoxyribonucleotides, which may be nonmodified RNA or DNA or modified RNA or DNA.

The term "polypeptide" denotes peptides or proteins containing two or more amino acids connected via peptide bonds. The terms polypeptide and protein are used synonymously. Proteins are among the basic building blocks of all cells. They not only give the cell structure but are the molecular "machines" which transport substances, catalyse chemical reactions and recognize signalling agents.

"Proteinogenic amino acids" mean the amino acids which are found in natural proteins, that is to say in proteins of microorganisms, plants, animals and humans. They include more particularly L-amino acids selected from the group consisting of L-aspartic acid, L-asparagine, L-threonine, L-serine, L-glutamic acid, L-glutamine, glycine, L-alanine, L-cysteine, L-valine, L-methionine, L-isoleucine, L-leucine, L-tyrosine, L-phenylalanine, L-histidine, L-lysine, L-tryptophan, L-proline and L-arginine, and also selenocysteine. The proteinogenic amino acids are always α-amino acids. The α-carbon atom is asymmetric for all proteinogenic amino acids (they are chiral molecules), apart from the amino acid glycine: there exist two enantiomers of each of these amino acids. Only one of the two enantiomers is proteinogenic which is the L-amino acid: the apparatus required for synthesizing proteins—the ribosome, the tRNA, the aminoacyl-tRNA synthetase (which charges the tRNA with amino acids) and others—are themselves chiral as well and can recognize only the L-variant.

The term "gene expression" ("expression" in short) generally refers to the manifestation of the genetic information by way of a phenotype. In a narrower sense, gene expression refers to the transcription of a gene into an RNA, the subsequent translation of the RNA into a polypeptide which may have enzymatic activity.

A "starting strain" (parent strain) means the microorganism strain which is subjected to measures of increasing the productivity of one or more amino acids, peptides or proteins, or to measures of increasing the activity of one or more enzymes (for example a measure leading to overexpression). A starting strain may be a wild-type strain or else a strain which has been modified previously (for example a microorganism producing L-amino acids (producer strain)).

A "wild type" of a cell preferably refers to a cell whose genome is in a state as developed naturally by evolution. The term is used both for the entire cell and for individual genes. The term "wild type" in particular therefore does not include those cells or those genes, the gene sequences of which have been modified, at least partially, by humans by means of recombinant processes.

The present invention will be explained in more detail hereinbelow on the basis of exemplary embodiments.

Minimal (M9) and complete (LB) media used for *Escherichia coli* have been described by J. H. Miller (A Short Course in Bacterial Genetics (1992), Cold Spring Harbor Laboratory Press). Unless described otherwise, isolation of plasmid DNA from *Escherichia coli* and all techniques regarding restriction, ligation, Klenow treatment and alkaline phosphatase treatment are carried out according to Sambrook et al. (Molecular Cloning—A Laboratory Manual (1989) Cold Spring Harbor Laboratory Press). Unless described otherwise, transformation of *Escherichia coli* is carried out according to Chung et al. (Proceedings of the National Academy of Sciences of the United States of America 86: 2172-2175 (1989)).

Unless described otherwise, the incubation temperature for producing strains and transformants is 37° C.

Example 1

Screening of L-Methionine-Tolerant Mutants

The L-methionine-producing *E. coli* strain ECM2 is based on the K12 wild-type strain MG1655. As described in EP2205754A2, EP2326724A1 and EP12156052.8, the ECM2 strain harbours a feedback-resistant metA allele, a deletion of the genes metJ, yncA, pykA and pykF, a variant of the spoT gene, and a promoter enhancement upstream of each of the genes metH, metF, gcvT, cysP and cysJ.

1.1 Cloning of the serC Gene into Plasmid pUC18

The serC gene from *Escherichia coli* MG1655 was amplified with the aid of polymerase chain reaction (PCR) and then cloned into the pUC18 plasmid (Fermentas GmbH, St. LeonRot, Germany).

The PCR primers serCF(XbaI) and serCR(HindIII) have at their 5' ends in each case 6 random nucleotides followed by recognition sequences for the restriction endonucleases XbaI (TCTAGA) and HindIII (AAGCTT), respectively. Nucleotides 13 to 38 of serCF(XbaI) bind in the *E. coli* MG1655 genome from positions 956619 to 956644. Nucleotides 13 to 37 of serCR(HindIII) bind in the *E. coli* MG1655 genome from positions 958028 to 958004.

```
serCF(XbaI)
                                    (SEQ ID NO: 25)
5' AGGTGCTCTAGAGTCCGCGCTGTGCAAATCCAGAATGG 3' serCR(HindIII)
                                    (SEQ ID NO: 26)
5' TACACCAAGCTTAACTCTCTACAACAGAAATAAAAAC 3'
```

The serC gene was amplified using polymerase chain reaction (PCR) with primers serCF(XbaI) and serCR(HindIII) and with Phusion DNA polymerase (Finnzymes Oy, Espoo, Finland). Genomic DNA of *E. coli* MG1655 served as template. The resulting DNA fragment was 1434 bp in size. It was cleaved by the XbaI and HindIII restriction endonucleases and purified with the aid of a QIAquick PCR purification kit (Qiagen, Hilden, Germany). Non-methylated pUC18 plasmid DNA was cleaved by the XbaI and HindIII restriction endonucleases and purified with the aid of a QIAquick PCR purification kit (Qiagen, Hilden, Germany). The cleaved plasmid was then ligated with the PCR product and transformed into *E. coli* DH5α. Plasmid clones containing the serC gene were identified by restriction cleavage and DNA sequencing. The resulting plasmid was referred to as pUC18-serC.

1.2 Cloning of the serA Gene into the pUC18-serC Plasmid

The serA gene from *Escherichia coli* MG1655 was amplified with the aid of polymerase chain reaction (PCR) and then cloned into the pUC18-serC plasmid.

The PCR primer serAF(XbaI) has at its 5' end 6 random nucleotides followed by a recognition sequence for the XbaI restriction endonuclease (TCTAGA). Nucleotides 12 to 33 bind in the *E. coli* MG1655 genome from positions 3055199 to 3055220. The PCR primer serAR(SHSSNB) has at its 5' end 6 random nucleotides followed by recognition sequences for the restriction endonucleases SacI, HindIII, SphI, SmaI, NotI and BglII. Nucleotides 49 to 58 bind in the *E. coli* MG1655 genome from positions 3056880 to 3056861.

```
serAF(XbaI)
                                    (SEQ ID NO: 27)
5' CTGTAGTCTAGATTAGTACAGCAGACGGGCGCG 3' serAR(SHSSNB)
                                    (SEQ ID NO: 28)
5' CAAGAGCTCAAGCTTGCATGCGATTCCCGGGCGGCCGCAATAA
GATCTCCGTCAGGGCGTGGTGACCG 3'
```

The serA gene was amplified using polymerase chain reaction (PCR) with primers serAF(XbaI) and serAR (SHSSNB) and with Phusion DNA polymerase (Finnzymes Oy, Espoo, Finland). Genomic DNA of *E. coli* MG1655 served as template. The resulting DNA fragment was 1731 bp in size.

It was cleaved by the XbaI and SacI restriction endonucleases and purified with the aid of a QIAquick PCR purification kit (Qiagen, Hilden, Germany). The pUC18-serC plasmid was likewise cleaved by the XbaI and SacI restriction endonucleases and purified with the aid of a QIAquick PCR purification kit (Qiagen, Hilden, Germany). The cleaved plasmid was then ligated with the PCR product and transformed into *E. coli* DH5α. Plasmid clones containing the serA gene were identified by restriction cleavage and DNA sequencing. The resulting plasmid was referred to as pUC18-serAC.

1.3 Cloning of the serB Gene into the pUC18-serAC Plasmid

The serB gene from *Escherichia coli* MG1655 was amplified with the aid of polymerase chain reaction (PCR) and then cloned into the pUC18-serAC plasmid.

The PCR primer serB(SphI) has at its 5' end 6 random nucleotides followed by a recognition sequence for the SphI restriction endonuclease (GCATGC). Nucleotides 13 to 34 bind in the *E. coli* MG1655 genome from positions 4622816 to 4622837.

The PCR primer serB(SmaI) has at its 5' end 6 random nucleotides followed by recognition sequences for the restriction endonucleases SalI (GTCGAC) and SmaI (CCCGGG). Nucleotides 54 to 75 bind in the *E. coli* MG1655 genome from positions 4623887 to 4623866.

```
serB(SphI)
                                    (SEQ ID NO: 29)
5' CCATGCGCATGCCCACCCTTTGAAAATTTGAGAC 3' serB(SmaI)
                                    (SEQ ID NO: 30)
5' CCGCATGTCGACATCCCGGGGCAGAAAGGCCCACCCGAAGGTGAG
CCAGTGTGATTACTTCTGATTCAGGCTGCC 3'
```

The serB gene was amplified using polymerase chain reaction (PCR) with primers serB(SphI) and serB(SmaI) and with Phusion DNA polymerase (Finnzymes Oy, Espoo, Finland). Genomic DNA of *E. coli* MG1655 served as template. The resulting DNA fragment was 1137 bp in size.

It was cleaved by the SphI and SmaI restriction endonucleases and purified with the aid of a QIAquick PCR purification kit (Qiagen, Hilden, Germany). The pUC18-serAC plasmid was likewise cleaved by the SphI and SmaI restriction endonucleases, dephosphorylated by alkaline phosphatase and purified with the aid of a QIAquick PCR purification kit (Qiagen, Hilden, Germany). The cleaved plasmid was then ligated with the PCR product and transformed into *E. coli* DH5α. Plasmid clones containing the serB gene were identified by restriction cleavage and DNA sequencing. The resulting plasmid was referred to as pUC18-serBAC.

1.4 Cloning of the glyA Gene into the pUC18-serBAC Plasmid

The glyA gene from *Escherichia coli* MG1655 was amplified with the aid of polymerase chain reaction (PCR) and then cloned into the pUC18-serBAC plasmid.

The PCR primer glyA-downstream has at its 5' end 6 random nucleotides followed by a recognition sequence for the BglII restriction endonuclease (AGATCT). Nucleotides 13 to 35 bind in the *E. coli* MG1655 genome from positions 2682063 to 2682085.

The PCR primer glyA-upstream has at its 5' end 6 random nucleotides followed by recognition sequences for the NotI restriction endonuclease (GCGGCCGC). Nucleotides 15 to 33 bind in the *E. coli* MG1655 genome from positions 2683762 to 2683744.

```
glyA-downstream
                                      (SEQ ID NO: 31)
5' ATCTAAAGATCTGTTACGACAGATTTGATGGCGCG 3' glyA-upstream
                                      (SEQ ID NO: 32)
5' TTCATCGCGGCCGCGAAAGAATGTGATGAAGTG 3'
```

The glyA gene was amplified using polymerase chain reaction (PCR) with primers glyA-downstream and glyA-upstream and with Phusion DNA polymerase (Finnzymes Oy, Espoo, Finland). Genomic DNA of *E. coli* MG1655 served as template. The resulting DNA fragment was 1726 bp in size.

It was cleaved by the BglII and NotI restriction endonucleases and purified with the aid of a QIAquick PCR purification kit (Qiagen, Hilden, Germany). The pUC18-serBAC plasmid was likewise cleaved by the BglII and NotI restriction endonucleases and purified with the aid of a QIAquick PCR purification kit (Qiagen, Hilden, Germany). The cleaved plasmid was then ligated with the PCR product and transformed into *E. coli* DH5α. Plasmid clones containing the glyA gene were identified by restriction cleavage and DNA sequencing. The resulting plasmid was referred to as pUC18-serB-glyA-serAC.

1.5 Cloning of the Genes serB-glyA-serAC from pUC18-serB-glyA-serAC to pCC1-BAC

The pUC18-serB-glyA-serAC plasmid was cleaved by the HindIII restriction endonuclease, and the DNA fragments were fractionated by agarose gel electrophoresis. A 5.9 kb DNA fragment containing the genes serB, glyA, serA and serC was isolated from the gel. The fragment was ligated with the plasmid pCC1BAC Cloning-Ready Vector (Hind III) from Epicentre/Madison, USA), which had already been cleaved by HindIII, and transformed to *E. coli* EPI300. Plasmid clones containing the DNA fragment comprising serB, glyA, serA and serC were identified by restriction cleavage and DNA sequencing. The resulting production plasmid was referred to as pCC3.

1.6 Cloning of the pME-RDL2a Production Plasmid

The pME-RDL2a production plasmid was cloned as described in EP application 11151526.8. It includes the *Escherichia coli* cysE gene, feedback-resistant alleles of the *Escherichia coli* thrA and metA genes, and the RDL2a gene coding for the *Saccharomyces cerevisiae* RDL2p thiosulphate sulphurtransferase. It additionally includes a streptomycin-resistance gene.

1.7 Transformation of Strain ECM2 with the Production Plasmids

The ECM2 strain was transformed with the pCC3 production plasmid of Example 1.5, and transformants were selected with 20 mg/l chloramphenicol. The cells were then transformed with the pME-RDL2a plasmid of Example 1.6 and the resulting transformants were selected with 20 mg/l chloramphenicol+100 mg/l streptomycin. The resulting strain was referred to as ECM2/pCC3/pME-RDL2a.

1.8 Screening and Sequencing of L-Methionine-Tolerant Mutants

L-methionine-tolerant mutants were selected by plating a preculture of the ECM2/pCC3/pME-RDL2a strain on PC1 minimal medium plates (Table 1, with 14 g/l agar) containing 75 g/l L-methionine (Merck, Frankfurt, Germany). The preculture comprised 10 ml of preculture medium (10% LB medium containing 2.5 g/l glucose and 90% PC1 minimal medium) inoculated with 100 µl of cell culture and was cultured at 37° C. for 10 hours.

TABLE 1

| PC1 minimal medium | |
|---|---|
| Substance | Concentration |
| ZnSO4 * 7H2O | 4 mg/l |
| CuCl2 * 2H2O | 2 mg/l |
| MnSO4 * H2O | 20 mg/l |
| H3BO3 | 1 mg/l |
| Na2MoO4 * 2H2O | 0.4 mg/l |
| MgSO4 * 7H2O | 1 g/l |
| Citric acid * 1H2O | 6.56 g/l |
| CaCl2 * 2H2O | 40 mg/l |
| K2HPO4 | 8.02 g/l |
| Na2HPO4 | 2 g/l |
| (NH4)2HPO4 | 8 g/l |
| NH4Cl | 0.13 g/l |
| (NH4)2SO3 | 5.6 g/l |
| MOPS | 5 g/l |
| NaOH 10M | adjusted to pH 6.8 |
| FeSO4 * 7H2O | 40 mg/l |
| Thiamine hydrochloride | 10 mg/l |
| Vitamin B12 | 10 mg/l |
| Glucose | 10 g/l |
| Isopropyl-thio-β-galactoside (IPTG) | 2.4 mg/l |
| Spectinomycin | 50 mg/l |
| Chloramphenicol | 20 mg/l |

After 5 days of incubation, single colonies of L-methionine-tolerant mutants were isolated from the plates.

To prepare for sequencing, derivatives of the L-methionine-tolerant mutants of the ECM2/pCC3/pME-RDL2a strain that no longer contain the plasmids pCC3 and pME-RDL2a were isolated after propagation in antibiotics-free LB medium for approximately six generations. The strains obtained are streptomycin- and chloramphenicol-sensitive.

Chromosomal DNA was isolated from 8 mutants. This DNA was used for whole genome sequencing (GATC, Constance, Germany).

Compared to the ECM2 starting strain, only mutations were found in the proP gene. Table 2 below lists the mutations. The sequences of the proP alleles are shown in SEQ ID No: 9 to SEQ ID No: 24.

TABLE 2

| Strain | Mutation in proP gene | Type of mutation | Name of mutation |
|---|---|---|---|
| DM2321 | E412* | AA substitution | M8 (SEQ ID NO: 9-10) |
| DM2322 | Insertion of C downstream of nucleotide position 842 | Nucleotide insertion | M3 (SEQ ID NO: 11-12) |
| DM2323 | Deletion of A downstream of nucleotide position 854 | Nucleotide deletion | M4 (SEQ ID NO: 13-14) |
| DM2324 | Y467H | AA substitution | M11 (SEQ ID NO: 15-16) |
| DM2325 | Deletion of 51 bp from nucleotide position 1173 to 1223 | Nucleotide deletion | M7 (SEQ ID NO: 17-18) |
| DM2326 | 19 bp insertion downstream of nucleotide position 973 | Nucleotide insertion | M6 (SEQ ID NO: 19-20) |
| DM2327 | R324L | AA substitution | M5 (SEQ ID NO: 21-22) |
| DM2328 | 1359 bp insertion downstream of nucleotide position 183 | Nucleotide insertion | M2 (SEQ ID NO: 23-24) |

In accordance with the Budapest Treaty, strains DM2321, DM2322, DM2323, DM2324, DM2325, DM2326, DM2327 and DM2328 were deposited with the DSMZ (Deutsche Sammlung von Mikroorganismen and Zellkulturen GmbH, Inhoffenstraβe 7 B, 38124 Brunswick, Germany) under DSM numbers DSM 25095 (=DM2321), 25096 (=DM2322), 25097 (=DM2323), 25098 (=DM2324), 25099 (=DM2325), 25100 (=DM2326), 25101 (=DM2327), and 25102 (=DM2328) on 23 Aug. 2011.

Example 2

Detection of Activity of L-Methionine-Tolerant proP Mutants

ProP activity of the proP mutants was determined by analyzing by way of example proline uptake for strain DM2328 in comparison with the starting strain ECM2. For this, a 10 ml preculture 1 was incubated with shaking in LB medium at 37° C. over day. 1 ml of preculture was transferred to 20 ml of M9 medium as preculture 2 and cultured overnight. Preculture 2 was inoculated to an OD600 of 0.2 in 50 ml of fresh M9 medium. The cells were subsequently cultured for 3-4 h, then washed three times with ice-cold M9 buffer, adjusted to an OD600 of 2 and stored on ice.

Proline uptake was determined by means of radiolabelled [14C(U)]L-proline (specific activity: 1.85 MBq; Hartmann Analytic, Germany). For this, 2.3 ml of cell suspension were placed in each case in a stirred vessel and energized at 37° C. for 2 min by adding 10 mM glucose. Transport measurement was started with stirring by adding 20 μl of L-[14C]-proline at a concentration of 24.6 mM. At different points in time, (0, 15, 30, 45, 60, 75, 90, 105 and 120 s) 200 μl were removed in each case and pipetted on glass fibre filters (Millipore). The surrounding medium was removed by suction by means of a vacuum filtration manifold, and the cells were subsequently washed twice with 2.5 ml of 0.1 M LiCl solution. The filters were treated with 3.8 ml of scintillation fluid (Roth, Karlsruhe, Germany), and radioactivity was measured with the aid of a scintillation counter (LS 6500, Beckman Instruments, Munich, Germany). Total activity in the reaction mixture was determined by measuring a sample directly without filtration. Disintegration per minute (dpm) was measured for each sample. Uptake activity was calculated in nmol/min (mg of dry mass) (0.36=dry mass relation of E. coli [mg/ml OD=1]). The rate of transport in nmol/mg*min was derived from the linear portion of the uptake kinetics. Table 3 below indicates the averages of three parallel measurements.

TABLE 3

| Strain | Rate of L-proline transport (nmol/mg * min) |
|---|---|
| ECM2 | 2.39 |
| DM2328 | 1.27 |

Example 3

Transformation of Strains DM2321, DM2322, DM2323, DM2324, DM2325, DM2326, DM2327 and DM2328 with the Production Plasmids Strains DM2321, DM2322, DM2323, DM2324, DM2325, DM2326, DM2327 and DM2328 were transformed with the pCC3 production plasmid of Example 1.5, and transformants were selected with 20 mg/l chloramphenicol. The cells were then transformed with the pME-RDL2a plasmid of Example 1.6, and the resulting transformants were selected with 20 mg/l chloramphenicol and 100 mg/l streptomycin. The resulting strains were referred to as DM2321/pCC3/pME-RDL2a, DM2322/pCC3/pME-RDL2a, DM2323/pCC3/pME-RDL2a, DM2324/pCC3/pME-RDL2a, DM2325/pCC3/pME-RDL2a, DM2326/pCC3/pME-RDL2a, DM2327/pCC3/pME-RDL2a and DM2328/pCC3/pME-RDL2a.

Example 4

Performance Assay in a Shaker-Flask Experiment

Performance of the E. coli L-methionine producer strains was evaluated by production tests in 100 ml conical flasks. Precultures of in each case 10 ml of preculture medium (10% LB medium containing 2.5 g/l glucose and 90% PC1 minimal medium) inoculated with 100 µl of cell culture were cultured at 37° C. for 10 hours. These were then used to inoculate in each case 10 ml of PC1 minimal medium (see Table 1 in Example 1) to an OD 600 nm of 0.2 (Eppendorf Bio-Photometer; Eppendorf AG, Hamburg, Germany) and the cultures were cultured at 37° C. for 24 hours. The extracellular L-methionine concentration was determined by ion exchange chromatography and post-column derivatization with ninhydrin detection using an amino acid analyser (Sykam GmbH, Eresing, Germany). The extracellular glucose concentration was determined using a YSI 2700 Select Glucose Analyzer (YSI Life Sciences, Yellow Springs, Ohio, USA). The results are listed in Table 4. After 24 hours the glucose had been used up completely in both cultures.

TABLE 4

L-Methionine concentrations in the fermentation broths of the *E. coli* strains tested

| Strain | OD (600 nm) | L-Methionine (g/l) |
| --- | --- | --- |
| ECM2/pCC3/pME-RDL2a | 3.27 | 1.71 |
| DM2321/pCC3/pME-RDL2a | 3.04 | 1.83 |
| DM2322/pCC3/pME-RDL2a | 3.38 | 1.83 |
| DM2323/pCC3/pME-RDL2a | 3.20 | 1.83 |
| DM2324/pCC3/pME-RDL2a | 3.38 | 1.82 |
| DM2325/pCC3/pME-RDL2a | 3.44 | 1.83 |
| DM2326/pCC3/pME-RDL2a | 3.23 | 1.87 |
| DM2327/pCC3/pME-RDL2a | 3.22 | 1.99 |
| DM2328/pCC3/pME-RDL2a | 3.12 | 1.86 |

Example 5

Cloning of the M8, M4 and M6_proP Alleles into Plasmid pMAK705

The proP alleles M8 from DM2321, M4 from DM2323 and M6 from DM2326 were amplified with the aid of polymerase chain reaction (PCR) and then cloned into the pMAK705 plasmid.

A primer pair was designed based on the sequences obtained for the proP alleles (see Example 1), which enables in each case a fragment comprising the particular mutation to be amplified. Said fragment may then be cloned into the pMAK705 plasmid (Hamilton C M, Aldea M, Washburn B K, Babitzke P, Kushner S R (1989); J Bacteriol.; 171(9): 4617-4622).

The PCR primer proPmut1 (NotI) has at its 5' end 4 random nucleotides followed by the recognition sequence for the HindIII restriction endonuclease.

The PCR primer proPmut2 (BamHI) has at its 5' end 4 random nucleotides followed by the recognition sequence for the BamHI restriction endonuclease.

Nucleotides 13 to 32 of proPmut1 (NotI) bind from positions 4328800 to 4328819 in the *E. coli* MG1655 genome. Nucleotides 13 to 37 of proPmut2 (NotI) bind from positions 4330303 to 4330322 in the *E. coli* MG1655 genome.

```
proPmut1(HindIII)
                                        (SEQ ID NO: 33)
5' GTCAAAGCTT ATATGGTCGCCAGAAGATCC 3' proPmut2(BamHI)
                                        (SEQ ID NO: 34)
5' GTCAGGATCC TCAGCCGCATTACACAGTTG 3'
```

Genomic DNA of strains DM2321, DM2323 and DM2328 (see Example 1) served as template.

In each case, a fragment spanning the respective mutation in the proP gene was amplified using polymerase chain reaction (PCR) with Phusion DNA polymerase (Finnzymes Oy, Espoo, Finland). The fragment from DM2321 (harbours proP-M8), containing the E412* mutation, was 1564 bp in size (SEQ ID NO: 35). The fragment from DM2323 (harbours proP-M4), comprising a deletion of an "A" downstream of nucleotide position 854, was 1542 bp in size (SEQ ID NO: 36). The fragment from DM2326 (harbours proP-M6), containing a 19 bp insertion downstream of nucleotide position 973, was 1563 bp in size (SEQ ID NO: 37).

All 3 fragments were cleaved by the HindIII und BamHI restriction endonucleases and purified with the aid of a QIAquick PCR purification kit (Qiagen, Hilden, Germany). The fragments were then used for ligation with the pMAK705 plasmid.

The pMAK705 plasmid was cleaved by the HindIII und BamHI restriction endonucleases, dephosphorylated by alkaline phosphatase (Alkaline Phosphatase, Calf Intestinal, New England Biolabs, Frankfurt a.M., Germany) and purified via a QIAquick PCR purification kit (Qiagen, Hilden). The plasmid was then admixed with the particular proP fragments and ligated by means of Quick DNA ligase (New England BioLabs, Frankfurt, Germany). The ligation mixtures were transformed into *E. coli* DH5α (Grant et al.; Proceedings of the National Academy of Sciences USA, 87 (1990) 4645-4649). Correct plasmid clones were selected by 20 mg/l chloramphenicol and identified by restriction cleavage and subsequent sequencing of the inserts. The plasmids thus obtained were referred to as pMAK_proP-M4, pMAK_proP-M6 and pMAK_proP-M8. pMAK_proP-M8 is depicted by way of example in FIG. 3.

Example 6

Mutagenesis of the proP gene in *E. coli* strain ECM2

The chromosomal proP wild-type allele in the L-methionine-producing *E. coli* strain ECM2 (see Example 1) was replaced in each case by the proP alleles M4, M6 and M8 which mediate methionine resistance. For this purpose, the strain was transformed in each case by means of electroporation with plasmids pMAK_proP-M4, pMAK_proP-M6 and pMAK_proP-M8 (see Example 5). The pMAK plasmids have a chloramphenicol-resistance gene and a temperature-sensitive origin of replication. The plasmid is replicated by *E. coli* at 30° C., but not at 44° C. The transformation mixtures were plated in each case on LB agar containing 20 mg/l chloramphenicol and incubated at 30° C. for 40 hours. Cells were then removed using an inoculation loop, resuspended in LB medium and diluted 10000-fold in LB medium. 100 µl of the dilution were plated on LB agar containing 20 mg/l chloramphenicol and incubated at 44° C. for another 24 hours. As a result, colonies were selected in which the pMAK_proP-M4, pMAK_proP-M6 and pMAK_proP-M8 plasmids were chromosomally integrated in each case. In each case one of these colonies was thinned out on LB agar containing 20 mg/l chloramphenicol using an inoculation loop and incubated at 44° C. for 24 hours. The introduced mutations were detected by means of standard PCR methods (Innis et al. (1990) PCR Protocols. A guide to methods and applications, Academic Press) using the following primer pair (see Example 11):

```
proPmut1(HindIII)
                                               (SEQ ID NO: 33)
    5' GTCAAAGCTT ATATGGTCGCCAGAAGATCC 3' proPmut2(BamHI)
                                               (SEQ ID NO: 34)
    5' GTCAGGATCC TCAGCCGCATTACACAGTTG 3'
```

The PCR product resulting in each case was sequenced using both primers at GATC (Constance, Germany). All three proP alleles were transferred in each case into the *E. coli* strain ECM2, with the resulting strains being referred to as ECM2_proP-M4, ECM2_proP-M6 and ECM2_proP-M8.

Example 7

Transformation of Strains ECM2_proP-M4, ECM2_proP-M6 and ECM2_proP-M8 with the Production Plasmids The strains ECM2_M4, ECM2_-M6 and ECM2_proP-M8 were transformed with the pCC3 production plasmid of Example 1.5 and transformants were selected with 20 mg/l chloramphenicol. The cells were then transformed with the pME-RDL2a plasmid of Example 1.6 and the resulting transformants were selected with 20 mg/l chloramphenicol and 100 mg/l streptomycin. The resulting strains were referred to as ECM2_proP-M4/pCC3/pME-RDL2a, ECM2_proP-M6/pCC3/pME-RDL2a and ECM2_proP-M8/pCC3/pME-RDL2a.

Example 8

Performance Assay in a Shaker-Flask Experiment

Performance of the *E. coli* L-methionine producer strains ECM2_proP-M4/pCC3/pME-RDL2a, ECM2_proP-M6/pCC3/pME-RDL2a and ECM2_proP-M8/pCC3/pME-RDL2a was evaluated by production tests in 100 ml conical flasks. Precultures of in each case 10 ml of preculture medium (10% LB medium containing 2.5 g/l glucose and 90% PC1 minimal medium) inoculated with 100 μl of cell culture were cultured at 37° C. for 10 hours. These were then used to inoculate in each case 10 ml of PC1 minimal medium (see Table 1 in Example 1) to an OD 600 nm of 0.2 (Eppendorf Bio-Photometer; Eppendorf AG, Hamburg, Germany) and the cultures were cultured at 37° C. for 24 hours. The extracellular L-methionine concentration was determined by ion exchange chromatography and post-column derivatization with ninhydrin detection using an amino acid analyser (Sykam GmbH, Eresing, Germany). The extracellular glucose concentration was determined using a YSI 2700 Select Glucose Analyzer (YSI Life Sciences, Yellow Springs, Ohio, USA). The results are listed in Table 5. After 24 hours glucose had been used up completely in both cultures.

TABLE 5

L-Methionine concentrations in the fermentation broths of the *E. coli* strains tested

| Strain | OD (600 nm) | L-Methionine (g/l) |
|---|---|---|
| ECM2/pCC3/pME-RDL2a | 3.27 | 1.71 |
| ECM2_proP-M4/pCC3/pME-RDL2a | 3.38 | 1.83 |
| ECM2_proP-M6/pCC3/pME-RDL2a | 3.04 | 1.87 |
| ECM2_proP-M8/pCC3/pME-RDL2a | 3.22 | 1.83 |

---

The invention claimed is:

1. A process for the production of L-methionine or feed additive containing L-methionine comprising:
fermenting a microorganism of the Enterobacteriaceae family modified to attenuate expression of a "proton/compatible solute symporter gene (proP gene)" as compared to the parent strain of said microorganism in a medium.

2. The process of claim 1, wherein the attenuation comprises eliminating expression of the proP gene of the microorganism.

3. The process of claim 1, wherein expression of the proP gene of the microorganism is reduced compared to a parent strain of said microorganism, wherein expression of a proP gene of said parent strain is not attenuated.

4. The process of claim 1, wherein production of the L-methionine by the microorganism is increased compared to a parent strain of said microorganism, wherein expression of a proP gene of said parent strain is not attenuated.

5. The process of claim 1, wherein the L-methionine accumulates in the medium.

6. The process of claim 1, wherein the L-methionine accumulates in cells of the microorganism.

7. The process of claim 1, wherein the modification comprises increasing a methionine tolerance of the microorganism compared to a methionine tolerance of a parent strain of the microorganism, wherein expression of a proP gene of said parent strain is not attenuated.

8. The process of claim 1, wherein the microorganism of the Enterobacteriaceae family comprises a bacterium chosen from the genera *Escherichia*, *Erwinia*, *Providencia* and *Serratia*.

9. The process of claim 1, wherein the proP gene of said microorganism before attenuation comprises a polynucleotide having a sequence identity of at least 80% to the polynucleotide sequences of SEQ ID NO: 1, 3, 5 or 7.

10. The process of claim 1, wherein the proP gene of said microorganism is a polynucleotide which has a sequence identity of at least 80% to the sequence of the polynucleotide of SEQ ID NO: 1 and wherein the polynucleotide further comprises at least one mutation over the polynucleotide of SEQ ID NO: 1 chosen from:
   a. substitution of a triplet coding for L-arginine at a position corresponding to position 324 of SEQ ID NO: 2 by a triplet coding for an amino acid chosen from L-leucine, L-isoleucine and L-valine;
   b. substitution of a triplet coding for L-tyrosine at a position corresponding to position 467 of SEQ ID NO: 2 by a triplet coding for an amino acid chosen from L-lysine, L-arginine and L-histidine;
   c. substitution of a triplet coding for L-glutamic acid at a position corresponding to position 412 of SEQ ID NO: 2 by a triplet coding for a stop codon;
   d. deletion of a nucleobase adenine at a position corresponding to position 854 of the proP gene of SEQ ID NO: 1;
   e. deletion of one or more of the nucleobases from positions corresponding to position 1173 to position 1223 of the proP gene of SEQ ID NO: 1;
   f. insertion of a nucleobase cytosine at a position corresponding to position 842 of the proP gene of SEQ ID NO: 1;
   g. insertion of one or more nucleobase(s) at a position corresponding to position 973 of the proP gene of SEQ ID NO: 1; and
   h. insertion of one or more nucleobase(s) at a position corresponding to position 183 of the proP gene of SEQ ID NO: 1.

11. The process of claim 1, wherein the medium comprises an inorganic sulphur source.

12. The process of claim 1, further comprising
   a step chosen from isolating, collecting and/or purifying the L-methionine from a fermentation broth obtained from fermenting the microorganism in the medium, wherein the L-methionine accumulates in the fermentation broth during the fermenting the microorganism in the medium.

13. The process of claim 12, further comprising isolating and collecting other components from the fermentation broth and/or biomass of the microorganism.

* * * * *

SEQUENCE LISTING

```
<160> NUMBER OF SEQ ID NOS: 38

<210> SEQ ID NO 1
<211> LENGTH: 1503
<212> TYPE: DNA
<213> ORGANISM: Escherichia coli
<220> FEATURE:
<221> NAME/KEY: CDS
<222> LOCATION: (1)..(1503)
<223> OTHER INFORMATION: Kodierregion proP

<400> SEQUENCE: 1 atg ctg aaa agg aaa aaa gta aaa ccg att acc ctt cgt gat gtc acc      48
Met Leu Lys Arg Lys Lys Val Lys Pro Ile Thr Leu Arg Asp Val Thr
1               5                   10                  15 att att gat gac ggt aaa ctg cgt aaa gcc att acc gca gca tca ctg      96
Ile Ile Asp Asp Gly Lys Leu Arg Lys Ala Ile Thr Ala Ala Ser Leu
            20                  25                  30 ggt aat gca atg gaa tgg ttc gat ttt ggt gtt tat ggt ttt gtt gct     144
Gly Asn Ala Met Glu Trp Phe Asp Phe Gly Val Tyr Gly Phe Val Ala
        35                  40                  45 tac gca tta ggt aaa gtt ttt ttc ccg ggg gct gac ccc agc gtg cag     192
Tyr Ala Leu Gly Lys Val Phe Phe Pro Gly Ala Asp Pro Ser Val Gln
    50                  55                  60 atg gtt gct gca ctt gcc act ttc tcc gtt ccc ttt ctg att cga ccg     240
Met Val Ala Ala Leu Ala Thr Phe Ser Val Pro Phe Leu Ile Arg Pro
```

-continued

```
          65                   70                    75                   80
ctt ggc gga ctc ttc ttt ggt atg ttg ggc gat aaa tat ggt cgc cag        288
Leu Gly Gly Leu Phe Phe Gly Met Leu Gly Asp Lys Tyr Gly Arg Gln
                     85                    90                    95 aag atc ctc gct atc act att gtg att atg tcg atc agt acg ttc tgt        336
Lys Ile Leu Ala Ile Thr Ile Val Ile Met Ser Ile Ser Thr Phe Cys
            100                   105                   110 att ggc tta ata ccg tcc tac gac acg att ggt att tgg gca ccg att        384
Ile Gly Leu Ile Pro Ser Tyr Asp Thr Ile Gly Ile Trp Ala Pro Ile
            115                   120                   125 ctg ctg ttg atc tgt aag atg gca caa ggt ttc tcg gtc ggc ggt gaa        432
Leu Leu Leu Ile Cys Lys Met Ala Gln Gly Phe Ser Val Gly Gly Glu
        130                   135                   140 tat acc ggg gcg tcg ata ttt gtt gcg gaa tac tcc cct gac cgt aaa        480
Tyr Thr Gly Ala Ser Ile Phe Val Ala Glu Tyr Ser Pro Asp Arg Lys
145                   150                   155                   160 cgt ggc ttt atg ggc agc tgg ctg gac ttc ggt tct att gcc ggg ttt        528
Arg Gly Phe Met Gly Ser Trp Leu Asp Phe Gly Ser Ile Ala Gly Phe
                     165                   170                   175 gtg ctg ggt gcg ggc gtg gtg gtg tta att tcg acc att gtc ggc gaa        576
Val Leu Gly Ala Gly Val Val Val Leu Ile Ser Thr Ile Val Gly Glu
            180                   185                   190 gcg aac ttc ctc gat tgg ggc tgg cgt att ccg ttc ttt atc gct ctg        624
Ala Asn Phe Leu Asp Trp Gly Trp Arg Ile Pro Phe Phe Ile Ala Leu
            195                   200                   205 ccg tta ggg att atc ggg ctt tac ctg cgc cat gcg ctg gaa gag act        672
Pro Leu Gly Ile Ile Gly Leu Tyr Leu Arg His Ala Leu Glu Glu Thr
        210                   215                   220 ccg gcg ttc cag cag cat gtc gat aaa ctg gaa cag ggc gac cgt gaa        720
Pro Ala Phe Gln Gln His Val Asp Lys Leu Glu Gln Gly Asp Arg Glu
225                   230                   235                   240 ggt ttg cag gat ggc ccg aaa gtc tcg ttt aaa gag att gcc act aaa        768
Gly Leu Gln Asp Gly Pro Lys Val Ser Phe Lys Glu Ile Ala Thr Lys
                     245                   250                   255 tac tgg cgc agc ctg ttg aca tgt att ggt ctg gta att gcc acc aac        816
Tyr Trp Arg Ser Leu Leu Thr Cys Ile Gly Leu Val Ile Ala Thr Asn
            260                   265                   270 gtg act tac tac atg ttg ctg acc tat atg ccg agt tat ttg tcg cat        864
Val Thr Tyr Tyr Met Leu Leu Thr Tyr Met Pro Ser Tyr Leu Ser His
            275                   280                   285 aac ctg cat tac tcc gaa gac cac ggg gtg ctg att att atc gcc att        912
Asn Leu His Tyr Ser Glu Asp His Gly Val Leu Ile Ile Ile Ala Ile
        290                   295                   300 atg atc ggt atg ctg ttt gtc cag ccg gtg atg ggc ttg ctg agt gac        960
Met Ile Gly Met Leu Phe Val Gln Pro Val Met Gly Leu Leu Ser Asp
305                   310                   315                   320 cgt ttt ggc cgt cgt ccg ttt gtg cta ctt ggt agt gtt gcc ctg ttt       1008
Arg Phe Gly Arg Arg Pro Phe Val Leu Leu Gly Ser Val Ala Leu Phe
                     325                   330                   335 gtg ttg gcg atc ccg gcg ttt att ctg att aac agt aac gtc atc ggc       1056
Val Leu Ala Ile Pro Ala Phe Ile Leu Ile Asn Ser Asn Val Ile Gly
            340                   345                   350 ctg att ttt gcc ggg tta ctg atg ctg gcg gtg atc ctt aac tgc ttt       1104
Leu Ile Phe Ala Gly Leu Leu Met Leu Ala Val Ile Leu Asn Cys Phe
            355                   360                   365 acg ggc gtt atg gct tct acc ttg cca gcg atg ttc ccg acg cat atc       1152
Thr Gly Val Met Ala Ser Thr Leu Pro Ala Met Phe Pro Thr His Ile
        370                   375                   380 cgt tac agc gcg ctg gcg gcg gca ttt aat att tcg gtg ctg gtt gcc       1200
Arg Tyr Ser Ala Leu Ala Ala Ala Phe Asn Ile Ser Val Leu Val Ala
```

```
Arg Tyr Ser Ala Leu Ala Ala Phe Asn Ile Ser Val Leu Val Ala
385                 390                 395                 400 ggt ctg acg cca acg ctg gcg gcc tgg ctg gtc gaa agc tcg cag aat        1248
Gly Leu Thr Pro Thr Leu Ala Ala Trp Leu Val Glu Ser Ser Gln Asn
                405                 410                 415 ctg atg atg cct gcc tat tac ctg atg gta gtg gcg gtg gtt ggt tta        1296
Leu Met Met Pro Ala Tyr Tyr Leu Met Val Val Ala Val Val Gly Leu
            420                 425                 430 atc acc ggc gta acc atg aaa gag acg gca aat cgt ccg ttg aaa ggt        1344
Ile Thr Gly Val Thr Met Lys Glu Thr Ala Asn Arg Pro Leu Lys Gly
        435                 440                 445 gcg aca ccg gcg gcg tca gat ata cag gaa gcg aag gaa att ctc gtc        1392
Ala Thr Pro Ala Ala Ser Asp Ile Gln Glu Ala Lys Glu Ile Leu Val
    450                 455                 460 gag cat tac gat aat atc gag cag aaa atc gat gat att gac cac gag        1440
Glu His Tyr Asp Asn Ile Glu Gln Lys Ile Asp Asp Ile Asp His Glu
465                 470                 475                 480 att gcc gat ttg cag gcg aaa cgt acc cgc ctg gtg cag caa cat ccg        1488
Ile Ala Asp Leu Gln Ala Lys Arg Thr Arg Leu Val Gln Gln His Pro
                485                 490                 495 cga att gat gaa taa                                                     1503
Arg Ile Asp Glu
            500

<210> SEQ ID NO 2
<211> LENGTH: 500
<212> TYPE: PRT
<213> ORGANISM: Escherichia coli

<400> SEQUENCE: 2

Met Leu Lys Arg Lys Lys Val Lys Pro Ile Thr Leu Arg Asp Val Thr
1               5                   10                  15

Ile Ile Asp Asp Gly Lys Leu Arg Lys Ala Ile Thr Ala Ala Ser Leu
            20                  25                  30

Gly Asn Ala Met Glu Trp Phe Asp Phe Gly Val Tyr Gly Phe Val Ala
        35                  40                  45

Tyr Ala Leu Gly Lys Val Phe Phe Pro Gly Ala Asp Pro Ser Val Gln
    50                  55                  60

Met Val Ala Ala Leu Ala Thr Phe Ser Val Pro Phe Leu Ile Arg Pro
65              70                  75                  80

Leu Gly Gly Leu Phe Phe Gly Met Leu Gly Asp Lys Tyr Gly Arg Gln
            85                  90                  95

Lys Ile Leu Ala Ile Thr Ile Val Ile Met Ser Ile Ser Thr Phe Cys
        100                 105                 110

Ile Gly Leu Ile Pro Ser Tyr Asp Thr Ile Gly Ile Trp Ala Pro Ile
    115                 120                 125

Leu Leu Leu Ile Cys Lys Met Ala Gln Gly Phe Ser Val Gly Gly Glu
130                 135                 140

Tyr Thr Gly Ala Ser Ile Phe Val Ala Glu Tyr Ser Pro Asp Arg Lys
145                 150                 155                 160

Arg Gly Phe Met Gly Ser Trp Leu Asp Phe Gly Ser Ile Ala Gly Phe
            165                 170                 175

Val Leu Gly Ala Gly Val Val Leu Ile Ser Thr Ile Val Gly Glu
        180                 185                 190

Ala Asn Phe Leu Asp Trp Gly Trp Arg Ile Pro Phe Phe Ile Ala Leu
    195                 200                 205

Pro Leu Gly Ile Ile Gly Leu Tyr Leu Arg His Ala Leu Glu Glu Thr
```

```
                210               215               220
Pro Ala Phe Gln Gln His Val Asp Lys Leu Glu Gln Gly Asp Arg Glu
225                 230                 235                 240

Gly Leu Gln Asp Gly Pro Lys Val Ser Phe Lys Glu Ile Ala Thr Lys
                245                 250                 255

Tyr Trp Arg Ser Leu Leu Thr Cys Ile Gly Leu Val Ile Ala Thr Asn
            260                 265                 270

Val Thr Tyr Tyr Met Leu Leu Thr Tyr Met Pro Ser Tyr Leu Ser His
        275                 280                 285

Asn Leu His Tyr Ser Glu Asp His Gly Val Leu Ile Ile Ile Ala Ile
    290                 295                 300

Met Ile Gly Met Leu Phe Val Gln Pro Val Met Gly Leu Leu Ser Asp
305                 310                 315                 320

Arg Phe Gly Arg Pro Phe Val Leu Leu Gly Ser Val Ala Leu Phe
                325                 330                 335

Val Leu Ala Ile Pro Ala Phe Ile Leu Ile Asn Ser Asn Val Ile Gly
            340                 345                 350

Leu Ile Phe Ala Gly Leu Leu Met Leu Ala Val Ile Leu Asn Cys Phe
        355                 360                 365

Thr Gly Val Met Ala Ser Thr Leu Pro Ala Met Phe Pro Thr His Ile
370                 375                 380

Arg Tyr Ser Ala Leu Ala Ala Ala Phe Asn Ile Ser Val Leu Val Ala
385                 390                 395                 400

Gly Leu Thr Pro Thr Leu Ala Ala Trp Leu Val Glu Ser Ser Gln Asn
                405                 410                 415

Leu Met Met Pro Ala Tyr Tyr Leu Met Val Val Ala Val Gly Leu
            420                 425                 430

Ile Thr Gly Val Thr Met Lys Glu Thr Ala Asn Arg Pro Leu Lys Gly
        435                 440                 445

Ala Thr Pro Ala Ala Ser Asp Ile Gln Glu Ala Lys Glu Ile Leu Val
    450                 455                 460

Glu His Tyr Asp Asn Ile Glu Gln Lys Ile Asp Ile Asp His Glu
465                 470                 475                 480

Ile Ala Asp Leu Gln Ala Lys Arg Thr Arg Leu Val Gln Gln His Pro
                485                 490                 495

Arg Ile Asp Glu
            500

<210> SEQ ID NO 3
<211> LENGTH: 1503
<212> TYPE: DNA
<213> ORGANISM: Salmonella enterica
<220> FEATURE:
<221> NAME/KEY: CDS
<222> LOCATION: (1)..(1503)
<223> OTHER INFORMATION: Kodierregion proP

<400> SEQUENCE: 3 atg ctg aaa agg aaa aaa ata aaa ccg att aca ctg ggc gat gtg acc      48
Met Leu Lys Arg Lys Lys Ile Lys Pro Ile Thr Leu Gly Asp Val Thr
1               5                   10                  15 atc att gat gat ggt aaa ctt cgc aaa gcg att acc gcc gcc tcg ctg      96
Ile Ile Asp Asp Gly Lys Leu Arg Lys Ala Ile Thr Ala Ala Ser Leu
            20                  25                  30 ggc aac gcg atg gag tgg ttt gat ttt ggt gtt tat gga ttt gtt gcc     144
Gly Asn Ala Met Glu Trp Phe Asp Phe Gly Val Tyr Gly Phe Val Ala
        35                  40                  45
```

-continued

| | |
|---|---|
| tac gcg ttg ggt aaa gtc ttt ttc ccc ggc gcc gat ccc agc gtc cag<br>Tyr Ala Leu Gly Lys Val Phe Phe Pro Gly Ala Asp Pro Ser Val Gln<br>50                55                60 | 192 |
| atg att gcc gcg ctg gcc acg ttt tcc gtt ccc ttc ctg att cgt ccg<br>Met Ile Ala Ala Leu Ala Thr Phe Ser Val Pro Phe Leu Ile Arg Pro<br>65                70                75              80 | 240 |
| ctc ggc ggg tta ttc ttt ggt atg ctc ggc gat aaa tac ggg cgc cag<br>Leu Gly Gly Leu Phe Phe Gly Met Leu Gly Asp Lys Tyr Gly Arg Gln<br>85                90                95 | 288 |
| aag atc ctg gcg atc acg att gtg att atg tcg atc agt acc ttc tgt<br>Lys Ile Leu Ala Ile Thr Ile Val Ile Met Ser Ile Ser Thr Phe Cys<br>100                105              110 | 336 |
| atc ggg tta atc ccc tct tac gcg acg atc ggt atc tgg gcg cca ata<br>Ile Gly Leu Ile Pro Ser Tyr Ala Thr Ile Gly Ile Trp Ala Pro Ile<br>115                120              125 | 384 |
| ctg ttg ttg ctg tgt aaa atg gcg cag ggc ttc tcg gtt ggc ggg gaa<br>Leu Leu Leu Leu Cys Lys Met Ala Gln Gly Phe Ser Val Gly Gly Glu<br>130                135              140 | 432 |
| tat acc ggc gcg tcg atc ttt gtc gcg gaa tat tcg ccg gat cgt aaa<br>Tyr Thr Gly Ala Ser Ile Phe Val Ala Glu Tyr Ser Pro Asp Arg Lys<br>145                150              155              160 | 480 |
| cgc gga ttt atg gga agc tgg ctg gat ttt ggt tct atc gcc gga ttc<br>Arg Gly Phe Met Gly Ser Trp Leu Asp Phe Gly Ser Ile Ala Gly Phe<br>165                170              175 | 528 |
| gtg ctg ggc gcg ggc gtg gtg gtc ttg atc tcg acg att gtc ggc gag<br>Val Leu Gly Ala Gly Val Val Val Leu Ile Ser Thr Ile Val Gly Glu<br>180                185              190 | 576 |
| gag aat ttc ctt gag tgg ggc tgg cgt att ccg ttc ttt atc gcc ctg<br>Glu Asn Phe Leu Glu Trp Gly Trp Arg Ile Pro Phe Phe Ile Ala Leu<br>195                200              205 | 624 |
| cca ttg ggg att att ggt ctc tac tta cgc cat gcg ctg gag gag acg<br>Pro Leu Gly Ile Ile Gly Leu Tyr Leu Arg His Ala Leu Glu Glu Thr<br>210                215              220 | 672 |
| cca gcg ttt cag cag cac gtg gat aaa ctg gag cag ggc gac cgc gaa<br>Pro Ala Phe Gln Gln His Val Asp Lys Leu Glu Gln Gly Asp Arg Glu<br>225                230              235              240 | 720 |
| ggg ttg cag gat ggg ccg aaa gtc tcc ttt aaa gag att gcc acc aaa<br>Gly Leu Gln Asp Gly Pro Lys Val Ser Phe Lys Glu Ile Ala Thr Lys<br>245                250              255 | 768 |
| cac tgg cgt agc ctg ttg tca tgt atc ggt ctg gtg att gcc acc aac<br>His Trp Arg Ser Leu Leu Ser Cys Ile Gly Leu Val Ile Ala Thr Asn<br>260                265              270 | 816 |
| gtg acc tac tac atg ctc ctc acc tac atg ccg agc tac ctg tcg cat<br>Val Thr Tyr Tyr Met Leu Leu Thr Tyr Met Pro Ser Tyr Leu Ser His<br>275                280              285 | 864 |
| aac ctg cac tat tct gaa gat cac ggc gtg ttg att atc atc gcc att<br>Asn Leu His Tyr Ser Glu Asp His Gly Val Leu Ile Ile Ile Ala Ile<br>290                295              300 | 912 |
| atg atc ggg atg ctg ttt gtg cag ccg gtg atg ggg ctg ctg agc gac<br>Met Ile Gly Met Leu Phe Val Gln Pro Val Met Gly Leu Leu Ser Asp<br>305                310              315              320 | 960 |
| cgt ttc ggt cga cgt cca ttt gtg att atg ggc agc att gcg ctg ttc<br>Arg Phe Gly Arg Arg Pro Phe Val Ile Met Gly Ser Ile Ala Leu Phe<br>325                330              335 | 1008 |
| gcg ctg gcg atc ccg gcc ttc atc ctg att aac agt aac gtt att ggc<br>Ala Leu Ala Ile Pro Ala Phe Ile Leu Ile Asn Ser Asn Val Ile Gly<br>340                345              350 | 1056 |
| ctg att ttt gca ggt ttg ttg atg ctg gcg gtg att ctg aac tgc ttt<br>Leu Ile Phe Ala Gly Leu Leu Met Leu Ala Val Ile Leu Asn Cys Phe | 1104 |

-continued

```
                     355                 360                 365
acc ggg gtg atg gcc tcg aca ttg ccg gcg atg ttt ccg acg cat att      1152
Thr Gly Val Met Ala Ser Thr Leu Pro Ala Met Phe Pro Thr His Ile
370                 375                 380 cgt tat agc gcg ctg gcg gcg gct ttt aat atc tct gta ttg att gcc      1200
Arg Tyr Ser Ala Leu Ala Ala Ala Phe Asn Ile Ser Val Leu Ile Ala
385                 390                 395                 400 ggt ctg acg cca acg ctg gcg gcc tgg ctg gtg gaa agc tcg cag gat      1248
Gly Leu Thr Pro Thr Leu Ala Ala Trp Leu Val Glu Ser Ser Gln Asp
                405                 410                 415 ctg atg atg ccg gcg tat tat ttg atg gtc atc gcg gtg ata ggc ttg      1296
Leu Met Met Pro Ala Tyr Tyr Leu Met Val Ile Ala Val Ile Gly Leu
                420                 425                 430 att acc ggt att tcc atg aaa gag acg gcc aat cgt ccg tta aaa ggc      1344
Ile Thr Gly Ile Ser Met Lys Glu Thr Ala Asn Arg Pro Leu Lys Gly
                435                 440                 445 gca acg cca gcg gcg tcg gac atc cag gaa gcg aag gaa att ctg ggc      1392
Ala Thr Pro Ala Ala Ser Asp Ile Gln Glu Ala Lys Glu Ile Leu Gly
450                 455                 460 gag cat tac gat aat att gag cag aaa atc gac gac atc gat cag gaa      1440
Glu His Tyr Asp Asn Ile Glu Gln Lys Ile Asp Asp Ile Asp Gln Glu
465                 470                 475                 480 att gcg gag ctg cag gtc aaa cgt tcg cgt ctg gta cag caa cat ccg      1488
Ile Ala Glu Leu Gln Val Lys Arg Ser Arg Leu Val Gln Gln His Pro
                485                 490                 495 cgt atc gat gaa taa                                                  1503
Arg Ile Asp Glu
                500
```

<210> SEQ ID NO 4
<211> LENGTH: 500
<212> TYPE: PRT
<213> ORGANISM: Salmonella enterica

<400> SEQUENCE: 4

```
Met Leu Lys Arg Lys Lys Ile Lys Pro Ile Thr Leu Gly Asp Val Thr
1               5                   10                  15

Ile Ile Asp Asp Gly Lys Leu Arg Lys Ala Ile Thr Ala Ala Ser Leu
                20                  25                  30

Gly Asn Ala Met Glu Trp Phe Asp Phe Gly Val Tyr Gly Phe Val Ala
                35                  40                  45

Tyr Ala Leu Gly Lys Val Phe Phe Pro Gly Ala Asp Pro Ser Val Gln
        50                  55                  60

Met Ile Ala Ala Leu Ala Thr Phe Ser Val Pro Phe Leu Ile Arg Pro
65                  70                  75                  80

Leu Gly Gly Leu Phe Phe Gly Met Leu Gly Asp Lys Tyr Gly Arg Gln
                85                  90                  95

Lys Ile Leu Ala Ile Thr Ile Val Met Ser Ile Ser Thr Phe Cys
                100                 105                 110

Ile Gly Leu Ile Pro Ser Tyr Ala Thr Ile Gly Ile Trp Ala Pro Ile
            115                 120                 125

Leu Leu Leu Leu Cys Lys Met Ala Gln Gly Phe Ser Val Gly Gly Glu
        130                 135                 140

Tyr Thr Gly Ala Ser Ile Phe Val Ala Glu Tyr Ser Pro Asp Arg Lys
145                 150                 155                 160

Arg Gly Phe Met Gly Ser Trp Leu Asp Phe Gly Ser Ile Ala Gly Phe
                165                 170                 175
```

```
Val Leu Gly Ala Gly Val Val Leu Ile Ser Thr Ile Val Gly Glu
            180                 185                 190

Glu Asn Phe Leu Glu Trp Gly Trp Arg Ile Pro Phe Phe Ile Ala Leu
        195                 200                 205

Pro Leu Gly Ile Ile Gly Leu Tyr Leu Arg His Ala Leu Glu Glu Thr
        210                 215                 220

Pro Ala Phe Gln Gln His Val Asp Lys Leu Glu Gln Gly Asp Arg Glu
225                 230                 235                 240

Gly Leu Gln Asp Gly Pro Lys Val Ser Phe Lys Glu Ile Ala Thr Lys
                245                 250                 255

His Trp Arg Ser Leu Leu Ser Cys Ile Gly Leu Val Ile Ala Thr Asn
            260                 265                 270

Val Thr Tyr Tyr Met Leu Leu Thr Tyr Met Pro Ser Tyr Leu Ser His
        275                 280                 285

Asn Leu His Tyr Ser Glu Asp His Gly Val Leu Ile Ile Ala Ile
        290                 295                 300

Met Ile Gly Met Leu Phe Val Gln Pro Val Met Gly Leu Leu Ser Asp
305                 310                 315                 320

Arg Phe Gly Arg Arg Pro Phe Val Ile Met Gly Ser Ile Ala Leu Phe
                325                 330                 335

Ala Leu Ala Ile Pro Ala Phe Ile Leu Ile Asn Ser Asn Val Ile Gly
            340                 345                 350

Leu Ile Phe Ala Gly Leu Leu Met Leu Ala Val Ile Leu Asn Cys Phe
        355                 360                 365

Thr Gly Val Met Ala Ser Thr Leu Pro Ala Met Phe Pro Thr His Ile
        370                 375                 380

Arg Tyr Ser Ala Leu Ala Ala Ala Phe Asn Ile Ser Val Leu Ile Ala
385                 390                 395                 400

Gly Leu Thr Pro Thr Leu Ala Ala Trp Leu Val Glu Ser Ser Gln Asp
                405                 410                 415

Leu Met Met Pro Ala Tyr Tyr Leu Met Val Ile Ala Val Ile Gly Leu
            420                 425                 430

Ile Thr Gly Ile Ser Met Lys Glu Thr Ala Asn Arg Pro Leu Lys Gly
        435                 440                 445

Ala Thr Pro Ala Ala Ser Asp Ile Gln Glu Ala Lys Glu Ile Leu Gly
        450                 455                 460

Glu His Tyr Asp Asn Ile Glu Gln Lys Ile Asp Asp Ile Asp Gln Glu
465                 470                 475                 480

Ile Ala Glu Leu Gln Val Lys Arg Ser Arg Leu Val Gln Gln His Pro
                485                 490                 495

Arg Ile Asp Glu
            500

<210> SEQ ID NO 5
<211> LENGTH: 1503
<212> TYPE: DNA
<213> ORGANISM: Shigella sonnei
<220> FEATURE:
<221> NAME/KEY: CDS
<222> LOCATION: (1)..(1503)
<223> OTHER INFORMATION: Kodierregion proP

<400> SEQUENCE: 5 atg ctg aaa agg aaa aaa gta aaa ccg att acc ctt cgt gat gtc acc    48
Met Leu Lys Arg Lys Lys Val Lys Pro Ile Thr Leu Arg Asp Val Thr
1               5                   10                  15
```

| | | | | | | | | | | | | | | | | |
|---|---|---|---|---|---|---|---|---|---|---|---|---|---|---|---|---|
| att | att | gat | gac | ggt | aaa | ctg | cgt | aaa | gcc | att | acc | gca | gca | tca | ctg | 96 |
| Ile | Ile | Asp | Asp | Gly | Lys | Leu | Arg | Lys | Ala | Ile | Thr | Ala | Ala | Ser | Leu | |
| | | 20 | | | | 25 | | | | 30 | | | | | | |

| | | | | | | | | | | | | | | | | |
|---|---|---|---|---|---|---|---|---|---|---|---|---|---|---|---|---|
| ggt | aat | gca | atg | gaa | tgg | ttc | gat | ttt | ggt | gtt | tat | ggt | ttt | gtt | gct | 144 |
| Gly | Asn | Ala | Met | Glu | Trp | Phe | Asp | Phe | Gly | Val | Tyr | Gly | Phe | Val | Ala | |
| | | 35 | | | | 40 | | | | 45 | | | | | | |

| | | | | | | | | | | | | | | | | |
|---|---|---|---|---|---|---|---|---|---|---|---|---|---|---|---|---|
| tac | gca | tta | ggt | aaa | gtt | ttt | ttc | ccg | ggg | gct | gac | ccc | agc | gtg | cag | 192 |
| Tyr | Ala | Leu | Gly | Lys | Val | Phe | Phe | Pro | Gly | Ala | Asp | Pro | Ser | Val | Gln | |
| | 50 | | | | | 55 | | | | 60 | | | | | | |

| | | | | | | | | | | | | | | | | |
|---|---|---|---|---|---|---|---|---|---|---|---|---|---|---|---|---|
| atg | gtt | gct | gca | ctt | gcc | act | ttc | tcc | gtt | ccc | ttt | ctg | att | cga | ccg | 240 |
| Met | Val | Ala | Ala | Leu | Ala | Thr | Phe | Ser | Val | Pro | Phe | Leu | Ile | Arg | Pro | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| ctt | ggc | ggg | ctc | ttc | ttt | ggt | atg | ttg | ggc | gat | aaa | tat | ggt | cgc | cag | 288 |
| Leu | Gly | Gly | Leu | Phe | Phe | Gly | Met | Leu | Gly | Asp | Lys | Tyr | Gly | Arg | Gln | |
| | | | | 85 | | | | 90 | | | | 95 | | | | |

| | | | | | | | | | | | | | | | | |
|---|---|---|---|---|---|---|---|---|---|---|---|---|---|---|---|---|
| aag | atc | ctc | gct | atc | act | att | gtg | att | atg | tcg | atc | agt | acg | ttc | tgt | 336 |
| Lys | Ile | Leu | Ala | Ile | Thr | Ile | Val | Ile | Met | Ser | Ile | Ser | Thr | Phe | Cys | |
| | | | 100 | | | | | 105 | | | | 110 | | | | |

| | | | | | | | | | | | | | | | | |
|---|---|---|---|---|---|---|---|---|---|---|---|---|---|---|---|---|
| att | ggc | tta | ata | ccg | tcc | tac | gac | acg | att | ggt | att | tgg | gca | ccg | att | 384 |
| Ile | Gly | Leu | Ile | Pro | Ser | Tyr | Asp | Thr | Ile | Gly | Ile | Trp | Ala | Pro | Ile | |
| | | 115 | | | | | 120 | | | | 125 | | | | | |

| | | | | | | | | | | | | | | | | |
|---|---|---|---|---|---|---|---|---|---|---|---|---|---|---|---|---|
| ctg | ctg | ttg | atc | tgt | aag | atg | gca | caa | ggt | ttc | tcg | gtc | ggt | ggt | gaa | 432 |
| Leu | Leu | Leu | Ile | Cys | Lys | Met | Ala | Gln | Gly | Phe | Ser | Val | Gly | Gly | Glu | |
| | 130 | | | | | 135 | | | | 140 | | | | | | |

| | | | | | | | | | | | | | | | | |
|---|---|---|---|---|---|---|---|---|---|---|---|---|---|---|---|---|
| tat | acc | ggg | gcg | tcg | ata | ttt | gtt | gcg | gaa | tac | tcc | cct | gac | cgt | aaa | 480 |
| Tyr | Thr | Gly | Ala | Ser | Ile | Phe | Val | Ala | Glu | Tyr | Ser | Pro | Asp | Arg | Lys | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| cgt | ggc | ttt | atg | ggc | agc | tgg | ctg | gac | ttc | ggt | tct | att | gcc | ggg | ttt | 528 |
| Arg | Gly | Phe | Met | Gly | Ser | Trp | Leu | Asp | Phe | Gly | Ser | Ile | Ala | Gly | Phe | |
| | | | | 165 | | | | 170 | | | | 175 | | | | |

| | | | | | | | | | | | | | | | | |
|---|---|---|---|---|---|---|---|---|---|---|---|---|---|---|---|---|
| gtg | ctg | ggt | gcg | ggc | gtg | gtg | gtg | tta | att | tcg | acc | att | gtc | ggc | gaa | 576 |
| Val | Leu | Gly | Ala | Gly | Val | Val | Val | Leu | Ile | Ser | Thr | Ile | Val | Gly | Glu | |
| | | | 180 | | | | | 185 | | | | 190 | | | | |

| | | | | | | | | | | | | | | | | |
|---|---|---|---|---|---|---|---|---|---|---|---|---|---|---|---|---|
| gcg | aac | ttc | ctc | gac | tgg | ggc | tgg | cgt | att | ccg | ttc | ttt | att | gct | ctg | 624 |
| Ala | Asn | Phe | Leu | Asp | Trp | Gly | Trp | Arg | Ile | Pro | Phe | Phe | Ile | Ala | Leu | |
| | | 195 | | | | | 200 | | | | 205 | | | | | |

| | | | | | | | | | | | | | | | | |
|---|---|---|---|---|---|---|---|---|---|---|---|---|---|---|---|---|
| ccg | tta | ggg | att | atc | ggg | ctt | tac | ctg | cgc | cat | gcg | ttg | gaa | gaa | act | 672 |
| Pro | Leu | Gly | Ile | Ile | Gly | Leu | Tyr | Leu | Arg | His | Ala | Leu | Glu | Glu | Thr | |
| | 210 | | | | | 215 | | | | 220 | | | | | | |

| | | | | | | | | | | | | | | | | |
|---|---|---|---|---|---|---|---|---|---|---|---|---|---|---|---|---|
| ccg | gcg | ttc | cag | cag | cat | gtt | gat | aaa | ctg | gaa | cag | ggc | gac | cgc | gaa | 720 |
| Pro | Ala | Phe | Gln | Gln | His | Val | Asp | Lys | Leu | Glu | Gln | Gly | Asp | Arg | Glu | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| ggt | ttg | cag | gat | ggc | ccg | aaa | gtc | tcg | ttt | aaa | gag | att | gcc | act | aaa | 768 |
| Gly | Leu | Gln | Asp | Gly | Pro | Lys | Val | Ser | Phe | Lys | Glu | Ile | Ala | Thr | Lys | |
| | | | | 245 | | | | 250 | | | | 255 | | | | |

| | | | | | | | | | | | | | | | | |
|---|---|---|---|---|---|---|---|---|---|---|---|---|---|---|---|---|
| tac | tgg | cgc | agc | ctg | ttg | aca | tgt | att | ggt | ctg | gta | att | gcc | acc | aac | 816 |
| Tyr | Trp | Arg | Ser | Leu | Leu | Thr | Cys | Ile | Gly | Leu | Val | Ile | Ala | Thr | Asn | |
| | | | 260 | | | | | 265 | | | | 270 | | | | |

| | | | | | | | | | | | | | | | | |
|---|---|---|---|---|---|---|---|---|---|---|---|---|---|---|---|---|
| gtg | act | tac | tac | atg | ttg | ctg | acc | tat | atg | ccg | agt | tat | ttg | tcg | cat | 864 |
| Val | Thr | Tyr | Tyr | Met | Leu | Leu | Thr | Tyr | Met | Pro | Ser | Tyr | Leu | Ser | His | |
| | | 275 | | | | | 280 | | | | 285 | | | | | |

| | | | | | | | | | | | | | | | | |
|---|---|---|---|---|---|---|---|---|---|---|---|---|---|---|---|---|
| aac | ctg | cat | tac | tcc | gaa | gac | cac | ggg | gtg | ctg | att | att | atc | gcc | att | 912 |
| Asn | Leu | His | Tyr | Ser | Glu | Asp | His | Gly | Val | Leu | Ile | Ile | Ile | Ala | Ile | |
| | 290 | | | | | 295 | | | | 300 | | | | | | |

| | | | | | | | | | | | | | | | | |
|---|---|---|---|---|---|---|---|---|---|---|---|---|---|---|---|---|
| atg | atc | ggt | atg | ctg | ttt | gtc | cag | ccg | gtg | atg | ggc | ttg | ctg | agt | gac | 960 |
| Met | Ile | Gly | Met | Leu | Phe | Val | Gln | Pro | Val | Met | Gly | Leu | Leu | Ser | Asp | |
| 305 | | | | 310 | | | | | 315 | | | | | 320 | | |

| | | | | | | | | | | | | | | | | |
|---|---|---|---|---|---|---|---|---|---|---|---|---|---|---|---|---|
| cgt | ttt | ggc | cgt | cgt | ccg | ttt | gtg | cta | ctt | ggt | agt | gtt | gcc | ctg | ttt | 1008 |
| Arg | Phe | Gly | Arg | Arg | Pro | Phe | Val | Leu | Leu | Gly | Ser | Val | Ala | Leu | Phe | |
| | | | 325 | | | | | 330 | | | | 335 | | | | |

```
gtg ttg gcg atc ccg gcg ttt att ctg att aac agt aac gtc atc ggc    1056
Val Leu Ala Ile Pro Ala Phe Ile Leu Ile Asn Ser Asn Val Ile Gly
            340                 345                 350 ctg att ttt gcc ggg tta ctg atg ctg gcg gtg atc ctt aac tgc ttt    1104
Leu Ile Phe Ala Gly Leu Leu Met Leu Ala Val Ile Leu Asn Cys Phe
            355                 360                 365 acg ggc gtt atg gct tct acc ttg cca gcg atg ttc ccg acg cat atc    1152
Thr Gly Val Met Ala Ser Thr Leu Pro Ala Met Phe Pro Thr His Ile
    370                 375                 380 cgt tac agc gcg ctg gcg gcg gca ttt aat att tcg gtg ctg gtt gcc    1200
Arg Tyr Ser Ala Leu Ala Ala Ala Phe Asn Ile Ser Val Leu Val Ala
385                 390                 395                 400 ggt ctg acg cca aca ctg gcg gcc tgg ctg gtc gaa agc tcg cag aat    1248
Gly Leu Thr Pro Thr Leu Ala Ala Trp Leu Val Glu Ser Ser Gln Asn
            405                 410                 415 ctg atg atg cct gcc tat tac ctg atg gta gtg gcg gtg att ggt tta    1296
Leu Met Met Pro Ala Tyr Tyr Leu Met Val Val Ala Val Ile Gly Leu
            420                 425                 430 atc acc ggc gta acc atg aaa gag acg gca aat cgt ccg ttg aaa ggt    1344
Ile Thr Gly Val Thr Met Lys Glu Thr Ala Asn Arg Pro Leu Lys Gly
            435                 440                 445 gcg aca ccg gcg gcg tca gat ata cag gaa gcg aag gaa att ctc gtc    1392
Ala Thr Pro Ala Ala Ser Asp Ile Gln Glu Ala Lys Glu Ile Leu Val
    450                 455                 460 gag cat tac gat aat atc gag cag aaa atc gat gat att gac cac gag    1440
Glu His Tyr Asp Asn Ile Glu Gln Lys Ile Asp Asp Ile Asp His Glu
465                 470                 475                 480 att gcc gat ttg cag gcg aaa cgt acc cgc ctg gtg cag caa cat ccg    1488
Ile Ala Asp Leu Gln Ala Lys Arg Thr Arg Leu Val Gln Gln His Pro
            485                 490                 495 cga att gat gaa taa                                                1503
Arg Ile Asp Glu
        500

<210> SEQ ID NO 6
<211> LENGTH: 500
<212> TYPE: PRT
<213> ORGANISM: Shigella sonnei

<400> SEQUENCE: 6

Met Leu Lys Arg Lys Lys Val Lys Pro Ile Thr Leu Arg Asp Val Thr
1               5                   10                  15

Ile Ile Asp Asp Gly Lys Leu Arg Lys Ala Ile Thr Ala Ala Ser Leu
            20                  25                  30

Gly Asn Ala Met Glu Trp Phe Asp Phe Gly Val Tyr Gly Phe Val Ala
        35                  40                  45

Tyr Ala Leu Gly Lys Val Phe Phe Pro Gly Ala Asp Pro Ser Val Gln
    50                  55                  60

Met Val Ala Ala Leu Ala Thr Phe Ser Val Pro Phe Leu Ile Arg Pro
65                  70                  75                  80

Leu Gly Gly Leu Phe Phe Gly Met Leu Gly Asp Lys Tyr Gly Arg Gln
            85                  90                  95

Lys Ile Leu Ala Ile Thr Ile Val Ile Met Ser Ile Ser Thr Phe Cys
            100                 105                 110

Ile Gly Leu Ile Pro Ser Tyr Asp Thr Ile Gly Ile Trp Ala Pro Ile
        115                 120                 125

Leu Leu Leu Ile Cys Lys Met Ala Gln Gly Phe Ser Val Gly Gly Glu
    130                 135                 140
```

Tyr Thr Gly Ala Ser Ile Phe Val Ala Glu Tyr Ser Pro Asp Arg Lys
145                 150                 155                 160

Arg Gly Phe Met Gly Ser Trp Leu Asp Phe Gly Ser Ile Ala Gly Phe
            165                 170                 175

Val Leu Gly Ala Gly Val Val Leu Ile Ser Thr Ile Val Gly Glu
            180                 185                 190

Ala Asn Phe Leu Asp Trp Gly Trp Arg Ile Pro Phe Phe Ile Ala Leu
        195                 200                 205

Pro Leu Gly Ile Ile Gly Leu Tyr Leu Arg His Ala Leu Glu Glu Thr
    210                 215                 220

Pro Ala Phe Gln Gln His Val Asp Lys Leu Glu Gln Gly Asp Arg Glu
225                 230                 235                 240

Gly Leu Gln Asp Gly Pro Lys Val Ser Phe Lys Glu Ile Ala Thr Lys
            245                 250                 255

Tyr Trp Arg Ser Leu Leu Thr Cys Ile Gly Leu Val Ile Ala Thr Asn
            260                 265                 270

Val Thr Tyr Tyr Met Leu Leu Thr Tyr Met Pro Ser Tyr Leu Ser His
        275                 280                 285

Asn Leu His Tyr Ser Glu Asp His Gly Val Leu Ile Ile Ala Ile
    290                 295                 300

Met Ile Gly Met Leu Phe Val Gln Pro Val Met Gly Leu Leu Ser Asp
305                 310                 315                 320

Arg Phe Gly Arg Arg Pro Phe Val Leu Leu Gly Ser Val Ala Leu Phe
            325                 330                 335

Val Leu Ala Ile Pro Ala Phe Ile Leu Ile Asn Ser Asn Val Ile Gly
            340                 345                 350

Leu Ile Phe Ala Gly Leu Leu Met Leu Ala Val Ile Leu Asn Cys Phe
        355                 360                 365

Thr Gly Val Met Ala Ser Thr Leu Pro Ala Met Phe Pro Thr His Ile
    370                 375                 380

Arg Tyr Ser Ala Leu Ala Ala Phe Asn Ile Ser Val Leu Val Ala
385                 390                 395                 400

Gly Leu Thr Pro Thr Leu Ala Ala Trp Leu Val Glu Ser Ser Gln Asn
            405                 410                 415

Leu Met Met Pro Ala Tyr Tyr Leu Met Val Val Ala Val Ile Gly Leu
            420                 425                 430

Ile Thr Gly Val Thr Met Lys Glu Thr Ala Asn Arg Pro Leu Lys Gly
        435                 440                 445

Ala Thr Pro Ala Ala Ser Asp Ile Gln Glu Ala Lys Glu Ile Leu Val
    450                 455                 460

Glu His Tyr Asp Asn Ile Glu Gln Lys Ile Asp Asp Ile Asp His Glu
465                 470                 475                 480

Ile Ala Asp Leu Gln Ala Lys Arg Thr Arg Leu Val Gln Gln His Pro
            485                 490                 495

Arg Ile Asp Glu
            500

<210> SEQ ID NO 7
<211> LENGTH: 1506
<212> TYPE: DNA
<213> ORGANISM: Erwinia pyrifoliae
<220> FEATURE:
<221> NAME/KEY: CDS
<222> LOCATION: (1)..(1506)
<223> OTHER INFORMATION: Kodierregion proP

<400> SEQUENCE: 7

| | | |
|---|---|---|
| atg aaa tta cgt agg aag cgt gtt aag cct atc gga tta aag gac gtc<br>Met Lys Leu Arg Arg Lys Arg Val Lys Pro Ile Gly Leu Lys Asp Val<br>1                      5                        10                       15 | | 48 |
| acc att att gac gat gcc aga tta cgt aag gcg att aca gct gcc tca<br>Thr Ile Ile Asp Asp Ala Arg Leu Arg Lys Ala Ile Thr Ala Ala Ser<br>                20                       25                      30 | | 96 |
| ttg ggc aat gcc atg gag tgg ttc gac ttt ggc gtt tat ggt ttt gtt<br>Leu Gly Asn Ala Met Glu Trp Phe Asp Phe Gly Val Tyr Gly Phe Val<br>         35                       40                     45 | | 144 |
| gcc tac gca ctg ggg caa gtt ttc ttc ccc ggc gcc gat cca ggg acg<br>Ala Tyr Ala Leu Gly Gln Val Phe Phe Pro Gly Ala Asp Pro Gly Thr<br>50                       55                       60 | | 192 |
| cag atg att gcc gcc ctg gca acc ttc tcc gtg ccc ttc ctg atc cgc<br>Gln Met Ile Ala Ala Leu Ala Thr Phe Ser Val Pro Phe Leu Ile Arg<br>65                       70                       75                     80 | | 240 |
| ccg tta ggc ggc ctg ttc ttt ggg tcg ctg ggg gat aaa tac ggc cgc<br>Pro Leu Gly Gly Leu Phe Phe Gly Ser Leu Gly Asp Lys Tyr Gly Arg<br>         85                       90                     95 | | 288 |
| cag aaa ata ctg tcg ata acc att att atc atg tcg gtc agt acg ttc<br>Gln Lys Ile Leu Ser Ile Thr Ile Ile Ile Met Ser Val Ser Thr Phe<br>              100                     105                    110 | | 336 |
| tgt att ggt tta atc ccg tct tat gcc tcg att ggt atc tgg gca ccg<br>Cys Ile Gly Leu Ile Pro Ser Tyr Ala Ser Ile Gly Ile Trp Ala Pro<br>         115                     120                    125 | | 384 |
| atc ctg cta ttg ctg tgt aaa atg gcg cag ggc ttc tcg gtg ggt ggt<br>Ile Leu Leu Leu Leu Cys Lys Met Ala Gln Gly Phe Ser Val Gly Gly<br>130                      135                     140 | | 432 |
| gaa tat acc ggg gct tcc atc ttc gtt gct gaa tac tca ccg gat cgc<br>Glu Tyr Thr Gly Ala Ser Ile Phe Val Ala Glu Tyr Ser Pro Asp Arg<br>145                      150                     155                    160 | | 480 |
| aaa cgt ggc ttt atg ggc agc tgg ctg gac ttc ggt tcc atc gcc gga<br>Lys Arg Gly Phe Met Gly Ser Trp Leu Asp Phe Gly Ser Ile Ala Gly<br>                    165                     170                    175 | | 528 |
| ttt gtg ctg ggt gcc gga ctg gtg gtg ctg att tca gcg gtt atc ggt<br>Phe Val Leu Gly Ala Gly Leu Val Val Leu Ile Ser Ala Val Ile Gly<br>              180                     185                    190 | | 576 |
| gaa gcg agt ttc ctt gaa tgg ggc tgg cgt att ccg ttc ttc gtg gcg<br>Glu Ala Ser Phe Leu Glu Trp Gly Trp Arg Ile Pro Phe Phe Val Ala<br>         195                     200                    205 | | 624 |
| cta ccg ctg ggt atc atc ggg ctt tat ctg cgc cac gcg ctt gaa gag<br>Leu Pro Leu Gly Ile Ile Gly Leu Tyr Leu Arg His Ala Leu Glu Glu<br>210                      215                     220 | | 672 |
| act ccg gcg ttc cag cag cat gtc gac aag ctg gaa aag ggc gat cgg<br>Thr Pro Ala Phe Gln Gln His Val Asp Lys Leu Glu Lys Gly Asp Arg<br>225                      230                     235                    240 | | 720 |
| gaa gga ttg gcc gat ggg ccg caa gtc tca ttt aaa gag att gcc act<br>Glu Gly Leu Ala Asp Gly Pro Gln Val Ser Phe Lys Glu Ile Ala Thr<br>                    245                     250                    255 | | 768 |
| aag cac tgg aaa agc ctg ctg gcc tgc atc ggt ctg gtg att gcc acc<br>Lys His Trp Lys Ser Leu Leu Ala Cys Ile Gly Leu Val Ile Ala Thr<br>              260                     265                    270 | | 816 |
| aac gtg acc tat tac atg ctg ctg acc tac atg ccg agc tac ctg tcg<br>Asn Val Thr Tyr Tyr Met Leu Leu Thr Tyr Met Pro Ser Tyr Leu Ser<br>         275                     280                    285 | | 864 |
| cat aac ctc cat tat tcg gaa gat cat ggc gtg atg atc att atc gcc<br>His Asn Leu His Tyr Ser Glu Asp His Gly Val Met Ile Ile Ile Ala<br>290                      295                     300 | | 912 |

```
att atg ttg ggg atg ctg ttt gtg cag ccg gtg atg ggc ctg atg agc    960
Ile Met Leu Gly Met Leu Phe Val Gln Pro Val Met Gly Leu Met Ser
305                 310                 315                 320 gac aaa ttc ggt cgt cgc ccg ttt gtt att atc ggc agt atc gcg ctg   1008
Asp Lys Phe Gly Arg Arg Pro Phe Val Ile Ile Gly Ser Ile Ala Leu
                325                 330                 335 ctg acg ctg tca gta ccg tgc ttt atg ctg atc aac agc ggc gtg atg   1056
Leu Thr Leu Ser Val Pro Cys Phe Met Leu Ile Asn Ser Gly Val Met
            340                 345                 350 ggt ctg att ttt gcc ggg ctg ctg acg ctg gcg gtg atc ctt aac agc   1104
Gly Leu Ile Phe Ala Gly Leu Leu Thr Leu Ala Val Ile Leu Asn Ser
        355                 360                 365 ttc acc ggg gtc atg gca tca agc ctg ccg gcg atg ttc ccc act cat   1152
Phe Thr Gly Val Met Ala Ser Ser Leu Pro Ala Met Phe Pro Thr His
    370                 375                 380 atc cgc tac agt gcg ctg gcc agt gcc ttt aac atc tcg gtg ctg gtt   1200
Ile Arg Tyr Ser Ala Leu Ala Ser Ala Phe Asn Ile Ser Val Leu Val
385                 390                 395                 400 gcc ggc ctg acg ccg acc gct gcc gcc tgg ctg gta gaa acg acc agc   1248
Ala Gly Leu Thr Pro Thr Ala Ala Ala Trp Leu Val Glu Thr Thr Ser
                405                 410                 415 aat ttg tat atg cca gct tat tat ctg atg gtc gtc gcg gtg att ggt   1296
Asn Leu Tyr Met Pro Ala Tyr Tyr Leu Met Val Val Ala Val Ile Gly
                420                 425                 430 ctg gta acc ggg att atg atg aag gaa acg gcc aat ctg ccg ctg cgt   1344
Leu Val Thr Gly Ile Met Met Lys Glu Thr Ala Asn Leu Pro Leu Arg
        435                 440                 445 ggc gct gcg cct gcg gct tcg gat atg gct gaa gcg aaa gag atc ctg   1392
Gly Ala Ala Pro Ala Ala Ser Asp Met Ala Glu Ala Lys Glu Ile Leu
    450                 455                 460 cag gaa cat cac gat aat atc gaa cat aag atc gca gat att aac gag   1440
Gln Glu His His Asp Asn Ile Glu His Lys Ile Ala Asp Ile Asn Glu
465                 470                 475                 480 cag atc gct gag ctt gaa gca aaa cgc tcg cat ctt att tat caa cat   1488
Gln Ile Ala Glu Leu Glu Ala Lys Arg Ser His Leu Ile Tyr Gln His
                485                 490                 495 ccg cgt atc aac gag taa                                           1506
Pro Arg Ile Asn Glu
                500

<210> SEQ ID NO 8
<211> LENGTH: 501
<212> TYPE: PRT
<213> ORGANISM: Erwinia pyrifoliae

<400> SEQUENCE: 8

Met Lys Leu Arg Arg Lys Arg Val Lys Pro Ile Gly Leu Lys Asp Val
1               5                   10                  15

Thr Ile Ile Asp Asp Ala Arg Leu Arg Lys Ala Ile Thr Ala Ala Ser
            20                  25                  30

Leu Gly Asn Ala Met Glu Trp Phe Asp Phe Gly Val Tyr Gly Phe Val
        35                  40                  45

Ala Tyr Ala Leu Gly Gln Val Phe Phe Pro Gly Ala Asp Pro Gly Thr
    50                  55                  60

Gln Met Ile Ala Ala Leu Ala Thr Phe Ser Val Pro Phe Leu Ile Arg
65                  70                  75                  80

Pro Leu Gly Gly Leu Phe Phe Gly Ser Leu Gly Asp Lys Tyr Gly Arg
                85                  90                  95

Gln Lys Ile Leu Ser Ile Thr Ile Ile Ile Met Ser Val Ser Thr Phe
```

```
                100                 105                 110
        Cys Ile Gly Leu Ile Pro Ser Tyr Ala Ser Ile Gly Ile Trp Ala Pro
            115                 120                 125
        Ile Leu Leu Leu Leu Cys Lys Met Ala Gln Gly Phe Ser Val Gly Gly
            130                 135                 140
        Glu Tyr Thr Gly Ala Ser Ile Phe Val Ala Glu Tyr Ser Pro Asp Arg
        145                 150                 155                 160
        Lys Arg Gly Phe Met Gly Ser Trp Leu Asp Phe Gly Ser Ile Ala Gly
                            165                 170                 175
        Phe Val Leu Gly Ala Gly Leu Val Val Leu Ile Ser Ala Val Ile Gly
                            180                 185                 190
        Glu Ala Ser Phe Leu Glu Trp Gly Trp Arg Ile Pro Phe Phe Val Ala
                            195                 200                 205
        Leu Pro Leu Gly Ile Ile Gly Leu Tyr Leu Arg His Ala Leu Glu Glu
                            210                 215                 220
        Thr Pro Ala Phe Gln Gln His Val Asp Lys Leu Glu Lys Gly Asp Arg
        225                 230                 235                 240
        Glu Gly Leu Ala Asp Gly Pro Gln Val Ser Phe Lys Glu Ile Ala Thr
                            245                 250                 255
        Lys His Trp Lys Ser Leu Leu Ala Cys Ile Gly Leu Val Ile Ala Thr
                            260                 265                 270
        Asn Val Thr Tyr Tyr Met Leu Leu Thr Tyr Met Pro Ser Tyr Leu Ser
                            275                 280                 285
        His Asn Leu His Tyr Ser Glu Asp His Gly Val Met Ile Ile Ile Ala
                            290                 295                 300
        Ile Met Leu Gly Met Leu Phe Val Gln Pro Val Met Gly Leu Met Ser
        305                 310                 315                 320
        Asp Lys Phe Gly Arg Arg Pro Phe Val Ile Ile Gly Ser Ile Ala Leu
                            325                 330                 335
        Leu Thr Leu Ser Val Pro Cys Phe Met Leu Ile Asn Ser Gly Val Met
                            340                 345                 350
        Gly Leu Ile Phe Ala Gly Leu Leu Thr Leu Ala Val Ile Leu Asn Ser
                            355                 360                 365
        Phe Thr Gly Val Met Ala Ser Ser Leu Pro Ala Met Phe Pro Thr His
                            370                 375                 380
        Ile Arg Tyr Ser Ala Leu Ala Ser Ala Phe Asn Ile Ser Val Leu Val
        385                 390                 395                 400
        Ala Gly Leu Thr Pro Thr Ala Ala Ala Trp Leu Val Glu Thr Thr Ser
                            405                 410                 415
        Asn Leu Tyr Met Pro Ala Tyr Tyr Leu Met Val Val Ala Val Ile Gly
                            420                 425                 430
        Leu Val Thr Gly Ile Met Met Lys Glu Thr Ala Asn Leu Pro Leu Arg
                            435                 440                 445
        Gly Ala Ala Pro Ala Ala Ser Asp Met Ala Glu Ala Lys Glu Ile Leu
                            450                 455                 460
        Gln Glu His His Asp Asn Ile Glu His Lys Ile Ala Asp Ile Asn Glu
        465                 470                 475                 480
        Gln Ile Ala Glu Leu Glu Ala Lys Arg Ser His Leu Ile Tyr Gln His
                            485                 490                 495
        Pro Arg Ile Asn Glu
                            500

<210> SEQ ID NO 9
```

```
<211> LENGTH: 1503
<212> TYPE: DNA
<213> ORGANISM: Escherichia coli
<220> FEATURE:
<221> NAME/KEY: CDS
<222> LOCATION: (1)..(1236)
<223> OTHER INFORMATION: Kodierregion proP M8-Allel (Austausch g zu t
      an Position 1234 bedingt AA-Austausch E412*)

<400> SEQUENCE: 9
```

| | | | | | | | | | | | | | | | | |
|---|---|---|---|---|---|---|---|---|---|---|---|---|---|---|---|---|
| atg | ctg | aaa | agg | aaa | aaa | gta | aaa | ccg | att | acc | ctt | cgt | gat | gtc | acc | 48 |
| Met | Leu | Lys | Arg | Lys | Lys | Val | Lys | Pro | Ile | Thr | Leu | Arg | Asp | Val | Thr | |
| 1 | | | | 5 | | | | | 10 | | | | | 15 | | |
| att | att | gat | gac | ggt | aaa | ctg | cgt | aaa | gcc | att | acc | gca | gca | tca | ctg | 96 |
| Ile | Ile | Asp | Asp | Gly | Lys | Leu | Arg | Lys | Ala | Ile | Thr | Ala | Ala | Ser | Leu | |
| | | | 20 | | | | | 25 | | | | | 30 | | | |
| ggt | aat | gca | atg | gaa | tgg | ttc | gat | ttt | ggt | gtt | tat | ggt | ttt | gtt | gct | 144 |
| Gly | Asn | Ala | Met | Glu | Trp | Phe | Asp | Phe | Gly | Val | Tyr | Gly | Phe | Val | Ala | |
| | 35 | | | | | 40 | | | | | 45 | | | | | |
| tac | gca | tta | ggt | aaa | gtt | ttt | ttc | ccg | ggg | gct | gac | ccc | agc | gtg | cag | 192 |
| Tyr | Ala | Leu | Gly | Lys | Val | Phe | Phe | Pro | Gly | Ala | Asp | Pro | Ser | Val | Gln | |
| 50 | | | | | 55 | | | | | 60 | | | | | | |
| atg | gtt | gct | gca | ctt | gcc | act | ttc | tcc | gtt | ccc | ttt | ctg | att | cga | ccg | 240 |
| Met | Val | Ala | Ala | Leu | Ala | Thr | Phe | Ser | Val | Pro | Phe | Leu | Ile | Arg | Pro | |
| 65 | | | | | 70 | | | | | 75 | | | | | 80 | |
| ctt | ggc | gga | ctc | ttc | ttt | ggt | atg | ttg | ggc | gat | aaa | tat | ggt | cgc | cag | 288 |
| Leu | Gly | Gly | Leu | Phe | Phe | Gly | Met | Leu | Gly | Asp | Lys | Tyr | Gly | Arg | Gln | |
| | | | | 85 | | | | | 90 | | | | | 95 | | |
| aag | atc | ctc | gct | atc | act | att | gtg | att | atg | tcg | atc | agt | acg | ttc | tgt | 336 |
| Lys | Ile | Leu | Ala | Ile | Thr | Ile | Val | Ile | Met | Ser | Ile | Ser | Thr | Phe | Cys | |
| | | 100 | | | | | 105 | | | | | 110 | | | | |
| att | ggc | tta | ata | ccg | tcc | tac | gac | acg | att | ggt | att | tgg | gca | ccg | att | 384 |
| Ile | Gly | Leu | Ile | Pro | Ser | Tyr | Asp | Thr | Ile | Gly | Ile | Trp | Ala | Pro | Ile | |
| | | | 115 | | | | | 120 | | | | | 125 | | | |
| ctg | ctg | ttg | atc | tgt | aag | atg | gca | caa | ggt | ttc | tcg | gtc | ggc | ggt | gaa | 432 |
| Leu | Leu | Leu | Ile | Cys | Lys | Met | Ala | Gln | Gly | Phe | Ser | Val | Gly | Gly | Glu | |
| | | 130 | | | | | 135 | | | | | 140 | | | | |
| tat | acc | ggg | gcg | tcg | ata | ttt | gtt | gcg | gaa | tac | tcc | cct | gac | cgt | aaa | 480 |
| Tyr | Thr | Gly | Ala | Ser | Ile | Phe | Val | Ala | Glu | Tyr | Ser | Pro | Asp | Arg | Lys | |
| 145 | | | | | 150 | | | | | 155 | | | | | 160 | |
| cgt | ggc | ttt | atg | ggc | agc | tgg | ctg | gac | ttc | ggt | tct | att | gcc | ggg | ttt | 528 |
| Arg | Gly | Phe | Met | Gly | Ser | Trp | Leu | Asp | Phe | Gly | Ser | Ile | Ala | Gly | Phe | |
| | | | | 165 | | | | | 170 | | | | | 175 | | |
| gtg | ctg | ggt | gcg | ggc | gtg | gtg | gtg | tta | att | tcg | acc | att | gtc | ggc | gaa | 576 |
| Val | Leu | Gly | Ala | Gly | Val | Val | Val | Leu | Ile | Ser | Thr | Ile | Val | Gly | Glu | |
| | | | | 180 | | | | | 185 | | | | | 190 | | |
| gcg | aac | ttc | ctc | gat | tgg | ggc | tgg | cgt | att | ccg | ttc | ttt | atc | gct | ctg | 624 |
| Ala | Asn | Phe | Leu | Asp | Trp | Gly | Trp | Arg | Ile | Pro | Phe | Phe | Ile | Ala | Leu | |
| | | 195 | | | | | 200 | | | | | 205 | | | | |
| ccg | tta | ggg | att | atc | ggg | ctt | tac | ctg | cgc | cat | gcg | ctg | gaa | gag | act | 672 |
| Pro | Leu | Gly | Ile | Ile | Gly | Leu | Tyr | Leu | Arg | His | Ala | Leu | Glu | Glu | Thr | |
| | | 210 | | | | | 215 | | | | | 220 | | | | |
| ccg | gcg | ttc | cag | cag | cat | gtc | gat | aaa | ctg | gaa | cag | ggc | gac | cgt | gaa | 720 |
| Pro | Ala | Phe | Gln | Gln | His | Val | Asp | Lys | Leu | Glu | Gln | Gly | Asp | Arg | Glu | |
| 225 | | | | | 230 | | | | | 235 | | | | | 240 | |
| ggt | ttg | cag | gat | ggc | ccg | aaa | gtc | tcg | ttt | aaa | gag | att | gcc | act | aaa | 768 |
| Gly | Leu | Gln | Asp | Gly | Pro | Lys | Val | Ser | Phe | Lys | Glu | Ile | Ala | Thr | Lys | |
| | | | | 245 | | | | | 250 | | | | | 255 | | |
| tac | tgg | cgc | agc | ctg | ttg | aca | tgt | att | ggt | ctg | gta | att | gcc | acc | aac | 816 |
| Tyr | Trp | Arg | Ser | Leu | Leu | Thr | Cys | Ile | Gly | Leu | Val | Ile | Ala | Thr | Asn | |
| | | 260 | | | | | 265 | | | | | 270 | | | | |

| | | |
|---|---|---|
| gtg act tac tac atg ttg ctg acc tat atg ccg agt tat ttg tcg cat<br>Val Thr Tyr Tyr Met Leu Leu Thr Tyr Met Pro Ser Tyr Leu Ser His<br>275 280 285 | | 864 |
| aac ctg cat tac tcc gaa gac cac ggg gtg ctg att att atc gcc att<br>Asn Leu His Tyr Ser Glu Asp His Gly Val Leu Ile Ile Ile Ala Ile<br>290 295 300 | | 912 |
| atg atc ggt atg ctg ttt gtc cag ccg gtg atg ggc ttg ctg agt gac<br>Met Ile Gly Met Leu Phe Val Gln Pro Val Met Gly Leu Leu Ser Asp<br>305 310 315 320 | | 960 |
| cgt ttt ggc cgt cgt ccg ttt gtg cta ctt ggt agt gtt gcc ctg ttt<br>Arg Phe Gly Arg Arg Pro Phe Val Leu Leu Gly Ser Val Ala Leu Phe<br>325 330 335 | | 1008 |
| gtg ttg gcg atc ccg gcg ttt att ctg att aac agt aac gtc atc ggc<br>Val Leu Ala Ile Pro Ala Phe Ile Leu Ile Asn Ser Asn Val Ile Gly<br>340 345 350 | | 1056 |
| ctg att ttt gcc ggg tta ctg atg ctg gcg gtg atc ctt aac tgc ttt<br>Leu Ile Phe Ala Gly Leu Leu Met Leu Ala Val Ile Leu Asn Cys Phe<br>355 360 365 | | 1104 |
| acg ggc gtt atg gct tct acc ttg cca gcg atg ttc ccg acg cat atc<br>Thr Gly Val Met Ala Ser Thr Leu Pro Ala Met Phe Pro Thr His Ile<br>370 375 380 | | 1152 |
| cgt tac agc gcg ctg gcg gcg gca ttt aat att tcg gtg ctg gtt gcc<br>Arg Tyr Ser Ala Leu Ala Ala Ala Phe Asn Ile Ser Val Leu Val Ala<br>385 390 395 400 | | 1200 |
| ggt ctg acg cca acg ctg gcg gcc tgg ctg gtc taa agctcgcaga<br>Gly Leu Thr Pro Thr Leu Ala Ala Trp Leu Val<br>405 410 | | 1246 |
| atctgatgat gcctgcctat tacctgatgg tagtggcggt ggttggttta atcaccggcg | | 1306 |
| taaccatgaa agagacggca atcgtccgt tgaaaggtgc gacaccggcg gcgtcagata | | 1366 |
| tacaggaagc gaaggaaatt ctcgtcgagc attacgataa tatcgagcag aaaatcgatg | | 1426 |
| atattgacca cgagattgcc gatttgcagg cgaaacgtac ccgcctggtg cagcaacatc | | 1486 |
| cgcgaattga tgaataa | | 1503 |

<210> SEQ ID NO 10
<211> LENGTH: 411
<212> TYPE: PRT
<213> ORGANISM: Escherichia coli

<400> SEQUENCE: 10

Met Leu Lys Arg Lys Val Lys Pro Ile Thr Leu Arg Asp Val Thr
1               5                   10                  15

Ile Ile Asp Asp Gly Lys Leu Arg Lys Ala Ile Thr Ala Ala Ser Leu
            20                  25                  30

Gly Asn Ala Met Glu Trp Phe Asp Phe Gly Val Tyr Gly Phe Val Ala
        35                  40                  45

Tyr Ala Leu Gly Lys Val Phe Phe Pro Gly Ala Asp Pro Ser Val Gln
    50                  55                  60

Met Val Ala Ala Leu Ala Thr Phe Ser Val Pro Phe Leu Ile Arg Pro
65                  70                  75                  80

Leu Gly Gly Leu Phe Phe Gly Met Leu Gly Asp Lys Tyr Gly Arg Gln
                85                  90                  95

Lys Ile Leu Ala Ile Thr Ile Val Ile Met Ser Ile Ser Thr Phe Cys
            100                 105                 110

Ile Gly Leu Ile Pro Ser Tyr Asp Thr Ile Gly Ile Trp Ala Pro Ile
        115                 120                 125

Leu Leu Leu Ile Cys Lys Met Ala Gln Gly Phe Ser Val Gly Gly Glu

```
          130                 135                 140
Tyr Thr Gly Ala Ser Ile Phe Val Ala Glu Tyr Ser Pro Asp Arg Lys
145                 150                 155                 160

Arg Gly Phe Met Gly Ser Trp Leu Asp Phe Gly Ser Ile Ala Gly Phe
                165                 170                 175

Val Leu Gly Ala Gly Val Val Leu Ile Ser Thr Ile Val Gly Glu
            180                 185                 190

Ala Asn Phe Leu Asp Trp Gly Trp Arg Ile Pro Phe Phe Ile Ala Leu
        195                 200                 205

Pro Leu Gly Ile Ile Gly Leu Tyr Leu Arg His Ala Leu Glu Glu Thr
    210                 215                 220

Pro Ala Phe Gln Gln His Val Asp Lys Leu Glu Gln Gly Asp Arg Glu
225                 230                 235                 240

Gly Leu Gln Asp Gly Pro Lys Val Ser Phe Lys Glu Ile Ala Thr Lys
                245                 250                 255

Tyr Trp Arg Ser Leu Leu Thr Cys Ile Gly Leu Val Ile Ala Thr Asn
            260                 265                 270

Val Thr Tyr Tyr Met Leu Leu Thr Tyr Met Pro Ser Tyr Leu Ser His
        275                 280                 285

Asn Leu His Tyr Ser Glu Asp His Gly Val Leu Ile Ile Ile Ala Ile
    290                 295                 300

Met Ile Gly Met Leu Phe Val Gln Pro Val Met Gly Leu Leu Ser Asp
305                 310                 315                 320

Arg Phe Gly Arg Arg Pro Phe Val Leu Leu Gly Ser Val Ala Leu Phe
                325                 330                 335

Val Leu Ala Ile Pro Ala Phe Ile Leu Ile Asn Ser Asn Val Ile Gly
            340                 345                 350

Leu Ile Phe Ala Gly Leu Leu Met Leu Ala Val Ile Leu Asn Cys Phe
        355                 360                 365

Thr Gly Val Met Ala Ser Thr Leu Pro Ala Met Phe Pro Thr His Ile
    370                 375                 380

Arg Tyr Ser Ala Leu Ala Ala Ala Phe Asn Ile Ser Val Leu Val Ala
385                 390                 395                 400

Gly Leu Thr Pro Thr Leu Ala Ala Trp Leu Val
                405                 410
```

<210> SEQ ID NO 11
<211> LENGTH: 1504
<212> TYPE: DNA
<213> ORGANISM: Escherichia coli
<220> FEATURE:
<221> NAME/KEY: CDS
<222> LOCATION: (1)..(867)
<223> OTHER INFORMATION: Kodierregion proP M3-Allel (Insertion von C
      nach Nukleotidposition 842)

<400> SEQUENCE: 11

```
atg ctg aaa agg aaa aaa gta aaa ccg att acc ctt cgt gat gtc acc      48
Met Leu Lys Arg Lys Lys Val Lys Pro Ile Thr Leu Arg Asp Val Thr
1               5                   10                  15 att att gat gac ggt aaa ctg cgt aaa gcc att acc gca gca tca ctg      96
Ile Ile Asp Asp Gly Lys Leu Arg Lys Ala Ile Thr Ala Ala Ser Leu
                20                  25                  30 ggt aat gca atg gaa tgg ttc gat ttt ggt gtt tat ggt ttt gtt gct     144
Gly Asn Ala Met Glu Trp Phe Asp Phe Gly Val Tyr Gly Phe Val Ala
            35                  40                  45 tac gca tta ggt aaa gtt ttt ttc ccg ggg gct gac ccc agc gtg cag     192
```

```
Tyr Ala Leu Gly Lys Val Phe Phe Pro Gly Ala Asp Pro Ser Val Gln
 50              55                  60 atg gtt gct gca ctt gcc act ttc tcc gtt ccc ttt ctg att cga ccg        240
Met Val Ala Ala Leu Ala Thr Phe Ser Val Pro Phe Leu Ile Arg Pro
 65              70                  75                  80 ctt ggc gga ctc ttc ttt ggt atg ttg ggc gat aaa tat ggt cgc cag        288
Leu Gly Gly Leu Phe Phe Gly Met Leu Gly Asp Lys Tyr Gly Arg Gln
                 85                  90                  95 aag atc ctc gct atc act att gtg att atg tcg atc agt acg ttc tgt        336
Lys Ile Leu Ala Ile Thr Ile Val Ile Met Ser Ile Ser Thr Phe Cys
            100                 105                 110 att ggc tta ata ccg tcc tac gac acg att ggt att tgg gca ccg att        384
Ile Gly Leu Ile Pro Ser Tyr Asp Thr Ile Gly Ile Trp Ala Pro Ile
        115                 120                 125 ctg ctg ttg atc tgt aag atg gca caa ggt ttc tcg gtc ggc ggt gaa        432
Leu Leu Leu Ile Cys Lys Met Ala Gln Gly Phe Ser Val Gly Gly Glu
    130                 135                 140 tat acc ggg gcg tcg ata ttt gtt gcg gaa tac tcc cct gac cgt aaa        480
Tyr Thr Gly Ala Ser Ile Phe Val Ala Glu Tyr Ser Pro Asp Arg Lys
145                 150                 155                 160 cgt ggc ttt atg ggc agc tgg ctg gac ttc ggt tct att gcc ggg ttt        528
Arg Gly Phe Met Gly Ser Trp Leu Asp Phe Gly Ser Ile Ala Gly Phe
                165                 170                 175 gtg ctg ggt gcg ggc gtg gtg gtg tta att tcg acc att gtc ggc gaa        576
Val Leu Gly Ala Gly Val Val Val Leu Ile Ser Thr Ile Val Gly Glu
            180                 185                 190 gcg aac ttc ctc gat tgg ggc tgg cgt att ccg ttc ttt atc gct ctg        624
Ala Asn Phe Leu Asp Trp Gly Trp Arg Ile Pro Phe Phe Ile Ala Leu
        195                 200                 205 ccg tta ggg att atc ggg ctt tac ctg cgc cat gcg ctg gaa gag act        672
Pro Leu Gly Ile Ile Gly Leu Tyr Leu Arg His Ala Leu Glu Glu Thr
    210                 215                 220 ccg gcg ttc cag cag cat gtc gat aaa ctg gaa cag ggc gac cgt gaa        720
Pro Ala Phe Gln Gln His Val Asp Lys Leu Glu Gln Gly Asp Arg Glu
225                 230                 235                 240 ggt ttg cag gat ggc ccg aaa gtc tcg ttt aaa gag att gcc act aaa        768
Gly Leu Gln Asp Gly Pro Lys Val Ser Phe Lys Glu Ile Ala Thr Lys
                245                 250                 255 tac tgg cgc agc ctg ttg aca tgt att ggt ctg gta att gcc acc aac        816
Tyr Trp Arg Ser Leu Leu Thr Cys Ile Gly Leu Val Ile Ala Thr Asn
            260                 265                 270 gtg act tac tac atg ttg ctg acc tac tat gcc gag tta ttt gtc gca        864
Val Thr Tyr Tyr Met Leu Leu Thr Tyr Tyr Ala Glu Leu Phe Val Ala
        275                 280                 285 taa cctgcattac tccgaagacc acgggtgct gattattatc gccattatga              917
tcggtatgct gtttgtccag ccggtgatgg gcttgctgag tgaccgtttt ggccgtcgtc      977
cgtttgtgct acttggtagt gttgccctgt ttgtgttggc gatcccggcg tttattctga     1037
ttaacagtaa cgtcatcggc ctgattttg ccgggttact gatgctggcg gtgatcctta     1097
actgctttac gggcgttatg gcttctacct tgccagcgat gttcccgacg catatccgtt     1157
acagcgcgct ggcggcggca tttaatattt cggtgctggt tgccggtctg acgccaacgc    1217
tggcggcctg gctggtcgaa agctcgcaga atctgatgat gcctgcctat tacctgatgg    1277
tagtggcggt ggttggttta atcaccggcg taaccatgaa agagacggca atcgtccgt     1337 tgaaaggtgc gacaccggcg gcgtcagata tacaggaagc gaaggaaatt ctcgtcgagc    1397
attacgataa tatcgagcag aaaatcgatg atattgacca cgagattgcc gatttgcagg    1457
```
cgaaacgtac cgcctggtg cagcaacatc cgcgaattga tgaataa 1504

<210> SEQ ID NO 12
<211> LENGTH: 288
<212> TYPE: PRT
<213> ORGANISM: Escherichia coli

<400> SEQUENCE: 12

Met Leu Lys Arg Lys Lys Val Lys Pro Ile Thr Leu Arg Asp Val Thr
1               5                   10                  15

Ile Ile Asp Asp Gly Lys Leu Arg Lys Ala Ile Thr Ala Ala Ser Leu
            20                  25                  30

Gly Asn Ala Met Glu Trp Phe Asp Phe Gly Val Tyr Gly Phe Val Ala
        35                  40                  45

Tyr Ala Leu Gly Lys Val Phe Phe Pro Gly Ala Asp Pro Ser Val Gln
    50                  55                  60

Met Val Ala Ala Leu Ala Thr Phe Ser Val Pro Phe Leu Ile Arg Pro
65                  70                  75                  80

Leu Gly Gly Leu Phe Phe Gly Met Leu Gly Asp Lys Tyr Gly Arg Gln
                85                  90                  95

Lys Ile Leu Ala Ile Thr Ile Val Ile Met Ser Ile Ser Thr Phe Cys
            100                 105                 110

Ile Gly Leu Ile Pro Ser Tyr Asp Thr Ile Gly Ile Trp Ala Pro Ile
        115                 120                 125

Leu Leu Leu Ile Cys Lys Met Ala Gln Gly Phe Ser Val Gly Gly Glu
    130                 135                 140

Tyr Thr Gly Ala Ser Ile Phe Val Ala Glu Tyr Ser Pro Asp Arg Lys
145                 150                 155                 160

Arg Gly Phe Met Gly Ser Trp Leu Asp Phe Gly Ser Ile Ala Gly Phe
                165                 170                 175

Val Leu Gly Ala Gly Val Val Leu Ile Ser Thr Ile Val Gly Glu
            180                 185                 190

Ala Asn Phe Leu Asp Trp Gly Trp Arg Ile Pro Phe Phe Ile Ala Leu
        195                 200                 205

Pro Leu Gly Ile Ile Gly Leu Tyr Leu Arg His Ala Leu Glu Glu Thr
    210                 215                 220

Pro Ala Phe Gln Gln His Val Asp Lys Leu Glu Gln Gly Asp Arg Glu
225                 230                 235                 240

Gly Leu Gln Asp Gly Pro Lys Val Ser Phe Lys Glu Ile Ala Thr Lys
                245                 250                 255

Tyr Trp Arg Ser Leu Leu Thr Cys Ile Gly Leu Val Ile Ala Thr Asn
            260                 265                 270

Val Thr Tyr Tyr Met Leu Leu Thr Tyr Ala Glu Leu Phe Val Ala
        275                 280                 285

<210> SEQ ID NO 13
<211> LENGTH: 1502
<212> TYPE: DNA
<213> ORGANISM: Escherichia coli
<220> FEATURE:
<221> NAME/KEY: CDS
<222> LOCATION: (1)..(897)
<223> OTHER INFORMATION: Kodierregion proP M4-Allel (Deletion A nach
      Nukleotidposition 854)

<400> SEQUENCE: 13 atg ctg aaa agg aaa aaa gta aaa ccg att acc ctt cgt gat gtc acc    48
Met Leu Lys Arg Lys Lys Val Lys Pro Ile Thr Leu Arg Asp Val Thr

```
          1               5                      10                      15
att att gat gac ggt aaa ctg cgt aaa gcc att acc gca gca tca ctg       96
Ile Ile Asp Asp Gly Lys Leu Arg Lys Ala Ile Thr Ala Ala Ser Leu
            20                      25                  30 ggt aat gca atg gaa tgg ttc gat ttt ggt gtt tat ggt ttt gtt gct      144
Gly Asn Ala Met Glu Trp Phe Asp Phe Gly Val Tyr Gly Phe Val Ala
        35                      40                  45 tac gca tta ggt aaa gtt ttt ttc ccg ggg gct gac ccc agc gtg cag      192
Tyr Ala Leu Gly Lys Val Phe Phe Pro Gly Ala Asp Pro Ser Val Gln
    50                      55                  60 atg gtt gct gca ctt gcc act ttc tcc gtt ccc ttt ctg att cga ccg      240
Met Val Ala Ala Leu Ala Thr Phe Ser Val Pro Phe Leu Ile Arg Pro
65                      70                  75                  80 ctt ggc gga ctc ttc ttt ggt atg ttg ggc gat aaa tat ggt cgc cag      288
Leu Gly Gly Leu Phe Phe Gly Met Leu Gly Asp Lys Tyr Gly Arg Gln
                    85                  90                  95 aag atc ctc gct atc act att gtg att atg tcg atc agt acg ttc tgt      336
Lys Ile Leu Ala Ile Thr Ile Val Ile Met Ser Ile Ser Thr Phe Cys
                100                 105                 110 att ggc tta ata ccg tcc tac gac acg att ggt att tgg gca ccg att      384
Ile Gly Leu Ile Pro Ser Tyr Asp Thr Ile Gly Ile Trp Ala Pro Ile
            115                 120                 125 ctg ctg ttg atc tgt aag atg gca caa ggt ttc tcg gtc ggc ggt gaa      432
Leu Leu Leu Ile Cys Lys Met Ala Gln Gly Phe Ser Val Gly Gly Glu
        130                 135                 140 tat acc ggg gcg tcg ata ttt gtt gcg gaa tac tcc cct gac cgt aaa      480
Tyr Thr Gly Ala Ser Ile Phe Val Ala Glu Tyr Ser Pro Asp Arg Lys
145                 150                 155                 160 cgt ggc ttt atg ggc agc tgg ctg gac ttc ggt tct att gcc ggg ttt      528
Arg Gly Phe Met Gly Ser Trp Leu Asp Phe Gly Ser Ile Ala Gly Phe
                    165                 170                 175 gtg ctg ggt gcg ggc gtg gtg gtg tta att tcg acc att gtc ggc gaa      576
Val Leu Gly Ala Gly Val Val Val Leu Ile Ser Thr Ile Val Gly Glu
                180                 185                 190 gcg aac ttc ctc gat tgg ggc tgg cgt att ccg ttc ttt atc gct ctg      624
Ala Asn Phe Leu Asp Trp Gly Trp Arg Ile Pro Phe Phe Ile Ala Leu
            195                 200                 205 ccg tta ggg att atc ggg ctt tac ctg cgc cat gcg ctg gaa gag act      672
Pro Leu Gly Ile Ile Gly Leu Tyr Leu Arg His Ala Leu Glu Glu Thr
        210                 215                 220 ccg gcg ttc cag cag cat gtc gat aaa ctg gaa cag ggc gac cgt gaa      720
Pro Ala Phe Gln Gln His Val Asp Lys Leu Glu Gln Gly Asp Arg Glu
225                 230                 235                 240 ggt ttg cag gat ggc ccg aaa gtc tcg ttt aaa gag att gcc act aaa      768
Gly Leu Gln Asp Gly Pro Lys Val Ser Phe Lys Glu Ile Ala Thr Lys
                    245                 250                 255 tac tgg cgc agc ctg tta aca tgt att ggt ctg gta att gcc acc aac      816
Tyr Trp Arg Ser Leu Leu Thr Cys Ile Gly Leu Val Ile Ala Thr Asn
                260                 265                 270 gtg act tac tac atg ttg ctg acc tat atg ccg agt ttt tgt cgc ata      864
Val Thr Tyr Tyr Met Leu Leu Thr Tyr Met Pro Ser Phe Cys Arg Ile
            275                 280                 285 acc tgc att act ccg aag acc acg ggg tgc tga ttattatcgc cattatgatc    917
Thr Cys Ile Thr Pro Lys Thr Thr Gly Cys
        290                 295 ggtatgctgt tgtccagcc ggtgatgggc ttgctgagtg accgttttgg ccgtcgtccg     977
tttgtgctac ttggtagtgt tgccctgttt gtgttggcga tcccggcgtt tattctgatt   1037
aacagtaacg tcatcggcct gatttttgcc gggttactga tgctggcggt gatccttaac   1097
```

-continued

```
tgctttacgg gcgttatggc ttctaccttg ccagcgatgt tcccgacgca tatccgttac    1157
agcgcgctgg cggcggcatt taatatttcg gtgctggttg ccggtctgac gccaacgctg    1217
gcggcctggc tggtcgaaag ctcgcagaat ctgatgatgc ctgcctatta cctgatggta    1277
gtggcggtgg ttggtttaat caccggcgta accatgaaag agacggcaaa tcgtccgttg    1337
aaaggtgcga caccggcggc gtcagatata caggaagcga aggaaattct cgtcgagcat    1397
tacgataata tcgagcagaa aatcgatgat attgaccacg agattgccga tttgcaggcg    1457
aaacgtaccc gcctggtgca gcaacatccg cgaattgatg aataa                    1502
```

<210> SEQ ID NO 14
<211> LENGTH: 298
<212> TYPE: PRT
<213> ORGANISM: Escherichia coli

<400> SEQUENCE: 14

```
Met Leu Lys Arg Lys Val Lys Pro Ile Thr Leu Arg Asp Val Thr
1               5                   10                  15

Ile Ile Asp Asp Gly Lys Leu Arg Lys Ala Ile Thr Ala Ala Ser Leu
                20                  25                  30

Gly Asn Ala Met Glu Trp Phe Asp Phe Gly Val Tyr Gly Phe Val Ala
                35                  40                  45

Tyr Ala Leu Gly Lys Val Phe Phe Pro Gly Ala Asp Pro Ser Val Gln
        50                  55                  60

Met Val Ala Ala Leu Ala Thr Phe Ser Val Pro Phe Leu Ile Arg Pro
65                  70                  75                  80

Leu Gly Gly Leu Phe Phe Gly Met Leu Gly Asp Lys Tyr Gly Arg Gln
                85                  90                  95

Lys Ile Leu Ala Ile Thr Ile Val Ile Met Ser Ile Ser Thr Phe Cys
                100                 105                 110

Ile Gly Leu Ile Pro Ser Tyr Asp Thr Ile Gly Ile Trp Ala Pro Ile
            115                 120                 125

Leu Leu Leu Ile Cys Lys Met Ala Gln Gly Phe Ser Val Gly Gly Glu
    130                 135                 140

Tyr Thr Gly Ala Ser Ile Phe Val Ala Glu Tyr Ser Pro Asp Arg Lys
145                 150                 155                 160

Arg Gly Phe Met Gly Ser Trp Leu Asp Phe Gly Ser Ile Ala Gly Phe
                165                 170                 175

Val Leu Gly Ala Gly Val Val Val Leu Ile Ser Thr Ile Val Gly Glu
                180                 185                 190

Ala Asn Phe Leu Asp Trp Gly Trp Arg Ile Pro Phe Phe Ile Ala Leu
            195                 200                 205

Pro Leu Gly Ile Ile Gly Leu Tyr Leu Arg His Ala Leu Glu Glu Thr
    210                 215                 220

Pro Ala Phe Gln Gln His Val Asp Lys Leu Glu Gln Gly Asp Arg Glu
225                 230                 235                 240

Gly Leu Gln Asp Gly Pro Lys Val Ser Phe Lys Glu Ile Ala Thr Lys
                245                 250                 255

Tyr Trp Arg Ser Leu Leu Thr Cys Ile Gly Leu Val Ile Ala Thr Asn
                260                 265                 270

Val Thr Tyr Tyr Met Leu Leu Thr Tyr Met Pro Ser Phe Cys Arg Ile
            275                 280                 285

Thr Cys Ile Thr Pro Lys Thr Thr Gly Cys
    290                 295
```

```
<210> SEQ ID NO 15
<211> LENGTH: 1503
<212> TYPE: DNA
<213> ORGANISM: Escherichia coli
<220> FEATURE:
<221> NAME/KEY: CDS
<222> LOCATION: (1)..(1503)
<223> OTHER INFORMATION: Kodierregion proP M11-Allel (Austausch t zu c
      an Position 1399 bedingt AA-Austausch Y467H)

<400> SEQUENCE: 15
```

| | | | | | | | | | | | | | | | | |
|---|---|---|---|---|---|---|---|---|---|---|---|---|---|---|---|---|
| atg | ctg | aaa | agg | aaa | aaa | gta | aaa | ccg | att | acc | ctt | cgt | gat | gtc | acc | 48 |
| Met | Leu | Lys | Arg | Lys | Lys | Val | Lys | Pro | Ile | Thr | Leu | Arg | Asp | Val | Thr | |
| 1 | | | | 5 | | | | | 10 | | | | | 15 | | |
| att | att | gat | gac | ggt | aaa | ctg | cgt | aaa | gcc | att | acc | gca | gca | tca | ctg | 96 |
| Ile | Ile | Asp | Asp | Gly | Lys | Leu | Arg | Lys | Ala | Ile | Thr | Ala | Ala | Ser | Leu | |
| | | | 20 | | | | | 25 | | | | | 30 | | | |
| ggt | aat | gca | atg | gaa | tgg | ttc | gat | ttt | ggt | gtt | tat | ggt | ttt | gtt | gct | 144 |
| Gly | Asn | Ala | Met | Glu | Trp | Phe | Asp | Phe | Gly | Val | Tyr | Gly | Phe | Val | Ala | |
| | | 35 | | | | | 40 | | | | | 45 | | | | |
| tac | gca | tta | ggt | aaa | gtt | ttt | ttc | ccg | ggg | gct | gac | ccc | agc | gtg | cag | 192 |
| Tyr | Ala | Leu | Gly | Lys | Val | Phe | Phe | Pro | Gly | Ala | Asp | Pro | Ser | Val | Gln | |
| 50 | | | | | 55 | | | | | 60 | | | | | | |
| atg | gtt | gct | gca | ctt | gcc | act | ttc | tcc | gtt | ccc | ttt | ctg | att | cga | ccg | 240 |
| Met | Val | Ala | Ala | Leu | Ala | Thr | Phe | Ser | Val | Pro | Phe | Leu | Ile | Arg | Pro | |
| 65 | | | | | 70 | | | | | 75 | | | | | 80 | |
| ctt | ggc | gga | ctc | ttc | ttt | ggt | atg | ttg | ggc | gat | aaa | tat | ggt | cgc | cag | 288 |
| Leu | Gly | Gly | Leu | Phe | Phe | Gly | Met | Leu | Gly | Asp | Lys | Tyr | Gly | Arg | Gln | |
| | | | | 85 | | | | | 90 | | | | | 95 | | |
| aag | atc | ctc | gct | atc | act | att | gtg | att | atg | tcg | atc | agt | acg | ttc | tgt | 336 |
| Lys | Ile | Leu | Ala | Ile | Thr | Ile | Val | Ile | Met | Ser | Ile | Ser | Thr | Phe | Cys | |
| | | | 100 | | | | | 105 | | | | | 110 | | | |
| att | ggc | tta | ata | ccg | tcc | tac | gac | acg | att | ggt | att | tgg | gca | ccg | att | 384 |
| Ile | Gly | Leu | Ile | Pro | Ser | Tyr | Asp | Thr | Ile | Gly | Ile | Trp | Ala | Pro | Ile | |
| | | 115 | | | | | 120 | | | | | 125 | | | | |
| ctg | ctg | ttg | atc | tgt | aag | atg | gca | caa | ggt | ttc | tcg | gtc | ggc | ggt | gaa | 432 |
| Leu | Leu | Leu | Ile | Cys | Lys | Met | Ala | Gln | Gly | Phe | Ser | Val | Gly | Gly | Glu | |
| | 130 | | | | | 135 | | | | | 140 | | | | | |
| tat | acc | ggg | gcg | tcg | ata | ttt | gtt | gcg | gaa | tac | tcc | cct | gac | cgt | aaa | 480 |
| Tyr | Thr | Gly | Ala | Ser | Ile | Phe | Val | Ala | Glu | Tyr | Ser | Pro | Asp | Arg | Lys | |
| 145 | | | | | 150 | | | | | 155 | | | | | 160 | |
| cgt | ggc | ttt | atg | ggc | agc | tgg | ctg | gac | ttc | ggt | tct | att | gcc | ggg | ttt | 528 |
| Arg | Gly | Phe | Met | Gly | Ser | Trp | Leu | Asp | Phe | Gly | Ser | Ile | Ala | Gly | Phe | |
| | | | | 165 | | | | | 170 | | | | | 175 | | |
| gtg | ctg | ggt | gcg | ggc | gtg | gtg | gtg | tta | att | tcg | acc | att | gtc | ggc | gaa | 576 |
| Val | Leu | Gly | Ala | Gly | Val | Val | Val | Leu | Ile | Ser | Thr | Ile | Val | Gly | Glu | |
| | | | 180 | | | | | 185 | | | | | 190 | | | |
| gcg | aac | ttc | ctc | gat | tgg | ggc | tgg | cgt | att | ccg | ttc | ttt | atc | gct | ctg | 624 |
| Ala | Asn | Phe | Leu | Asp | Trp | Gly | Trp | Arg | Ile | Pro | Phe | Phe | Ile | Ala | Leu | |
| | | 195 | | | | | 200 | | | | | 205 | | | | |
| ccg | tta | ggg | att | atc | ggg | ctt | tac | ctg | cgc | cat | gcg | ctg | gaa | gag | act | 672 |
| Pro | Leu | Gly | Ile | Ile | Gly | Leu | Tyr | Leu | Arg | His | Ala | Leu | Glu | Glu | Thr | |
| | 210 | | | | | 215 | | | | | 220 | | | | | |
| ccg | gcg | ttc | cag | cag | cat | gtc | gat | aaa | ctg | gaa | cag | ggc | gac | cgt | gaa | 720 |
| Pro | Ala | Phe | Gln | Gln | His | Val | Asp | Lys | Leu | Glu | Gln | Gly | Asp | Arg | Glu | |
| 225 | | | | | 230 | | | | | 235 | | | | | 240 | |
| ggt | ttg | cag | gat | ggc | ccg | aaa | gtc | tcg | ttt | aaa | gag | att | gcc | act | aaa | 768 |
| Gly | Leu | Gln | Asp | Gly | Pro | Lys | Val | Ser | Phe | Lys | Glu | Ile | Ala | Thr | Lys | |
| | | | | 245 | | | | | 250 | | | | | 255 | | |
| tac | tgg | cgc | agc | ctg | ttg | aca | tgt | att | ggt | ctg | gta | att | gcc | acc | aac | 816 |

-continued

```
            Tyr Trp Arg Ser Leu Leu Thr Cys Ile Gly Leu Val Ile Ala Thr Asn
                    260                 265                 270 gtg act tac tac atg ttg ctg acc tat atg ccg agt tat ttg tcg cat        864
Val Thr Tyr Tyr Met Leu Leu Thr Tyr Met Pro Ser Tyr Leu Ser His
            275                 280                 285 aac ctg cat tac tcc gaa gac cac ggg gtg ctg att att atc gcc att        912
Asn Leu His Tyr Ser Glu Asp His Gly Val Leu Ile Ile Ile Ala Ile
        290                 295                 300 atg atc ggt atg ctg ttt gtc cag ccg gtg atg ggc ttg ctg agt gac        960
Met Ile Gly Met Leu Phe Val Gln Pro Val Met Gly Leu Leu Ser Asp
305                 310                 315                 320 cgt ttt ggc cgt cgt ccg ttt gtg cta ctt ggt agt gtt gcc ctg ttt       1008
Arg Phe Gly Arg Arg Pro Phe Val Leu Leu Gly Ser Val Ala Leu Phe
                325                 330                 335 gtg ttg gcg atc ccg gcg ttt att ctg att aac agt aac gtc atc ggc       1056
Val Leu Ala Ile Pro Ala Phe Ile Leu Ile Asn Ser Asn Val Ile Gly
            340                 345                 350 ctg att ttt gcc ggg tta ctg atg ctg gcg gtg atc ctt aac tgc ttt       1104
Leu Ile Phe Ala Gly Leu Leu Met Leu Ala Val Ile Leu Asn Cys Phe
        355                 360                 365 acg ggc gtt atg gct tct acc ttg cca gcg atg ttc ccg acg cat atc       1152
Thr Gly Val Met Ala Ser Thr Leu Pro Ala Met Phe Pro Thr His Ile
370                 375                 380 cgt tac agc gcg ctg gcg gcg gca ttt aat att tcg gtg ctg gtt gcc       1200
Arg Tyr Ser Ala Leu Ala Ala Ala Phe Asn Ile Ser Val Leu Val Ala
385                 390                 395                 400 ggt ctg acg cca acg ctg gcg gcc tgg ctg gtc gaa agc tcg cag aat       1248
Gly Leu Thr Pro Thr Leu Ala Ala Trp Leu Val Glu Ser Ser Gln Asn
                405                 410                 415 ctg atg atg cct gcc tat tac ctg atg gta gtg gcg gtg gtt ggt tta       1296
Leu Met Met Pro Ala Tyr Tyr Leu Met Val Val Ala Val Val Gly Leu
            420                 425                 430 atc acc ggc gta acc atg aaa gag acg gca aat cgt ccg ttg aaa ggt       1344
Ile Thr Gly Val Thr Met Lys Glu Thr Ala Asn Arg Pro Leu Lys Gly
        435                 440                 445 gcg aca ccg gcg gcg tca gat ata cag gaa gcg aag gaa att ctc gtc       1392
Ala Thr Pro Ala Ala Ser Asp Ile Gln Glu Ala Lys Glu Ile Leu Val
450                 455                 460 gag cat cac gat aat atc gag cag aaa atc gat gat att gac cac gag       1440
Glu His His Asp Asn Ile Glu Gln Lys Ile Asp Asp Ile Asp His Glu
465                 470                 475                 480 att gcc gat ttg cag gcg aaa cgt acc cgc ctg gtg cag caa cat ccg       1488
Ile Ala Asp Leu Gln Ala Lys Arg Thr Arg Leu Val Gln Gln His Pro
                485                 490                 495 cga att gat gaa taa                                                    1503
Arg Ile Asp Glu
            500

<210> SEQ ID NO 16
<211> LENGTH: 500
<212> TYPE: PRT
<213> ORGANISM: Escherichia coli

<400> SEQUENCE: 16

Met Leu Lys Arg Lys Lys Val Lys Pro Ile Thr Leu Arg Asp Val Thr
1               5                   10                  15

Ile Ile Asp Asp Gly Lys Leu Arg Lys Ala Ile Thr Ala Ala Ser Leu
            20                  25                  30

Gly Asn Ala Met Glu Trp Phe Asp Phe Gly Val Tyr Gly Phe Val Ala
        35                  40                  45
```

```
Tyr Ala Leu Gly Lys Val Phe Phe Pro Gly Ala Asp Pro Ser Val Gln
         50                  55                  60

Met Val Ala Ala Leu Ala Thr Phe Ser Val Pro Phe Leu Ile Arg Pro
 65                  70                  75                  80

Leu Gly Gly Leu Phe Phe Gly Met Leu Gly Asp Lys Tyr Gly Arg Gln
                     85                  90                  95

Lys Ile Leu Ala Ile Thr Ile Val Ile Met Ser Ile Ser Thr Phe Cys
                100                 105                 110

Ile Gly Leu Ile Pro Ser Tyr Asp Thr Ile Gly Ile Trp Ala Pro Ile
                115                 120                 125

Leu Leu Leu Ile Cys Lys Met Ala Gln Gly Phe Ser Val Gly Gly Glu
        130                 135                 140

Tyr Thr Gly Ala Ser Ile Phe Val Ala Glu Tyr Ser Pro Asp Arg Lys
145                 150                 155                 160

Arg Gly Phe Met Gly Ser Trp Leu Asp Phe Gly Ser Ile Ala Gly Phe
                165                 170                 175

Val Leu Gly Ala Gly Val Val Leu Ile Ser Thr Ile Val Gly Glu
                180                 185                 190

Ala Asn Phe Leu Asp Trp Gly Trp Arg Ile Pro Phe Phe Ile Ala Leu
                195                 200                 205

Pro Leu Gly Ile Ile Gly Leu Tyr Leu Arg His Ala Leu Glu Glu Thr
        210                 215                 220

Pro Ala Phe Gln Gln His Val Asp Lys Leu Glu Gln Gly Asp Arg Glu
225                 230                 235                 240

Gly Leu Gln Asp Gly Pro Lys Val Ser Phe Lys Glu Ile Ala Thr Lys
                245                 250                 255

Tyr Trp Arg Ser Leu Leu Thr Cys Ile Gly Leu Val Ile Ala Thr Asn
                260                 265                 270

Val Thr Tyr Tyr Met Leu Leu Thr Tyr Met Pro Ser Tyr Leu Ser His
        275                 280                 285

Asn Leu His Tyr Ser Glu Asp His Gly Val Leu Ile Ile Ala Ile
        290                 295                 300

Met Ile Gly Met Leu Phe Val Gln Pro Val Met Gly Leu Leu Ser Asp
305                 310                 315                 320

Arg Phe Gly Arg Arg Pro Phe Val Leu Leu Gly Ser Val Ala Leu Phe
                325                 330                 335

Val Leu Ala Ile Pro Ala Phe Ile Leu Ile Asn Ser Asn Val Ile Gly
                340                 345                 350

Leu Ile Phe Ala Gly Leu Leu Met Leu Ala Val Ile Leu Asn Cys Phe
        355                 360                 365

Thr Gly Val Met Ala Ser Thr Leu Pro Ala Met Phe Pro Thr His Ile
        370                 375                 380

Arg Tyr Ser Ala Leu Ala Ala Ala Phe Asn Ile Ser Val Leu Val Ala
385                 390                 395                 400

Gly Leu Thr Pro Thr Leu Ala Ala Trp Leu Val Glu Ser Ser Gln Asn
                405                 410                 415

Leu Met Met Pro Ala Tyr Tyr Leu Met Val Ala Val Val Gly Leu
                420                 425                 430

Ile Thr Gly Val Thr Met Lys Glu Thr Ala Asn Arg Pro Leu Lys Gly
            435                 440                 445

Ala Thr Pro Ala Ala Ser Asp Ile Gln Glu Ala Lys Glu Ile Leu Val
    450                 455                 460
```

```
Glu His His Asp Asn Ile Glu Gln Lys Ile Asp Asp Ile Asp His Glu
465                 470                 475                 480

Ile Ala Asp Leu Gln Ala Lys Arg Thr Arg Leu Val Gln Gln His Pro
                485                 490                 495

Arg Ile Asp Glu
            500

<210> SEQ ID NO 17
<211> LENGTH: 1452
<212> TYPE: DNA
<213> ORGANISM: Escherichia coli
<220> FEATURE:
<221> NAME/KEY: CDS
<222> LOCATION: (1)..(1452)
<223> OTHER INFORMATION: Kodierregion proP M7-Allel (Deletion von 51bp
      von Nukleotidposition 1173 bis 1223

<400> SEQUENCE: 17 atg ctg aaa agg aaa aaa gta aaa ccg att acc ctt cgt gat gtc acc      48
Met Leu Lys Arg Lys Lys Val Lys Pro Ile Thr Leu Arg Asp Val Thr
1               5                   10                  15 att att gat gac ggt aaa ctg cgt aaa gcc att acc gca gca tca ctg      96
Ile Ile Asp Asp Gly Lys Leu Arg Lys Ala Ile Thr Ala Ala Ser Leu
            20                  25                  30 ggt aat gca atg gaa tgg ttc gat ttt ggt gtt tat ggt ttt gtt gct    144
Gly Asn Ala Met Glu Trp Phe Asp Phe Gly Val Tyr Gly Phe Val Ala
        35                  40                  45 tac gca tta ggt aaa gtt ttt ttc ccg ggg gct gac ccc agc gtg cag    192
Tyr Ala Leu Gly Lys Val Phe Phe Pro Gly Ala Asp Pro Ser Val Gln
    50                  55                  60 atg gtt gct gca ctt gcc act ttc tcc gtt ccc ttt ctg att cga ccg    240
Met Val Ala Ala Leu Ala Thr Phe Ser Val Pro Phe Leu Ile Arg Pro
65                  70                  75                  80 ctt ggc gga ctc ttc ttt ggt atg ttg ggc gat aaa tat ggt cgc cag    288
Leu Gly Gly Leu Phe Phe Gly Met Leu Gly Asp Lys Tyr Gly Arg Gln
                85                  90                  95 aag atc ctc gct atc act att gtg att atg tcg atc agt acg ttc tgt    336
Lys Ile Leu Ala Ile Thr Ile Val Ile Met Ser Ile Ser Thr Phe Cys
            100                 105                 110 att ggc tta ata ccg tcc tac gac acg att ggt att tgg gca ccg att    384
Ile Gly Leu Ile Pro Ser Tyr Asp Thr Ile Gly Ile Trp Ala Pro Ile
        115                 120                 125 ctg ctg ttg atc tgt aag atg gca caa ggt ttc tcg gtc ggc ggt gaa    432
Leu Leu Leu Ile Cys Lys Met Ala Gln Gly Phe Ser Val Gly Gly Glu
    130                 135                 140 tat acc ggg gcg tcg ata ttt gtt gcg gaa tac tcc cct gac cgt aaa    480
Tyr Thr Gly Ala Ser Ile Phe Val Ala Glu Tyr Ser Pro Asp Arg Lys
145                 150                 155                 160 cgt ggc ttt atg ggc agc tgg ctg gac ttc ggt tct att gcc ggg ttt    528
Arg Gly Phe Met Gly Ser Trp Leu Asp Phe Gly Ser Ile Ala Gly Phe
                165                 170                 175 gtg ctg ggt gcg ggc gtg gtg gta tta att tcg acc att gtc ggc gaa    576
Val Leu Gly Ala Gly Val Val Val Leu Ile Ser Thr Ile Val Gly Glu
            180                 185                 190 gcg aac ttc ctc gat tgg ggc tgg cgt att ccg ttc ttt atc gct ctg    624
Ala Asn Phe Leu Asp Trp Gly Trp Arg Ile Pro Phe Phe Ile Ala Leu
        195                 200                 205 ccg tta ggg att atc ggg ctt tac ctg cgc cat gcg ctg gaa gag act    672
Pro Leu Gly Ile Ile Gly Leu Tyr Leu Arg His Ala Leu Glu Glu Thr
    210                 215                 220 ccg gcg ttc cag cag cat gtc gat aaa ctg gaa cag ggc gac cgt gaa    720
Pro Ala Phe Gln Gln His Val Asp Lys Leu Glu Gln Gly Asp Arg Glu
```

```
Pro Ala Phe Gln Gln His Val Asp Lys Leu Glu Gln Gly Asp Arg Glu
225                 230                 235                 240 ggt ttg cag gat ggc ccg aaa gtc tcg ttt aaa gag att gcc act aaa     768
Gly Leu Gln Asp Gly Pro Lys Val Ser Phe Lys Glu Ile Ala Thr Lys
                245                 250                 255 tac tgg cgc agc ctg ttg aca tgt att ggt ctg gta att gcc acc aac     816
Tyr Trp Arg Ser Leu Leu Thr Cys Ile Gly Leu Val Ile Ala Thr Asn
            260                 265                 270 gtg act tac tac atg ttg ctg acc tat atg ccg agt tat ttg tcg cat     864
Val Thr Tyr Tyr Met Leu Leu Thr Tyr Met Pro Ser Tyr Leu Ser His
        275                 280                 285 aac ctg cat tac tcc gaa gac cac ggg gtg ctg att att atc gcc att     912
Asn Leu His Tyr Ser Glu Asp His Gly Val Leu Ile Ile Ile Ala Ile
    290                 295                 300 atg atc ggt atg ctg ttt gtc cag ccg gtg atg ggc ttg ctg agt gac     960
Met Ile Gly Met Leu Phe Val Gln Pro Val Met Gly Leu Leu Ser Asp
305                 310                 315                 320 cgt ttt ggc cgt cgt ccg ttt gtg cta ctt ggt agt gtt gcc ctg ttt    1008
Arg Phe Gly Arg Arg Pro Phe Val Leu Leu Gly Ser Val Ala Leu Phe
                325                 330                 335 gtg ttg gcg atc ccg gcg ttt att ctg att aac agt aac gtc atc ggc    1056
Val Leu Ala Ile Pro Ala Phe Ile Leu Ile Asn Ser Asn Val Ile Gly
            340                 345                 350 ctg att ttt gcc ggg tta ctg atg ctg gcg gtg atc ctt aac tgc ttt    1104
Leu Ile Phe Ala Gly Leu Leu Met Leu Ala Val Ile Leu Asn Cys Phe
        355                 360                 365 acg ggc gtt atg gct tct acc ttg cca gcg atg ttc ccg acg cat atc    1152
Thr Gly Val Met Ala Ser Thr Leu Pro Ala Met Phe Pro Thr His Ile
370                 375                 380 cgt tac agc gcg ctg gcg gcc tgg ctg gtc gaa agc tcg cag aat ctg    1200
Arg Tyr Ser Ala Leu Ala Ala Trp Leu Val Glu Ser Ser Gln Asn Leu
385                 390                 395                 400 atg atg cct gcc tat tac ctg atg gta gtg gcg gtg gtt ggt tta atc    1248
Met Met Pro Ala Tyr Tyr Leu Met Val Val Ala Val Val Gly Leu Ile
                405                 410                 415 acc ggc gta acc atg aaa gag acg gca aat cgt ccg ttg aaa ggt gcg    1296
Thr Gly Val Thr Met Lys Glu Thr Ala Asn Arg Pro Leu Lys Gly Ala
            420                 425                 430 aca ccg gcg gcg tca gat ata cag gaa gcg aag gaa att ctc gtc gag    1344
Thr Pro Ala Ala Ser Asp Ile Gln Glu Ala Lys Glu Ile Leu Val Glu
        435                 440                 445 cat tac gat aat atc gag cag aaa atc gat gat att gac cac gag att    1392
His Tyr Asp Asn Ile Glu Gln Lys Ile Asp Asp Ile Asp His Glu Ile
    450                 455                 460 gcc gat ttg cag gcg aaa cgt acc cgc ctg gtg cag caa cat ccg cga    1440
Ala Asp Leu Gln Ala Lys Arg Thr Arg Leu Val Gln Gln His Pro Arg
465                 470                 475                 480 att gat gaa taa                                                    1452
Ile Asp Glu <210> SEQ ID NO 18
<211> LENGTH: 483
<212> TYPE: PRT
<213> ORGANISM: Escherichia coli

<400> SEQUENCE: 18

Met Leu Lys Arg Lys Lys Val Lys Pro Ile Thr Leu Arg Asp Val Thr
1               5                   10                  15

Ile Ile Asp Asp Gly Lys Leu Arg Lys Ala Ile Thr Ala Ala Ser Leu
            20                  25                  30
```

```
Gly Asn Ala Met Glu Trp Phe Asp Phe Gly Tyr Gly Phe Val Ala
        35                  40                  45

Tyr Ala Leu Gly Lys Val Phe Phe Pro Gly Ala Asp Pro Ser Val Gln
 50                  55                  60

Met Val Ala Ala Leu Ala Thr Phe Ser Val Pro Phe Leu Ile Arg Pro
 65                  70                  75                  80

Leu Gly Gly Leu Phe Phe Gly Met Leu Gly Asp Lys Tyr Gly Arg Gln
                 85                  90                  95

Lys Ile Leu Ala Ile Thr Ile Val Ile Met Ser Ile Ser Thr Phe Cys
                100                 105                 110

Ile Gly Leu Ile Pro Ser Tyr Asp Thr Ile Gly Ile Trp Ala Pro Ile
                115                 120                 125

Leu Leu Leu Ile Cys Lys Met Ala Gln Gly Phe Ser Val Gly Gly Glu
            130                 135                 140

Tyr Thr Gly Ala Ser Ile Phe Val Ala Glu Tyr Ser Pro Asp Arg Lys
145                 150                 155                 160

Arg Gly Phe Met Gly Ser Trp Leu Asp Phe Gly Ser Ile Ala Gly Phe
                165                 170                 175

Val Leu Gly Ala Gly Val Val Leu Ile Ser Thr Ile Val Gly Glu
                180                 185                 190

Ala Asn Phe Leu Asp Trp Gly Trp Arg Ile Pro Phe Phe Ile Ala Leu
            195                 200                 205

Pro Leu Gly Ile Ile Gly Leu Tyr Leu Arg His Ala Leu Glu Glu Thr
210                 215                 220

Pro Ala Phe Gln Gln His Val Asp Lys Leu Glu Gln Gly Asp Arg Glu
225                 230                 235                 240

Gly Leu Gln Asp Gly Pro Lys Val Ser Phe Lys Glu Ile Ala Thr Lys
                245                 250                 255

Tyr Trp Arg Ser Leu Leu Thr Cys Ile Gly Leu Val Ile Ala Thr Asn
                260                 265                 270

Val Thr Tyr Tyr Met Leu Leu Thr Tyr Met Pro Ser Tyr Leu Ser His
            275                 280                 285

Asn Leu His Tyr Ser Glu Asp His Gly Val Leu Ile Ile Ile Ala Ile
            290                 295                 300

Met Ile Gly Met Leu Phe Val Gln Pro Val Met Gly Leu Leu Ser Asp
305                 310                 315                 320

Arg Phe Gly Arg Arg Pro Phe Val Leu Leu Gly Ser Val Ala Leu Phe
                325                 330                 335

Val Leu Ala Ile Pro Ala Phe Ile Leu Ile Asn Ser Asn Val Ile Gly
                340                 345                 350

Leu Ile Phe Ala Gly Leu Leu Met Leu Ala Val Ile Leu Asn Cys Phe
            355                 360                 365

Thr Gly Val Met Ala Ser Thr Leu Pro Ala Met Phe Pro Thr His Ile
370                 375                 380

Arg Tyr Ser Ala Leu Ala Ala Trp Leu Val Glu Ser Ser Gln Asn Leu
385                 390                 395                 400

Met Met Pro Ala Tyr Tyr Leu Met Val Val Ala Val Gly Leu Ile
                405                 410                 415

Thr Gly Val Thr Met Lys Glu Thr Ala Asn Arg Pro Leu Lys Gly Ala
                420                 425                 430

Thr Pro Ala Ala Ser Asp Ile Gln Glu Ala Lys Glu Ile Leu Val Glu
                435                 440                 445
```

-continued

```
His Tyr Asp Asn Ile Glu Gln Lys Ile Asp Asp Ile Asp His Glu Ile
    450                 455                 460
Ala Asp Leu Gln Ala Lys Arg Thr Arg Leu Val Gln Gln His Pro Arg
465                 470                 475                 480
Ile Asp Glu

<210> SEQ ID NO 19
<211> LENGTH: 1522
<212> TYPE: DNA
<213> ORGANISM: Escherichia coli
<220> FEATURE:
<221> NAME/KEY: CDS
<222> LOCATION: (1)..(1014)
<223> OTHER INFORMATION: Kodierregion proP M6-Allel (19bp Insertion nach
      Nukleotidposition 973)

<400> SEQUENCE: 19 atg ctg aaa agg aaa aaa gta aaa ccg att acc ctt cgt gat gtc acc      48
Met Leu Lys Arg Lys Lys Val Lys Pro Ile Thr Leu Arg Asp Val Thr
1               5                  10                  15 att att gat gac ggt aaa ctg cgt aaa gcc att acc gca gca tca ctg      96
Ile Ile Asp Asp Gly Lys Leu Arg Lys Ala Ile Thr Ala Ala Ser Leu
            20                  25                  30 ggt aat gca atg gaa tgg ttc gat ttt ggt gtt tat ggt ttt gtt gct     144
Gly Asn Ala Met Glu Trp Phe Asp Phe Gly Val Tyr Gly Phe Val Ala
        35                  40                  45 tac gca tta ggt aaa gtt ttt ttc ccg ggg gct gac ccc agc gtg cag     192
Tyr Ala Leu Gly Lys Val Phe Phe Pro Gly Ala Asp Pro Ser Val Gln
    50                  55                  60 atg gtt gct gca ctt gcc act ttc tcc gtt ccc ttt ctg att cga ccg     240
Met Val Ala Ala Leu Ala Thr Phe Ser Val Pro Phe Leu Ile Arg Pro
65                  70                  75                  80 ctt ggc gga ctc ttc ttt ggt atg ttg ggc gat aaa tat ggt cgc cag     288
Leu Gly Gly Leu Phe Phe Gly Met Leu Gly Asp Lys Tyr Gly Arg Gln
                85                  90                  95 aag atc ctc gct atc act att gtg att atg tcg atc agt acg ttc tgt     336
Lys Ile Leu Ala Ile Thr Ile Val Ile Met Ser Ile Ser Thr Phe Cys
            100                 105                 110 att ggc tta ata ccg tcc tac gac acg att ggt att tgg gca ccg att     384
Ile Gly Leu Ile Pro Ser Tyr Asp Thr Ile Gly Ile Trp Ala Pro Ile
        115                 120                 125 ctg ctg ttg atc tgt aag atg gca caa ggt ttc tcg gtc ggc ggt gaa     432
Leu Leu Leu Ile Cys Lys Met Ala Gln Gly Phe Ser Val Gly Gly Glu
    130                 135                 140 tat acc ggg gcg tcg ata ttt gtt gcg gaa tac tcc cct gac cgt aaa     480
Tyr Thr Gly Ala Ser Ile Phe Val Ala Glu Tyr Ser Pro Asp Arg Lys
145                 150                 155                 160 cgt ggc ttt atg ggc agc tgg ctg gac ttc ggt tct att gcc ggg ttt     528
Arg Gly Phe Met Gly Ser Trp Leu Asp Phe Gly Ser Ile Ala Gly Phe
                165                 170                 175 gtg ctg ggt gcg ggc gtg gtg gtg tta att tcg acc att gtc ggc gaa     576
Val Leu Gly Ala Gly Val Val Val Leu Ile Ser Thr Ile Val Gly Glu
            180                 185                 190 gcg aac ttc ctc gat tgg ggc tgg cgt att ccg ttc ttt atc gct ctg     624
Ala Asn Phe Leu Asp Trp Gly Trp Arg Ile Pro Phe Phe Ile Ala Leu
        195                 200                 205 ccg tta ggg att atc ggg ctt tac ctg cgc cat gcg ctg gaa gag act     672
Pro Leu Gly Ile Ile Gly Leu Tyr Leu Arg His Ala Leu Glu Glu Thr
    210                 215                 220 ccg gcg ttc cag cag cat gtc gat aaa ctg gaa cag ggc gac cgt gaa     720
Pro Ala Phe Gln Gln His Val Asp Lys Leu Glu Gln Gly Asp Arg Glu
```

```
                225                 230                 235                 240
ggt ttg cag gat ggc ccg aaa gtc tcg ttt aaa gag att gcc act aaa        768
Gly Leu Gln Asp Gly Pro Lys Val Ser Phe Lys Glu Ile Ala Thr Lys
                245                 250                 255 tac tgg cgc agc ctg ttg aca tgt att ggt ctg gta att gcc acc aac        816
Tyr Trp Arg Ser Leu Leu Thr Cys Ile Gly Leu Val Ile Ala Thr Asn
            260                 265                 270 gtg act tac tac atg ttg ctg acc tat atg ccg agt tat ttg tcg cat        864
Val Thr Tyr Tyr Met Leu Leu Thr Tyr Met Pro Ser Tyr Leu Ser His
        275                 280                 285 aac ctg cat tac tcc gaa gac cac ggg gtg ctg att att atc gcc att        912
Asn Leu His Tyr Ser Glu Asp His Gly Val Leu Ile Ile Ile Ala Ile
    290                 295                 300 atg atc ggt atg ctg ttt gtc cag ccg gtg atg ggc ttg ctg agt gac        960
Met Ile Gly Met Leu Phe Val Gln Pro Val Met Gly Leu Leu Ser Asp
305                 310                 315                 320 cgt ttt ggc cgt cgt ccg ttt gtg cta ctt gcg tcc gtt tgt gct act       1008
Arg Phe Gly Arg Arg Pro Phe Val Leu Leu Ala Ser Val Cys Ala Thr
                325                 330                 335 tgg tag tgttgccctg tttgtgttgg cgatcccggc gtttattctg attaacagta        1064
Trp acgtcatcgg cctgattttt gccgggttac tgatgctggc ggtgatcctt aactgcttta     1124
cgggcgttat ggcttctacc ttgccagcga tgttcccgac gcatatccgt tacagcgcgc     1184 tgcggcggc atttaatatt tcggtgctgg ttgccggtct gacgccaacg ctggcggcct      1244
ggctggtcga agctcgcag aatctgatga tgcctgccta ttacctgatg gtagtggcgg      1304
tggttggttt aatcaccggc gtaaccatga agagacggc aaatcgtccg ttgaaaggtg      1364
cgacaccggc ggcgtcagat atacaggaag cgaaggaaat tctcgtcgag cattacgata     1424
atatcgagca gaaatcgat gatattgacc acgagattgc cgatttgcag gcgaaacgta     1484
cccgcctggt gcagcaacat ccgcgaattg atgaataa                            1522
```

<210> SEQ ID NO 20
<211> LENGTH: 337
<212> TYPE: PRT
<213> ORGANISM: Escherichia coli

<400> SEQUENCE: 20

```
Met Leu Lys Arg Lys Lys Val Lys Pro Ile Thr Leu Arg Asp Val Thr
1               5                   10                  15

Ile Ile Asp Asp Gly Lys Leu Arg Lys Ala Ile Thr Ala Ala Ser Leu
            20                  25                  30

Gly Asn Ala Met Glu Trp Phe Asp Phe Gly Val Tyr Gly Phe Val Ala
        35                  40                  45

Tyr Ala Leu Gly Lys Val Phe Phe Pro Gly Ala Asp Pro Ser Val Gln
    50                  55                  60

Met Val Ala Ala Leu Ala Thr Phe Ser Val Pro Phe Leu Ile Arg Pro
65                  70                  75                  80

Leu Gly Gly Leu Phe Phe Gly Met Leu Gly Asp Lys Tyr Gly Arg Gln
                85                  90                  95

Lys Ile Leu Ala Ile Thr Ile Val Met Ser Ile Ser Thr Phe Cys
            100                 105                 110

Ile Gly Leu Ile Pro Ser Tyr Asp Thr Ile Gly Ile Trp Ala Pro Ile
        115                 120                 125

Leu Leu Leu Ile Cys Lys Met Ala Gln Gly Phe Ser Val Gly Gly Glu
    130                 135                 140
```

```
Tyr Thr Gly Ala Ser Ile Phe Val Ala Glu Tyr Ser Pro Asp Arg Lys
145                 150                 155                 160

Arg Gly Phe Met Gly Ser Trp Leu Asp Phe Gly Ser Ile Ala Gly Phe
            165                 170                 175

Val Leu Gly Ala Gly Val Val Leu Ile Ser Thr Ile Val Gly Glu
        180                 185                 190

Ala Asn Phe Leu Asp Trp Gly Trp Arg Ile Pro Phe Ile Ala Leu
        195                 200                 205

Pro Leu Gly Ile Ile Gly Leu Tyr Leu Arg His Ala Leu Glu Glu Thr
    210                 215                 220

Pro Ala Phe Gln Gln His Val Asp Lys Leu Gln Gly Asp Arg Glu
225             230                 235                 240

Gly Leu Gln Asp Gly Pro Lys Val Ser Phe Lys Glu Ile Ala Thr Lys
                245                 250                 255

Tyr Trp Arg Ser Leu Leu Thr Cys Ile Gly Leu Val Ile Ala Thr Asn
            260                 265                 270

Val Thr Tyr Tyr Met Leu Leu Thr Tyr Met Pro Ser Tyr Leu Ser His
        275                 280                 285

Asn Leu His Tyr Ser Glu Asp His Gly Val Leu Ile Ile Ala Ile
        290                 295                 300

Met Ile Gly Met Leu Phe Val Gln Pro Val Met Gly Leu Leu Ser Asp
305             310                 315                 320

Arg Phe Gly Arg Pro Phe Val Leu Leu Ala Ser Val Cys Ala Thr
                325                 330                 335

Trp

<210> SEQ ID NO 21
<211> LENGTH: 1503
<212> TYPE: DNA
<213> ORGANISM: Escherichia coli
<220> FEATURE:
<221> NAME/KEY: CDS
<222> LOCATION: (1)..(1503)
<223> OTHER INFORMATION: Kodierregion proP M5-Allel (Austausch g zu t an
      Position 971 bedingt AA-Austausch R324L)

<400> SEQUENCE: 21 atg ctg aaa agg aaa aaa gta aaa ccg att acc ctt cgt gat gtc acc      48
Met Leu Lys Arg Lys Lys Val Lys Pro Ile Thr Leu Arg Asp Val Thr
1               5                   10                  15 att att gat gac ggt aaa ctg cgt aaa gcc att acc gca gca tca ctg      96
Ile Ile Asp Asp Gly Lys Leu Arg Lys Ala Ile Thr Ala Ala Ser Leu
            20                  25                  30 ggt aat gca atg gaa tgg ttc gat ttt ggt gtt tat ggt ttt gtt gct     144
Gly Asn Ala Met Glu Trp Phe Asp Phe Gly Val Tyr Gly Phe Val Ala
        35                  40                  45 tac gca tta ggt aaa gtt ttt ttc ccg ggg gct gac ccc agc gtg cag     192
Tyr Ala Leu Gly Lys Val Phe Phe Pro Gly Ala Asp Pro Ser Val Gln
    50                  55                  60 atg gtt gct gca ctt gcc act ttc tcc gtt ccc ttt ctg att cga ccg     240
Met Val Ala Ala Leu Ala Thr Phe Ser Val Pro Phe Leu Ile Arg Pro
65                  70                  75                  80 ctt ggc gga ctc ttc ttt ggt atg ttg ggc gat aaa tat ggt cgc cag     288
Leu Gly Gly Leu Phe Phe Gly Met Leu Gly Asp Lys Tyr Gly Arg Gln
                85                  90                  95 aag atc ctc gct atc act att gtg att atg tcg atc agt acg ttc tgt     336
Lys Ile Leu Ala Ile Thr Ile Val Ile Met Ser Ile Ser Thr Phe Cys
            100                 105                 110
```

| | | |
|---|---|---|
| att ggc tta ata ccg tcc tac gac acg att ggt att tgg gca ccg att<br>Ile Gly Leu Ile Pro Ser Tyr Asp Thr Ile Gly Ile Trp Ala Pro Ile<br>             115                    120                    125 | | 384 |
| ctg ctg ttg atc tgt aag atg gca caa ggt ttc tcg gtc ggc ggt gaa<br>Leu Leu Leu Ile Cys Lys Met Ala Gln Gly Phe Ser Val Gly Gly Glu<br>130                    135                    140 | | 432 |
| tat acc ggg gcg tcg ata ttt gtt gcg gaa tac tcc cct gac cgt aaa<br>Tyr Thr Gly Ala Ser Ile Phe Val Ala Glu Tyr Ser Pro Asp Arg Lys<br>145                    150                    155                    160 | | 480 |
| cgt ggc ttt atg ggc agc tgg ctg gac ttc ggt tct att gcc ggg ttt<br>Arg Gly Phe Met Gly Ser Trp Leu Asp Phe Gly Ser Ile Ala Gly Phe<br>                    165                    170                    175 | | 528 |
| gtg ctg ggt gcg ggc gtg gtg gtg tta att tcg acc att gtc ggc gaa<br>Val Leu Gly Ala Gly Val Val Val Leu Ile Ser Thr Ile Val Gly Glu<br>                        180                    185                    190 | | 576 |
| gcg aac ttc ctc gat tgg ggc tgg cgt att ccg ttc ttt atc gct ctg<br>Ala Asn Phe Leu Asp Trp Gly Trp Arg Ile Pro Phe Phe Ile Ala Leu<br>                    195                    200                    205 | | 624 |
| ccg tta ggg att atc ggg ctt tac ctg cgc cat gcg ctg gaa gag act<br>Pro Leu Gly Ile Ile Gly Leu Tyr Leu Arg His Ala Leu Glu Glu Thr<br>                    210                    215                    220 | | 672 |
| ccg gcg ttc cag cag cat gtc gat aaa ctg gaa cag ggc gac cgt gaa<br>Pro Ala Phe Gln Gln His Val Asp Lys Leu Glu Gln Gly Asp Arg Glu<br>225                    230                    235                    240 | | 720 |
| ggt ttg cag gat ggc ccg aaa gtc tcg ttt aaa gag att gcc act aaa<br>Gly Leu Gln Asp Gly Pro Lys Val Ser Phe Lys Glu Ile Ala Thr Lys<br>                        245                    250                    255 | | 768 |
| tac tgg cgc agc ctg tta aca tgt att ggt ctg gta att gcc acc aac<br>Tyr Trp Arg Ser Leu Leu Thr Cys Ile Gly Leu Val Ile Ala Thr Asn<br>                    260                    265                    270 | | 816 |
| gtg act tac tac atg ttg ctg acc tat atg ccg agt tat ttg tcg cat<br>Val Thr Tyr Tyr Met Leu Leu Thr Tyr Met Pro Ser Tyr Leu Ser His<br>              275                    280                    285 | | 864 |
| aac ctg cat tac tcc gaa gac cac ggg gtg ctg att att atc gcc att<br>Asn Leu His Tyr Ser Glu Asp His Gly Val Leu Ile Ile Ile Ala Ile<br>        290                    295                    300 | | 912 |
| atg atc ggt atg ctg ttt gtc cag ccg gtg atg ggc ttg ctg agt gac<br>Met Ile Gly Met Leu Phe Val Gln Pro Val Met Gly Leu Leu Ser Asp<br>305                    310                    315                    320 | | 960 |
| cgt ttt ggc ctt cgt ccg ttt gtg cta ctt ggt agt gtt gcc ctg ttt<br>Arg Phe Gly Leu Arg Pro Phe Val Leu Leu Gly Ser Val Ala Leu Phe<br>                        325                    330                    335 | | 1008 |
| gtg ttg gcg atc ccg gcg ttt att ctg att aac agt aac gtc atc ggc<br>Val Leu Ala Ile Pro Ala Phe Ile Leu Ile Asn Ser Asn Val Ile Gly<br>                        340                    345                    350 | | 1056 |
| ctg att ttt gcc ggg tta ctg atg ctg gcg gtg atc ctt aac tgc ttt<br>Leu Ile Phe Ala Gly Leu Leu Met Leu Ala Val Ile Leu Asn Cys Phe<br>              355                    360                    365 | | 1104 |
| acg ggc gtt atg gct tct acc ttg cca gcg atg ttc ccg acg cat atc<br>Thr Gly Val Met Ala Ser Thr Leu Pro Ala Met Phe Pro Thr His Ile<br>        370                    375                    380 | | 1152 |
| cgt tac agc gcg ctg gcg gcg gca ttt aat att tcg gtg ctg gtt gcc<br>Arg Tyr Ser Ala Leu Ala Ala Ala Phe Asn Ile Ser Val Leu Val Ala<br>385                    390                    395                    400 | | 1200 |
| ggt ctg acg cca acg ctg gcg gcc tgg ctg gtc gaa agc tcg cag aat<br>Gly Leu Thr Pro Thr Leu Ala Ala Trp Leu Val Glu Ser Ser Gln Asn<br>                        405                    410                    415 | | 1248 |
| ctg atg atg cct gcc tat tac ctg atg gta gtg gcg gtg gtt ggt tta<br>Leu Met Met Pro Ala Tyr Tyr Leu Met Val Val Ala Val Val Gly Leu | | 1296 |

```
                420                 425                 430
atc acc ggc gta acc atg aaa gag acg gca aat cgt ccg ttg aaa ggt      1344
Ile Thr Gly Val Thr Met Lys Glu Thr Ala Asn Arg Pro Leu Lys Gly
            435                 440                 445 gcg aca ccg gcg gcg tca gat ata cag gaa gcg aag gaa att ctc gtc      1392
Ala Thr Pro Ala Ala Ser Asp Ile Gln Glu Ala Lys Glu Ile Leu Val
450                 455                 460 gag cat tac gat aat atc gag cag aaa atc gat gat att gac cac gag      1440
Glu His Tyr Asp Asn Ile Glu Gln Lys Ile Asp Asp Ile Asp His Glu
465                 470                 475                 480 att gcc gat ttg cag gcg aaa cgt acc cgc ctg gtg cag caa cat ccg      1488
Ile Ala Asp Leu Gln Ala Lys Arg Thr Arg Leu Val Gln Gln His Pro
                485                 490                 495 cga att gat gaa taa                                                  1503
Arg Ile Asp Glu
            500
```

<210> SEQ ID NO 22
<211> LENGTH: 500
<212> TYPE: PRT
<213> ORGANISM: Escherichia coli

<400> SEQUENCE: 22

```
Met Leu Lys Arg Lys Val Lys Pro Ile Thr Leu Arg Asp Val Thr
1               5                   10                  15

Ile Ile Asp Asp Gly Lys Leu Arg Lys Ala Ile Thr Ala Ala Ser Leu
                20                  25                  30

Gly Asn Ala Met Glu Trp Phe Asp Phe Gly Val Tyr Gly Phe Val Ala
            35                  40                  45

Tyr Ala Leu Gly Lys Val Phe Phe Pro Gly Ala Asp Pro Ser Val Gln
50                  55                  60

Met Val Ala Ala Leu Ala Thr Phe Ser Val Pro Phe Leu Ile Arg Pro
65                  70                  75                  80

Leu Gly Gly Leu Phe Phe Gly Met Leu Gly Asp Lys Tyr Gly Arg Gln
                85                  90                  95

Lys Ile Leu Ala Ile Thr Ile Val Ile Met Ser Ile Ser Thr Phe Cys
            100                 105                 110

Ile Gly Leu Ile Pro Ser Tyr Asp Thr Ile Gly Ile Trp Ala Pro Ile
        115                 120                 125

Leu Leu Leu Ile Cys Lys Met Ala Gln Gly Phe Ser Val Gly Gly Glu
    130                 135                 140

Tyr Thr Gly Ala Ser Ile Phe Val Ala Glu Tyr Ser Pro Asp Arg Lys
145                 150                 155                 160

Arg Gly Phe Met Gly Ser Trp Leu Asp Phe Gly Ser Ile Ala Gly Phe
                165                 170                 175

Val Leu Gly Ala Gly Val Val Leu Ile Ser Thr Ile Val Gly Glu
            180                 185                 190

Ala Asn Phe Leu Asp Trp Gly Trp Arg Ile Pro Phe Phe Ile Ala Leu
        195                 200                 205

Pro Leu Gly Ile Ile Gly Leu Tyr Leu Arg His Ala Leu Glu Glu Thr
    210                 215                 220

Pro Ala Phe Gln Gln His Val Asp Lys Leu Glu Gln Gly Asp Arg Glu
225                 230                 235                 240

Gly Leu Gln Asp Gly Pro Lys Val Ser Phe Lys Glu Ile Ala Thr Lys
                245                 250                 255

Tyr Trp Arg Ser Leu Leu Thr Cys Ile Gly Leu Val Ile Ala Thr Asn
```

```
                    260                 265                 270
    Val Thr Tyr Tyr Met Leu Leu Thr Tyr Met Pro Ser Tyr Leu Ser His
                275                 280                 285

Asn Leu His Tyr Ser Glu Asp His Gly Val Leu Ile Ile Ile Ala Ile
                290                 295                 300

Met Ile Gly Met Leu Phe Val Gln Pro Val Met Gly Leu Leu Ser Asp
    305                 310                 315                 320

Arg Phe Gly Leu Arg Pro Phe Val Leu Leu Gly Ser Val Ala Leu Phe
                    325                 330                 335

Val Leu Ala Ile Pro Ala Phe Ile Leu Ile Asn Ser Asn Val Ile Gly
                340                 345                 350

Leu Ile Phe Ala Gly Leu Leu Met Leu Ala Val Ile Leu Asn Cys Phe
                355                 360                 365

Thr Gly Val Met Ala Ser Thr Leu Pro Ala Met Phe Pro Thr His Ile
                370                 375                 380

Arg Tyr Ser Ala Leu Ala Ala Ala Phe Asn Ile Ser Val Leu Val Ala
    385                 390                 395                 400

Gly Leu Thr Pro Thr Leu Ala Ala Trp Leu Val Glu Ser Ser Gln Asn
                    405                 410                 415

Leu Met Met Pro Ala Tyr Tyr Leu Met Val Ala Val Val Gly Leu
                420                 425                 430

Ile Thr Gly Val Thr Met Lys Glu Thr Ala Asn Arg Pro Leu Lys Gly
                435                 440                 445

Ala Thr Pro Ala Ala Ser Asp Ile Gln Glu Ala Lys Glu Ile Leu Val
                450                 455                 460

Glu His Tyr Asp Asn Ile Glu Gln Lys Ile Asp Asp Ile Asp His Glu
    465                 470                 475                 480

Ile Ala Asp Leu Gln Ala Lys Arg Thr Arg Leu Val Gln Gln His Pro
                    485                 490                 495

Arg Ile Asp Glu
                500

<210> SEQ ID NO 23
<211> LENGTH: 2852
<212> TYPE: DNA
<213> ORGANISM: Escherichia coli
<220> FEATURE:
<221> NAME/KEY: CDS
<222> LOCATION: (1)..(243)
<223> OTHER INFORMATION: Kodierregion proP M2-Allel (1359bp Insertion
      nach Nukleotidposition 183)

<400> SEQUENCE: 23 atg ctg aaa agg aaa aaa gta aaa ccg att acc ctt cgt gat gtc acc       48
Met Leu Lys Arg Lys Lys Val Lys Pro Ile Thr Leu Arg Asp Val Thr
1               5                   10                  15 att att gat gac ggt aaa ctg cgt aaa gcc att acc gca gca tca ctg       96
Ile Ile Asp Asp Gly Lys Leu Arg Lys Ala Ile Thr Ala Ala Ser Leu
                20                  25                  30 ggt aat gca atg gaa tgg ttc gat ttt ggt gtt tat ggt ttt gtt gct      144
Gly Asn Ala Met Glu Trp Phe Asp Phe Gly Val Tyr Gly Phe Val Ala
            35                  40                  45 tac gca tta ggt aaa gtt ttt ttc ccg ggg gct gac ccc ata agc gct      192
Tyr Ala Leu Gly Lys Val Phe Phe Pro Gly Ala Asp Pro Ile Ser Ala
        50                  55                  60 aac tta agg gtt gaa cca tct gaa gaa tgc gac gcc tcg gtg cct cgt      240
Asn Leu Arg Val Glu Pro Ser Glu Glu Cys Asp Ala Ser Val Pro Arg
65                  70                  75                  80
```

```
taa gacgatgcct cgcgttcttc aattgcgttt tgtaggctgt cagggatact      293
gtcccacgaa tggccacctg taagctccag atgaccattt tgttattct ccacaacgag  353
ttagttcttc ttttcggatc cggcacttct ggggggggaaa tccagcgatg gctggattat 413
gtcgtcaatt aaaaatgcgg cgagtagatt agcaaatatc cacgctttcg cgagttcagg  473
ttcctttgca cgcaaagcat ccaggtgcag caaacttttg agccgcttaa aagccagttc  533
aatttgccat cgcagacggt aacaatcagc cacttgctct gctgaatatt catcttccgg  593
taatgatgtt agcaatagca catggcccgc tgcttccagc gtttccgcct gaactactcg  653
tcctttttcga cgattctcgc tgagcagtcg ggttttactg attaatgctt tttcgggagg  713
aagtgatacg gcaatgagac gtgccggaaa gggagctccg gctttttat tacctgaatt   773
gcctatcatt acagtggttt caccgttctt accgcaatcc agcccgcgca gaaaacccat  833
catgtcaaag cgcattcctt ctgcagttaa ccagcgcaat cctcgccagt gaacccggac  893
gatataatca gcttctccaa aagcaagtga gcggatacat tcgggacgcg aaccgaatcc  953
ccggtcagca atgcgtatct cgtctgccgt ttgcgcaaat cggtccagcc gttcagcgtc  1013
tctgctgtcg gttagctcaa aatcagtgaa ctgacaggta tgaggatcat atcccatatg  1073
tagtcgccat tcagcgctgc cgccccccggg cgcactgatt gctgttccat cgacaagacg  1133
caatctcttt ccgcttgtac aacccgtaac tgcggcgcgt acagcaagtg tttgtgcggc  1193
aagtatgcca aaccagtcgg cggcattccg cagccgcttc aggagagcca cgtcagataa  1253
tgttgcaacg tcatggagct gagcccatgc agtgacttca cgtaatgaca tcccccccggg 1313
gccgtaagcc agccccagac gtagcagagt tgcagcatca cgaatttcgc ggcggcgggt  1373
tagagccccg gcattacgtg ccgaagtatc cagttcttcg ggcttaccaa tatgggccag  1433
aattgctgac cagttatcgt gagagtaatt catcggcacg ttaaatcata tcaggcgtaa  1493
taccacaacc cttaagttag cgcttatggg gctgaccccca gcgtgcagat ggttgctgca  1553
cttgccactt tctccgttcc ctttctgatt cgaccgcttg gcggactctt ctttggtatg  1613
ttgggcgata aatatggtcg ccagaagatc ctcgctatca ctattgtgat tatgtcgatc  1673
agtacgttct gtattggctt aataccgtcc tacgacacga ttggtatttg ggcaccgatt  1733
ctgctgttga tctgtaagat ggcacaaggt ttctcggtcg gcggtgaata taccggggcg  1793
tcgatatttg ttgcggaata ctcccctgac cgtaaacgtg gctttatggg cagctggctg  1853
gacttcggtt ctattgccgg gtttgtgctg ggtgcgggcg tggtggtgtt aatttcgacc  1913
attgtcggcg aagcgaactt cctcgattgg ggctggcgta ttccgttctt tatcgctctg  1973
ccgttaggga ttatcgggct ttacctgcgc catgcgctgg aagagactcc ggcgttccag  2033
cagcatgtcg ataaactgga acagggcgac cgtgaaggtt tgcaggatgg cccgaaagtc  2093
tcgtttaaag agattgccac taaatactgg cgcagcctgt tgacatgtat tggtctggta  2153
attgccacca acgtgactta ctacatgttg ctgacctata tgccgagtta tttgtcgcat  2213
aacctgcatt actccgaaga ccacggggtg ctgattatta tcgccattat gatcggtatg  2273
ctgtttgtcc agccggtgat gggcttgctg agtgaccgtt ttggccgtcg tccgtttgtg  2333
ctacttggta gtgttgccct gtttgtgttg gcgatcccgg cgtttattct gattaacagt  2393
aacgtcatcg gcctgatttt tgccgggtta ctgatgctgg cggtgatcct taactgcttt  2453
acgggcgtta tggcttctac cttgccagcg atgttcccga cgcatatccg ttacagcgcg  2513
ctggcggcgg catttaatat ttcggtgctg gttgccggtc tgacgccaac gctggcggcc  2573
```

```
tggctggtcg aaagctcgca gaatctgatg atgcctgcct attacctgat ggtagtggcg    2633
gtggttggtt taatcaccgg cgtaaccatg aaagagacgg caaatcgtcc gttgaaaggt    2693
gcgacaccgg cggcgtcaga tatacaggaa gcgaaggaaa ttctcgtcga gcattacgat    2753
aatatcgagc agaaaatcga tgatattgac cacgagattg ccgatttgca ggcgaaacgt    2813
acccgcctgg tgcagcaaca tccgcgaatt gatgaataa                           2852
```

<210> SEQ ID NO 24
<211> LENGTH: 80
<212> TYPE: PRT
<213> ORGANISM: Escherichia coli

<400> SEQUENCE: 24

```
Met Leu Lys Arg Lys Val Lys Pro Ile Thr Leu Arg Asp Val Thr
1               5                   10                  15

Ile Ile Asp Asp Gly Lys Leu Arg Lys Ala Ile Thr Ala Ala Ser Leu
            20                  25                  30

Gly Asn Ala Met Glu Trp Phe Asp Phe Gly Val Tyr Gly Phe Val Ala
        35                  40                  45

Tyr Ala Leu Gly Lys Val Phe Phe Pro Gly Ala Asp Pro Ile Ser Ala
    50                  55                  60

Asn Leu Arg Val Glu Pro Ser Glu Glu Cys Asp Ala Ser Val Pro Arg
65                  70                  75                  80
```

<210> SEQ ID NO 25
<211> LENGTH: 38
<212> TYPE: DNA
<213> ORGANISM: Escherichia coli
<220> FEATURE:
<221> NAME/KEY: misc_feature
<222> LOCATION: (1)..(38)
<223> OTHER INFORMATION: Primer serCF(XbaI)

<400> SEQUENCE: 25

```
aggtgctcta gagtccgcgc tgtgcaaatc cagaatgg                            38
```

<210> SEQ ID NO 26
<211> LENGTH: 37
<212> TYPE: DNA
<213> ORGANISM: Escherichia coli
<220> FEATURE:
<221> NAME/KEY: misc_feature
<222> LOCATION: (1)..(37)
<223> OTHER INFORMATION: Primer serCR(HindIII)

<400> SEQUENCE: 26

```
tacaccaagc ttaactctct acaacagaaa taaaaac                             37
```

<210> SEQ ID NO 27
<211> LENGTH: 33
<212> TYPE: DNA
<213> ORGANISM: Escherichia coli
<220> FEATURE:
<221> NAME/KEY: misc_feature
<222> LOCATION: (1)..(33)
<223> OTHER INFORMATION: Primer serAF(XbaI)

<400> SEQUENCE: 27

```
ctgtagtcta gattagtaca gcagacgggc gcg                                 33
```

<210> SEQ ID NO 28
<211> LENGTH: 68
<212> TYPE: DNA

<213> ORGANISM: Escherichia coli
<220> FEATURE:
<221> NAME/KEY: misc_feature
<222> LOCATION: (1)..(68)
<223> OTHER INFORMATION: Primer serAR(SHSSNB)

<400> SEQUENCE: 28
caagagctca agcttgcatg cgattcccgg gcggccgcaa taagatctcc gtcagggcgt    60
ggtgaccg                                                            68

<210> SEQ ID NO 29
<211> LENGTH: 34
<212> TYPE: DNA
<213> ORGANISM: Escherichia coli
<220> FEATURE:
<221> NAME/KEY: misc_feature
<222> LOCATION: (1)..(34)
<223> OTHER INFORMATION: Primer serB(SphI)

<400> SEQUENCE: 29
ccatgcgcat gcccacccct tgaaaatttg agac                               34

<210> SEQ ID NO 30
<211> LENGTH: 75
<212> TYPE: DNA
<213> ORGANISM: Escherichia coli
<220> FEATURE:
<221> NAME/KEY: misc_feature
<222> LOCATION: (1)..(75)
<223> OTHER INFORMATION: Primer serB(SmaI)

<400> SEQUENCE: 30
ccgcatgtcg acatcccggg gcagaaaggc ccacccgaag gtgagccagt gtgattactt    60
ctgattcagg ctgcc                                                    75

<210> SEQ ID NO 31
<211> LENGTH: 35
<212> TYPE: DNA
<213> ORGANISM: Escherichia coli
<220> FEATURE:
<221> NAME/KEY: misc_feature
<222> LOCATION: (1)..(35)
<223> OTHER INFORMATION: Primer glyA-downstream

<400> SEQUENCE: 31
atctaaagat ctgttacgac agatttgatg gcgcg                              35

<210> SEQ ID NO 32
<211> LENGTH: 33
<212> TYPE: DNA
<213> ORGANISM: Escherichia coli
<220> FEATURE:
<221> NAME/KEY: misc_feature
<222> LOCATION: (1)..(33)
<223> OTHER INFORMATION: glyA-upstream

<400> SEQUENCE: 32
ttcatcgcgg ccgcgaaaga atgtgatgaa gtg                                33

<210> SEQ ID NO 33
<211> LENGTH: 30
<212> TYPE: DNA
<213> ORGANISM: Escherichia coli
<220> FEATURE:
<221> NAME/KEY: misc_feature
<222> LOCATION: (1)..(30)
<223> OTHER INFORMATION: Primer proPmut1(HindIII)

<400> SEQUENCE: 33
gtcaaagctt atatggtcgc cagaagatcc                              30

<210> SEQ ID NO 34
<211> LENGTH: 30
<212> TYPE: DNA
<213> ORGANISM: Escherichia coli
<220> FEATURE:
<221> NAME/KEY: misc_feature
<222> LOCATION: (1)..(30)
<223> OTHER INFORMATION: Primer proPmut2(BamHI)

<400> SEQUENCE: 34
gtcaggatcc tcagccgcat tacacagttg                              30

<210> SEQ ID NO 35
<211> LENGTH: 1564
<212> TYPE: DNA
<213> ORGANISM: Escherichia coli
<220> FEATURE:
<221> NAME/KEY: misc_feature
<222> LOCATION: (5)..(10)
<223> OTHER INFORMATION: Erkennungssequenz HindIII
<220> FEATURE:
<221> NAME/KEY: mutation
<222> LOCATION: (969)..(969)
<223> OTHER INFORMATION: M8-Mutation: Austausch a zu t an Position 1234,
      bedingt E412*
<220> FEATURE:
<221> NAME/KEY: misc_feature
<222> LOCATION: (1534)..(1539)
<223> OTHER INFORMATION: Erkennungssequenz BamHI

<400> SEQUENCE: 35
gtcaaagctt atatggtcgc cagaagatcc tcgctatcac tattgtgatt atgtcgatca      60
gtacgttctg tattggctta ataccgtcct acgacacgat tggtatttgg caccgattc     120 tgctgttgat ctgtaagatg cacaaggtt tctcggtcgg cggtgaatat accggggcgt     180
cgatatttgt tgcggaatac tcccctgacc gtaaacgtgg ctttatgggc agctggctgg     240
acttcggttc tattgccggg tttgtgctgg gtgcgggcgt ggtggtgtta atttcgacca     300
ttgtcggcga agcgaacttc ctcgattggg gctggcgtat tccgttcttt atcgctctgc     360
cgttagggat tatcgggctt tacctgcgcc atgcgctgga agagactccg gcgttccagc     420
agcatgtcga taaactggaa cagggcgacc gtgaaggttt gcaggatggc ccgaaagtct     480
cgtttaaaga gattgccact aaatactggc gcagcctgtt gacatgtatt ggtctggtaa     540
ttgccaccaa cgtgacttac tacatgttgc tgacctatat gccgagttat ttgtcgcata     600
acctgcatta ctccgaagac cacggggtgc tgattattat cgccattatg atcggtatgc     660
tgtttgtcca gccggtgatg ggcttgctga gtgaccgttt tggccgtcgt ccgtttgtgc     720
tacttgcgtc cgtttgtgct acttggtagt gttgccctgt ttgtgttggc gatcccggcg     780
tttattctga ttaacagtaa cgtcatcggc ctgatttttg ccgggttact gatgctggcg     840
gtgatcctta actgctttac gggcgttatg gcttctacct tgccagcgat gttcccgacg     900
catatccgtt acagcgcgct ggcggcggca tttaatattt cggtgctggt tgccggtctg     960
acgccaacgc tggcggcctg gctggtcgaa agctcgcaga atctgatgat gcctgcctat    1020
tacctgatgg tagtgcggt ggttggttta atcaccggcg taaccatgaa agagacggca    1080
aatcgtccgt tgaaaggtgc gacaccggcg gcgtcagata tacaggaagc gaaggaaatt    1140
ctcgtcgagc attacgataa tatcgagcag aaaatcgatg atattgacca cgagattgcc    1200

| | |
|---|---|
| gatttgcagg cgaaacgtac ccgcctggtg cagcaacatc cgcgaattga tgaataagct | 1260 |
| gaaacggatg gcctgatgtg acgctgtctt atcaggccaa ttgaactctt aaggttcact | 1320 |
| taatctctga cgcgcatact ctcctccagg ttaacggagg agagtgcaat gaaaaaccgt | 1380 |
| gtttatgaaa gtttaactac cgtgttcagc gtgctggtgg tcagcagctt tctttatatc | 1440 |
| tggtttgcca cgtactgatc tttcttcagc cgtacccagg cccgcgtgcc ggaagtctct | 1500 |
| tgccggtttt gcaggaaaaa ctgcccgtga tgcaactgtg taatgcggct gagcggccgc | 1560 |
| tcag | 1564 |

<210> SEQ ID NO 36
<211> LENGTH: 1542
<212> TYPE: DNA
<213> ORGANISM: Escherichia coli
<220> FEATURE:
<221> NAME/KEY: misc_feature
<222> LOCATION: (5)..(10)
<223> OTHER INFORMATION: Erkennungssequenz HindIII
<220> FEATURE:
<221> NAME/KEY: mutation
<222> LOCATION: (588)..(589)
<223> OTHER INFORMATION: M4-Mutation: Deletion eines A nach
    Nukleotidposition 854
<220> FEATURE:
<221> NAME/KEY: misc_feature
<222> LOCATION: (1533)..(538)
<223> OTHER INFORMATION: Erkennungssequenz BamHI

<400> SEQUENCE: 36

| | |
|---|---|
| gtcaaagctt atatggtcgc cagaagatcc tcgctatcac tattgtgatt atgtcgatca | 60 |
| gtacgttctg tattggctta ataccgtcct acgacacgat tggtatttgg caccgattc | 120 |
| tgctgttgat ctgtaagatg gcacaaggtt tctcggtcgg cggtgaatat accggggcgt | 180 |
| cgatatttgt tgcggaatac tcccctgacc gtaaacgtgg ctttatgggc agctggctgg | 240 |
| acttcggttc tattgccggg tttgtgctgg gtgcgggcgt ggtggtgtta atttcgacca | 300 |
| ttgtcggcga agcgaacttc ctcgattggg gctggcgtat tccgttcttt atcgctctgc | 360 |
| cgttagggat tatcgggctt tacctgcgcc atgcgctgga agagactccg gcgttccagc | 420 |
| agcatgtcga taaactggaa cagggcgacc gtgaaggttt gcaggatggc ccgaaagtct | 480 |
| cgtttaaaga gattgccact aaatactggc gcagcctgtt gacatgtatt ggtctggtaa | 540 |
| ttgccaccaa cgtgacttac tacatgttgc tgacctatat gccgagtttt tgtcgcataa | 600 |
| cctgcattac tccgaagacc acggggtgct gattattatc gccattatga tcggtatgct | 660 |
| gtttgtccag ccggtgatgg gcttgctgag tgaccgtttt ggccgtcgtc cgtttgtgct | 720 |
| acttggtagt gttgccctgt ttgtgttggc gatcccggcg tttattctga ttaacagtaa | 780 |
| cgtcatcggc ctgattttg ccgggttact gatgctggcg gtgatcctta actgctttac | 840 |
| gggcgttatg gcttctacct tgccagcgat gttcccgacg catatccgtt acagcgcgct | 900 |
| ggcggcggca tttaatattt cggtgctggt tgccggtctg acgccaacgc tggcggcctg | 960 |
| gctggtcgaa agctcgcaga atctgatgat gcctgcctat tacctgatgg tagtggcggt | 1020 |
| ggttggttta atcaccggcg taaccatgaa agagacggca atcgtccgt tgaaaggtgc | 1080 |
| gacaccggcg gcgtcagata tacaggaagc gaaggaaatt ctcgtcgagc attacgataa | 1140 |
| tatcgagcag aaaatcgatg atattgacca cgagattgcc gatttgcagg cgaaacgtac | 1200 |
| ccgcctggtg cagcaacatc cgcgaattga tgaataagct gaaacggatg gcctgatgtg | 1260 |
| acgctgtctt atcaggccaa ttgaactctt aaggttcact taatctctga cgcgcatact | 1320 |

```
ctcctccagg ttaacggagg agagtgcaat gaaaaaccgt gtttatgaaa gtttaactac    1380
cgtgttcagc gtgctggtgg tcagcagctt tctttatatc tggtttgcca cgtactgatc    1440
tttcttcagc cgtacccagg cccgcgtgcc ggaagtctct tgccggtttt gcaggaaaaa    1500
ctgcccgtga tgcaactgtg taatgcggct gaggatcctg ac                       1542

<210> SEQ ID NO 37
<211> LENGTH: 1563
<212> TYPE: DNA
<213> ORGANISM: Escherichia coli
<220> FEATURE:
<221> NAME/KEY: misc_feature
<222> LOCATION: (5)..(10)
<223> OTHER INFORMATION: Erkennungssequenz HindIII
<220> FEATURE:
<221> NAME/KEY: mutation
<222> LOCATION: (722)..(740)
<223> OTHER INFORMATION: M6-Mutation: 19bp Insertion nach
      Nukleotidposition 973
<220> FEATURE:
<221> NAME/KEY: misc_feature
<222> LOCATION: (1553)..(1558)
<223> OTHER INFORMATION: Erkennungssequenz BamHI

<400> SEQUENCE: 37
gtcaaagctt atatggtcgc cagaagatcc tcgctatcac tattgtgatt atgtcgatca     60
gtacgttctg tattggctta ataccgtcct acgacacgat tggtatttgg caccgattc    120 tgctgttgat ctgtaagatg gcacaaggtt tctcggtcgg cggtgaatat accggggcgt    180
cgatatttgt tgcggaatac tcccctgacc gtaaacgtgg ctttatgggc agctggctgg    240
acttcggttc tattgccggg tttgtgctgg gtgcgggcgt ggtggtgtta atttcgacca    300
ttgtcggcga agcgaacttc ctcgattggg gctggcgtat tccgttcttt atcgctctgc    360
cgttagggat tatcgggctt tacctgcgcc atgcgctgga agagactccg gcgttccagc    420
agcatgtcga taaactggaa cagggcgacc gtgaaggttt gcaggatggc ccgaaagtct    480
cgtttaaaga gattgccact aaatactggc gcagcctgtt gacatgtatt ggtctggtaa    540
ttgccaccaa cgtgacttac tacatgttgc tgacctatat gccgagttat ttgtcgcata    600
acctgcatta ctccgaagac cacggggtgc tgattattat cgccattatg atcggtatgc    660
tgtttgtcca gccggtgatg ggcttgctga gtgaccgttt tggccgtcgt ccgtttgtgc    720
tacttgcgtc cgtttgtgct acttggtagt gttgccctgt ttgtgttggc gatcccggcg    780
tttattctga ttaacagtaa cgtcatcggc ctgattttg ccgggttact gatgctggcg    840
gtgatcctta actgctttac gggcgttatg gcttctacct tgccagcgat gttcccgacg    900
catatccgtt acagcgcgct ggcggcggca tttaatattt cggtgctggt tgccggtctg    960
acgccaacgc tggcggcctg gctggtcgaa agctcgcaga atctgatgat gcctgcctat    1020
tacctgatgg tagtggcggt ggttggttta atcaccggcg taaccatgaa agagacggca    1080
aatcgtccgt tgaaggtgc gacaccggcg gcgtcagata tacaggaagc gaaggaaatt    1140
ctcgtcgagc attacgataa tatcgagcag aaaatcgatg atattgacca cgagattgcc    1200
gatttgcagg cgaaacgtac ccgcctggtg cagcaacatc cgcgaattga tgaataagct    1260
gaaacggatg gcctgatgtg acgctgtctt atcaggccaa ttgaactctt aaggttcact    1320
taatctctga cgcgcatact ctcctccagg ttaacggagg agagtgcaat gaaaaaccgt    1380
gtttatgaaa gtttaactac cgtgttcagc gtgctggtgg tcagcagctt tctttatatc    1440
tggtttgcca cgtactgatc tttcttcagc cgtacccagg cccgcgtgcc ggaagtctct    1500
```
tgccggtttt gcaggaaaaa ctgcccgtga tgcaactgtg taatgcggct gagggatcct    1560
cag                                                                  1563

<210> SEQ ID NO 38
<211> LENGTH: 3503
<212> TYPE: DNA
<213> ORGANISM: Escherichia coli
<220> FEATURE:
<221> NAME/KEY: gene
<222> LOCATION: (1001)..(2503)
<223> OTHER INFORMATION: Kodierregion proP

<400> SEQUENCE: 38
ttctttcgcg tgtgcagctt cagacatgga cgaacggcgg catgttaaat gcgccgctta      60
gcctgcgtct gacattggtg gaaaaactgg cgtcgatgct ggatcccggt catctggcac     120
tgacgcagat cgcgcagcat ctggcgctgc tgcaaaaaat ggatcaccgc cagcactctg     180
cttccccgga gctcccccag caaattgccg ccttgtatga gtggttttca gcccgttgtc     240
gctggaagga aaaggcgtta acgcaacgag gcctactggt gcaggcaggt gatcagagcg     300
agcaaatttt tacccgctgg cgtgctgggg cgtataacgc ctggtcgttg cctgggcgct     360
gttttatcgt tctggaggag ttgcgctggg gggcatttgg cgatgcctgc cgtctgggaa     420
gcccgcaagc ggtggcgttg ttgctgggtg atttgctcga gaaagcgaca caacatctgg     480
cagagagtat caatgcggca ccgaccacgc gtcactatta ccatcagtgg tttgcctctt     540
cgaccgttcc gacgggcggg gagcatgctg attttttaag ttggctggga agtggaccca     600
cggcagataa acaacccgtt tgctggtcag tgacccaacg ctggcaaact gtcgcgctgg     660
ggatgccacg actctgttca gcgcagcgtc tggcgggggc aatgctcgag gaaatcttct     720
ctgtaaattt ggcgtaaata atcagttaca tcaatgagtc ctaaacgaaa tccatgtgtg     780
aagttgatca caaatttaaa cactggtagg gtaaaaaggt cattaactgc ccaattcagg     840
cgtcaactgg tttgattgta cattccttaa ccggagggtg taagcaaacc cgctacgctt     900
gttacagaga ttgcatcctg caattcccgc tcccctttg cggccgtcgc gctgattttt      960
ctggcgtttg cggaaatggg ccaactctgc gaggaaagct atgctgaaaa ggaaaaaagt    1020
aaaaccgatt accttcgtg atgtcaccat tattgatgac ggtaaactgc gtaaagccat     1080
taccgcagca tcactgggta atgcaatgga atggttcgat tttggtgttt atggttttgt    1140
tgcttacgca ttaggtaaag ttttttttccc ggggctgac cccagcgtgc agatggttgc    1200
tgcacttgcc actttctccg ttccctttct gattcgaccg cttggcggac tcttcttttgg   1260 tatgttgggc gataaatatg gtcgccagaa gatcctcgct atcactattg tgattatgtc    1320
gatcagtacg ttctgtattg gcttaatacc gtcctacgac acgattggta tttgggcacc    1380
gattctgctg ttgatctgta agatggcaca aggtttctcg gtcggcggtg aatataccgg    1440
ggcgtcgata tttgttgcgg aatactcccc tgaccgtaaa cgtggcttta tgggcagctg    1500 gctggactc ggttctattg ccgggtttgt gctgggtgcg ggcgtggtgg tgttaatttc     1560
gaccattgtc ggcgaagcga acttcctcga ttggggctgg cgtattccgt tctttatcgc    1620
tctgccgtta gggattatcg ggctttacct gcgccatgcg ctggaagaga ctccggcgtt   1680
ccagcagcat gtcgataaac tggaacaggg cgaccgtgaa ggtttgcagg atggcccgaa   1740
agtctcgttt aaagagattg ccactaaata ctggcgcagc ctgttgacat gtattggtct    1800
ggtaattgcc accaacgtga cttactacat gttgctgacc tatatgccga gttatttgtc    1860

```
gcataacctg cattactccg aagaccacgg ggtgctgatt attatcgcca ttatgatcgg    1920
tatgctgttt gtccagccgg tgatgggctt gctgagtgac cgttttggcc gtcgtccgtt    1980
tgtgctactt ggtagtgttg ccctgtttgt gttggcgatc ccggcgttta ttctgattaa    2040
cagtaacgtc atcggcctga tttttgccgg gttactgatg ctggcggtga tccttaactg    2100
ctttacgggc gttatggctt ctaccttgcc agcgatgttc ccgacgcata tccgttacag    2160
cgcgctggcg gcggcattta atatttcggt gctggttgcc ggtctgacgc caacgctggc    2220
ggcctggctg gtcgaaagct cgcagaatct gatgatgcct gcctattacc tgatggtagt    2280
ggcggtggtt ggtttaatca ccggcgtaac catgaaagag acggcaaatc gtccgttgaa    2340
aggtgcgaca ccggcggcgt cagatataca ggaagcgaag gaaattctcg tcgagcatta    2400
cgataatatc gagcagaaaa tcgatgatat tgaccacgag attgccgatt tgcaggcgaa    2460
acgtacccgc ctggtgcagc aacatccgcg aattgatgaa taagctgaaa cggatggcct    2520
gatgtgacgc tgtcttatca ggccaattga actcttaagg ttcacttaat ctctgacgcg    2580
catactctcc tccaggttaa cggaggagag tgcaatgaaa aaccgtgttt atgaaagttt    2640
aactaccgtg ttcagcgtgc tggtggtcag cagctttctt tatatctggt ttgccacgta    2700
ctgatctttc ttcagccgta cccaggcccg cgtgccggaa gtctcttgcc ggttttgcag    2760
gaaaaactgc ccgtgatgca actgtgtaat gcggctgaca atacttaacc ccagaccaat    2820
cccgccataa cggctgtcca tacgtacaaa cgctttactc aactcccgc atttactctc     2880 atcaatacct ggtccttcat cttcaactgc catgaccgct ccgtcatctt cttgcagctt    2940
aatcataatg ttgctgcctt gcgggctgta acgatgggcg tttctacca ggtttcgcaa     3000 taacatccgc agcagggttg catcaccctg aacggtgatg tcggcggcgc tctctggcaa    3060
tagcagggtt tgctgtcgct ggtcgagcat ggtactgagt tcgtcatacg aggggagaat    3120
gacatcttcc agcagtttta catgttgata attaccggaa gaaaatgact gtccggcacg    3180
cgccagttgc agcagctggg agacgctctc catcatctga tcaagccgtg ccactaacgg    3240
tgctacatca atgtgatgcg ttttcgccag cagttccaga tgcaaacgca ccccgccag     3300 tggcgttcgc agttcgtgcg cgacgtcagc ggtaaacaac ctttcgttat ccagcgtgct    3360
ggtcaggcga ctgaccagat cgtttaacgc cgaaaccacc gcttcgattt cgagggtggc    3420
gctgtgaatg gcaatgggcg ttaagttgtc ggcggtgcgc gcttccagct cttttttgcag   3480 ctccgccagc gggcgggtga tgc                                           3503
```